US008426588B2

(12) United States Patent
Makino et al.

(10) Patent No.: US 8,426,588 B2
(45) Date of Patent: Apr. 23, 2013

(54) PHENYLALANINE DERIVATIVES

(75) Inventors: Shingo Makino, Kawasaki (JP); Tatsuya Okuzumi, Kawasaki (JP); Toshihiko Yoshimura, Kawasaki (JP); Yuko Satake, Kawasaki (JP); Nobuyasu Suzuki, Kawasaki (JP); Hiroyuki Izawa, Kawasaki (JP); Kazuyuki Sagi, Kawasaki (JP); Akira Chiba, Kawasaki (JP); Eiji Nakanishi, Kawasaki (JP); Masahiro Murata, Kawasaki (JP); Takashi Tsuji, Kawasaki (JP)

(73) Assignee: Ajinomoto Co, Inc., Tokyo (JP)

( * ) Notice: Subject to any disclaimer, the term of this patent is extended or adjusted under 35 U.S.C. 154(b) by 0 days.

(21) Appl. No.: 13/524,318

(22) Filed: Jun. 15, 2012

(65) Prior Publication Data

US 2012/0253041 A1  Oct. 4, 2012

Related U.S. Application Data

(60) Division of application No. 12/951,180, filed on Nov. 22, 2010, now Pat. No. 8,222,405, which is a division of application No. 11/442,141, filed on May 30, 2006, now Pat. No. 7,872,125, which is a continuation of application No. 10/300,856, filed on Nov. 21, 2002, now Pat. No. 7,153,963, which is a continuation of application No. PCT/JP01/07039, filed on Aug. 15, 2001.

(30) Foreign Application Priority Data

Aug. 18, 2000 (JP) .................. 2000-248728
May 17, 2001 (JP) .................. 2001-147451

(51) Int. Cl.
*C07D 253/08* (2006.01)

(52) U.S. Cl.
USPC ........................................ 544/183

(58) Field of Classification Search .......... 544/183
See application file for complete search history.

(56) References Cited

U.S. PATENT DOCUMENTS

| | | | |
|---|---|---|---|
| 4,223,039 A | 9/1980 | Rose et al. | |
| 6,306,840 B1 | 10/2001 | Adams et al. | |
| 6,610,710 B2 | 8/2003 | Tanaka et al. | |
| 6,855,706 B2 | 2/2005 | Tanaka et al. | |
| 7,105,520 B2 | 9/2006 | Suzuki et al. | |
| 7,153,963 B2 | 12/2006 | Makino et al. | |
| 7,160,874 B2 | 1/2007 | Tanaka et al. | |
| 7,193,108 B2 | 3/2007 | Chiba et al. | |
| 7,250,516 B2 | 7/2007 | Okuzumi et al. | |
| 7,345,049 B2 | 3/2008 | Sagi et al. | |
| 7,452,905 B2 | 11/2008 | Suzuki et al. | |
| 7,605,165 B2 | 10/2009 | Sagi et al. | |
| 7,759,388 B2 | 7/2010 | Suzuki et al. | |
| 7,872,125 B2 | 1/2011 | Makino et al. | |
| 8,222,405 B2 | 7/2012 | Makino et al. | |
| 2003/0220318 A1 | 11/2003 | Suzuki et al. | |
| 2005/0101779 A1 | 5/2005 | Sagi et al. | |
| 2006/0009476 A1 | 1/2006 | Kataoka et al. | |

(Continued)

FOREIGN PATENT DOCUMENTS

| | | |
|---|---|---|
| BG | 101841 | 8/1997 |
| CN | 1067431 | 12/1992 |

(Continued)

OTHER PUBLICATIONS

Silverman, R.B. "The Organic Chemistry of Drug Design and Drug Action", Academic Press, 1992, p. 21.*

(Continued)

*Primary Examiner* — Shaojia Anna Jiang
*Assistant Examiner* — Ganapathy Krishnan
(74) *Attorney, Agent, or Firm* — Oblon, Spivak, McClelland, Maier & Neustadt, L.L.P.

(57) ABSTRACT

Specified phenylalanine derivatives and analogues thereof have an antagonistic activity to α4 integrin. They are used as therapeutic agents for various diseases concerning α4 integrin.

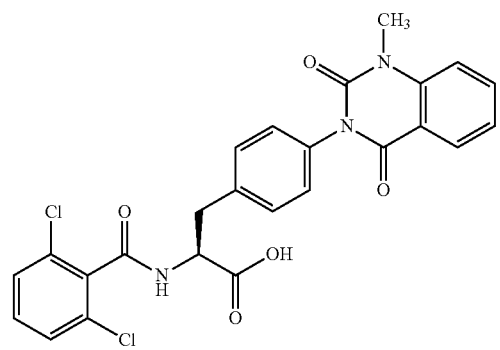

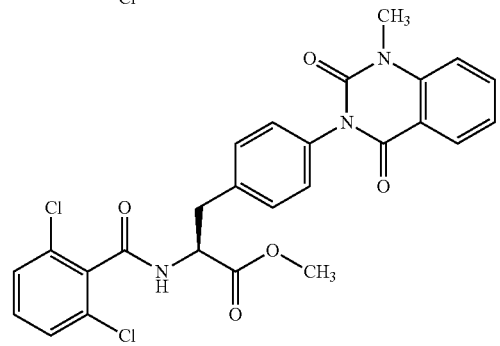

12 Claims, No Drawings

U.S. PATENT DOCUMENTS

| | | | |
|---|---|---|---|
| 2007/0018172 | A1 | 1/2007 | Takahashi et al. |
| 2008/0108634 | A1 | 5/2008 | Sagi et al. |
| 2008/0108637 | A1 | 5/2008 | Fujita et al. |
| 2008/0280909 | A1 | 11/2008 | Okuzumi et al. |

FOREIGN PATENT DOCUMENTS

| | | | |
|---|---|---|---|
| GB | 2 354 440 | | 3/2001 |
| HU | P0000914 | | 4/2001 |
| SU | 755193 | | 8/1980 |
| WO | 99/06437 | | 2/1999 |
| WO | WO 99/06431 | | 2/1999 |
| WO | 99/10312 | | 3/1999 |
| WO | WO 99/10312 | * | 3/1999 |
| WO | WO 99/10313 | | 3/1999 |
| WO | WO 99/35163 | | 7/1999 |
| WO | WO 99/36393 | | 7/1999 |
| WO | WO 99/37618 | | 7/1999 |
| WO | WO 99/43642 | | 9/1999 |
| WO | WO 01/36376 | | 5/2001 |
| WO | WO 01/42215 | | 6/2001 |
| WO | WO 01/42225 | * | 6/2001 |
| WO | WO 01/47868 | | 7/2001 |
| WO | WO 01/70670 | | 9/2001 |
| WO | WO 02/02556 | | 1/2002 |
| WO | WO 02/18320 | | 3/2002 |
| WO | WO 02/28830 | | 4/2002 |

OTHER PUBLICATIONS

The Merck Manual, 16$^{th}$ Ed., 1992, pp. 1488-1489.
Angela Zeidler et al, "Therapeutic Effects of Antibodies Against Adhesion Molecules in Murine Collagen Type II-induced Arthristis", *Autoimmunity*, 1995, vol. 21, pp. 245-252.
Daniel K. Podolsky et al, "Attenuation of Colitis in the Cotton-top Tamarin by Anti-α4 integrin Monocolonal Antibody", *J. Clin. Invest*, Jul. 1993, vol. 92, pp. 372-380.
Tsutomu Takeuchi et al, "Upregulated Expression and Function of Integrin Adhesive Receptors in Systemic Lupus Erythematosus Patients with Vasculitis", *J. Clin. Invest.*, Dec. 1993, vol. 92, pp. 3008-3016.
Supplementary European Search Report issued in European Patent Application No. 01956901.1 on Apr. 24, 2007.
Search Report issued in Bulgarian Patent Application No. 10755 on Aug. 5, 2010.
English Translation of International Preliminary Examination Report issued in PCT/JP01/07039 on Nov. 1, 2001.
Search Report issued in Hungarian Patent Application No. P0302997 on Feb. 11, 2004.
Silverman, R. B., The Organic Chemistry of Drug Design and Drug Action, Academic Press, 1992, p. 21.
S.M. Wellicome et al, "Detection of a circulating form of vascular cell adhesion molecule-1:raised levels in rheumatoid arthritis and systemic lupus erythematosus", Clin. Exp. Immunol., 1993, vol. 92, pp. 412-418.
Ted. A. Yednock et al, "Prevention of experimental autoimmune encephalomyelitis by antiboides against 4β1 integrin", Nature, Mar. 5, 1992, vol. 356, pp. 63-66.
Jody L. Baron et al, "Surface Expression of 4 integrin by CD4 T Cells is Required for Their Entry into Brain Parenchyma", J. Exp. Med., Jan. 1993, vol. 177, pp. 57-68.
Ichiro Saito et al., "Expression of Cell Adhesion Molecules in the Salivary and Lacrimal Glands of Sjogren's Syndrome", Journal of Clinical Laboratory Analysis, 1993, vol. 7, pp. 180-187.
William M. Abraham et al. "a4-Integrins Mediate Antigen-induced Late Bronchial Responses and Prolonged Airway Hyperresponsiveness in Sheep", J. Clin. Invest., Feb. 1994, vol. 93, pp. 776-787.
Hironori Sagara et al. "A Monoclonal Antibody against Very Late Activation Antigen-4 Inhibits Eosinophil Accumulation and Late Asthmatic Responses in a Guinea Pig Model of Asthma", Int. Arch. Allergy Immunol., 1997, vol. 112, pp. 287-294.
Sumi Onuma, "Immunohistochemical Studies of Infiltrating Cells in early and Chronic Lesions of Psoriasis", The Journal of Dermatology., 1994, vol. 21, pp. 223-232.
Toshinori Matsui et al, "Effects of anti-VLA-4 Monoclonal Antibody Treatment in Murine Model of Allergic Rhinitis", Acta Otolaryngol., 2000, vol. 120, pp. 761-765.
Nobuyuki Ebihara et al, "Anti VLA-4 monoclonal antibody inhibits eosinophil infiltration in allergic conjunctivitis model of guinea pig", Current Eve Research, 1999, vol. 19, No. 1, pp. 20-25.
Jody L. Baron et al, "The Pathogenesis of Adoptivie Murine Autoimmune Diabetes Requires an interaction between 4-integrins and Vascular Cell Adhesion Molecule-1", J. Clin. Invest., Apr. 1994, vol. 93, pp. 1700-1708.
Simcha R. Meisel et al, "Increased Expression of Neutrophil and Monocyte Adhesion Molecules LFA-1, and Mac-1 and Their Ligand ICAM-1 and VLA-4 Throughout the Acute Phase of Myocardinal Infarction", JACC, Jan. 1998, vol. 31, No. 1, pp. 120-125.
Peggy T. Shih et al, "Blocking Very Late Antigen-4 Integrin Decreases Leukocyte Entry and Fatty Streak Formation in Mice Fed an Atherogenic Diet", Circ. Res., Feb. 19, 1999, vol. 84, pp. 345-351.
Alan B. Lumsden et al, "Anti-VLA-4 antibody reduces intimal hyperplasia in the endarterectomized carotid artery in nonhuman primates", Journal of Vascular Surgery, Jul. 1997, vol. 26, No. 1, pp. 87-93.
Yoshihisa Mori et al, "Anti-4 integrin antibody suppresses the development of multiple myeloma and associated osteoclastic osteolysis", Blood, Oct. 1, 2004, vol. 104, No. 7, pp. 2149-2154.
Hitoshi Okahara et al, "Involvement of Very Late Activation Antigen 4 (VLA-4) and Vascular Cell Adhesion Molecule 1 (VCAM-1) in Tumor Necrosis Factor Enhancement of Experimental Metastasis", Cancer Research, Jun. 15, 1994, vol. 54, pp. 3233-3236.
Mitsuaki Isobe et al, "Immunosuppression to Cardiac Allografts and Soluble Antigens by Anti-Vascular Cellular Adhesion Molecule-1 and Anti-Very Late Antigen-4 Monoclonal Antibodies", The Journal of Immunology, 1994, vol. 153, pp. 5810-5818.
Yoji Shimizu et al, "Integrins in the Immune System", Advances in Immunology, 1999, vol. 72, pp. 325-380.
U.S. Appl. No. 13/632,474, filed Oct. 1, 2012, Kataoka, et al.

* cited by examiner

PHENYLALANINE DERIVATIVES

CROSS REFERENCES TO RELATED APPLICATIONS

This application is a divisional application of U.S. patent application Ser. No. 12/951,180, filed on Nov. 22, 2010, which was a divisional application of U.S. patent application Ser. No. 11/442,141, filed on May 30, 2006, now U.S. Pat. No. 7,872,125, which was a continuation of U.S. patent application Ser. No. 10/300,856, filed on Nov. 21, 2002, now U.S. Pat. No. 7,153,963, which was a continuation of International Patent Application No. PCT/JP01/07039, filed on Aug. 15, 2001, and claims priority to Japanese Patent Application No. 2000-248728, filed on Aug. 18, 2000, and Japanese Patent Application No. 2001-147451, filed on May 17, 2001.

BACKGROUND OF THE INVENTION

The present invention relates to new phenylalanine derivatives and the use of the phenylalanine derivatives as medicines. The present invention also relates to the compounds usable as therapeutic agents or preventive agents for inflammatory diseases in which α4 integrin-depending adhesion process participates in the pathology. It was reported that α4 integrins participate in rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The compounds of the present invention having an antagonistic effect on the α4 integrins are usable as therapeutic agents or preventive agents for the above-described diseases.

In the inflammatory reactions, it is generally understood that when a microorganism invades a tissue or when the tissue is injured, leukocytes play an important role for the exclusion of the microorganism or for the repair of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β1 through β8 subfamilies) depending on the β chains thereof. Known typical subfamilies are β1 and β3 subfamilies involved in the adhesion of cell ingredients to the extracellular matrix such as collagen and fibronectin; β2 subfamily involved in cell-to-cell adhesion in the immune system; and β7 subfamily which mainly participates in the infiltration of leukocytes into mucosal tissues (Shimizu et al., Adv. Immunol. 72: 325-380, 1999). As for the above-described α4 integrins, two kinds of molecules thereof are known. They are VLA-4 (very late antigen-4) molecule belonging to the β1 subfamily and comprising α4β1 chain and LPAM-1 (lymphocyte Peyer's patch HEV adhesion molecule-1) molecule belonging to the β7 subfamily and comprising α4β7 chain. Usually most of leukocytes circulating in the blood have only a low adhesion affinity for the vascular-endothelium cells and they cannot move out of the blood vessel. However, lymphocytes mainly comprising T cells and B cells are capable of moving out of the blood vessel by a so-called lymphocyte homing phenomenon wherein they move from the blood into the lymphoid tissue through the blood vessel wall and then they return into the blood through the lymphatic vessel under the physiological conditions. It is known that LPAM-1 molecules participate in the lymphocyte homing into the lymphoid tissue of an intestinal tract such as Peyer's patch (Butcher et al., Adv. Immunol. 72: 209-253, 1999). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophils), ICAM-1 and VCAM-1 mainly participating in the adhesion of lymphocytes, and MAdCAM-1 mainly participating in the adhesion of lymphocytes in the lymphoid tissue of an intestinal tract such as Peyer's patch (Shimizu et al., Adv. Immunol. 72: 325-380, 1999). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrix is also known (Shimizu et al., Adv. Immunol. 72: 325-380, 1999). The β1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β3 subfamily and β5 subfamily, recognize arginine-glycine-aspartic acid (RGD) sequence in fibronectin, vitronectin, tenascin and osteopontin. On the other hand, in the interaction of VLA-4 and fibronectin, the RGD sequence does not participate but a CS-1 peptide segment comprising leucine-aspartic acid-valine (LDV) as the core sequence participates (Pulido et al., J. Biol. Chem. 266: 10241-10245, 1991). Clements et al. found a sequence similar to LDV in amino acid sequences of VCAM-1 and MAdCAM-1. It has been elucidated that a variant obtained by partially modifying the CS-1-like sequence of VCAM-1 and MAdCAM-1 molecules cannot interact to VLA-4 or LPAM-1 (Clements et. al., J. Cell Sci. 107: 2127-2135, 1994, Vonderheide et al., J. Cell. Biol. 125: 215-222, 1994, Renz et al., J. Cell. Biol. 125: 1395-1406, 1994, and Kilger et al., Int. Immunol. 9: 219-226, 1997). Thus, it was found that the CS-1-like sequence is important for the interaction of VLA-4/LPAM-1 and VCAM-1/MAdCAM-1.

It was also reported that the cyclic peptide having the CS-1-like structure is antagonistic both to the interaction of VLA-4 or LPAM-1 with VCAM-1, MAdCAM-1 or CS-1 peptide (Vanderslice et al., J. Immunol. 158: 1710-1718, 1997). The above-described facts indicate that all the interactions of α4 integrin and VCAM-1, MAdCAM-1 or fibronectin can be blocked by using a suitable α4 integrin antagonist (the term "α4 integrin antagonist" in the specification indicates a substance antagonistic to α4β1 and/or α4β7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Elices, Cell 60: 577-584, 1990, Osborn et al., Cell 59: 1203-1211, 1989 and Issekutz et al., J. Eex. Med. 183: 2175-2184, 1996). Because VLA-4 is expressed on the surfaces of activated lymphocytes, monocytes, eosinophils, mast cells and neutrophils, the adhesion mechanism of VLA- 4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (van Dinther-Janssen, J. Immunol. 147: 4207-4210, 1991 and Morales-Ducret et al., J. Immunol. 149: 1424-1431, 1992), lungs and respiratory tract epithelium in asthma (ten Hacken et al., Clin. Exp. Allergy 12: 1518-1525, 1998) and allergic diseases (Randolph et al., J. Clin. Invest. 104: 1021-1029, 1999), systemic lupus erythematosus (Takeuchi et al., J. Clin. Invest. 92: 3008-3016, 1993), Sjögren's syndrome (Edwards et al., Ann. Rheum. Dis. 52: 806-811, 1993), multiple sclerosis (Steffen et al., Am. J. Pathol. 145: 189-201, 1994) and psoriasis (Groves et al., J. Am. Acad. Dermatol. 29: 67-72, 1993); atherosclerotic plagues (O'Brien et al., J. Clin. Invest. 92: 945-951, 1993), intestinal tissues of the patients with inflammatory bowel diseases such as Crohn's disease and ulcerative colitis (Koizumi et al., Gastroenterol. 103: 840-847, 1992 and Nakamura et al., Lab. Invest. 69: 77-85, 1993), inflamed tissue of Langerhans island of patients with diabetes (Martin et al., J. Autoimmun. 9: 637-643, 1996) and implants during the rejection of transplantation of heart or kidney (Herskowitz et al. Am. J. Pathol. 145: 1082-1094, 1994 and Hill et al., Kidney Int. 47: 1383-1391, 1995). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α4 integrins was effective in controlling the incidence rate or in controlling encephalomyelitis in the experimental autoimmune encephalomyelitis models, i.e. multiple sclerosis models (Yednock et al., Nature 356: 63-66, 1992 and Baron et al., J. Exp. Med. 177: 57-68, 1993). Zeidler et al. reported that in vivo administration of an antibody against α4-integrin was effective in controlling the incidence rate of mouse collagen arthritis (rheumatoid models) (Zeidler et al., Autoimmunity 21: 245-252, 1995). The therapeutic effect of an antibody against α4-integrin in asthma models was reported by Abraham et al. and Sagara et al. (Abraham et al., J. Clin. Invest. 93: 776-787, 1994 and Sagara et al., Int. Arch. Allergy Immunol. 112: 287-294, 1997). The effect of an antibody against α4-integrin in inflammatory bowel disease models was reported by Podolsky et al. (Podolsky et al., J. Clin. Invest. 92: 372-380, 1993). The effect of an antibody against α4-integrin and that against VCAM antibody in insulin-dependent diabetes models were reported by Baron et al. (Baron et al., J. Clin. Invest. 93: 1700-1708, 1994). It was made apparent with baboon models that the restenosis of a blood vessel after an angioplasty carried out because of arteriosclerosis can be inhibited by the administration of α4 integrin antibody (Lumsden et al., J. Vasc. Surg. 26: 87-93, 1997). It was also reported that α4 integrin or VCAM antibody is effective in inhibiting the rejection of an implant or inhibiting metastasis of a cancer (Isobe et al., J. Immunol. 153: 5810-5818, 1994 and Okahara et al., Cancer Res. 54: 3233-3236, 1994).

As described above, unlike VCAM-1, MAdCAM-1 which is a ligand of LPAM-1 is constitutively expressed on high endothelial venules (HEV) in the intestinal mucosa, mesenteric lymphatic nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes. Briskin et al reported an increase in the expression of MAdCAM-1 in inflamed regions in intestinal tracts of patients with inflammatory bowel diseases such as Crohn's disease and ulcerative colitis (Briskin et al., Am. J. Pathol. 151: 97-110, 1997). Hanninen et al. reported that induction of the expression is observed in an inflamed tissue of Langerhans island of NOD mouse which is a model of an insulin-dependent diabetes (Hanninen et al., J. Immunol. 160: 6018-6025, 1998). The fact that LPAM-1/MAdCAM-1 adhesion mechanism participates in the progress of diseases is apparent from the fact that conditions of mouse models with inflammatory bowel disease (Picarella et al., J. Immunol. 158: 2099-2106, 1997) and the above-described NOD mouse models are improved by the in vivo administration of antibody to MAdCAM or antibody to β7 integrin (Hanninen et al., J. Immunol. 160: 6018-6025, 1998 and Yang et al., Diabetes 46: 1542-1547, 1997).

The above-described facts indicate the possibility in that employing the blocking of VLA-4/VCAM-1, LPAM-1/VCAM-1 or LPAM-1/MAdCAM-1 adhesion mechanism by a suitable antagonist is effective in treating the chronic inflammatory diseases described above. The use of the antibody against VLA-4 as the VLA-4 antagonist is described in WO 93/13798, WO 93/15764, WO 94/16094 and WO 95/19790. Peptide compounds as VLA-4 antagonists are described in WO 94/15958, WO 95/15973, WO 96/00581 and WO 96/06108. Amino acid derivatives usable as VLA-4 antagonists are described in WO 99/10312, WO 99/10313, WO 99/36393, WO 99/37618 and WO 99/43642. However, none of them is practically used for the therapeutic treatment at present because of the lack of oral bioavailability and immunogenic properties during the use of them for a long period of time.

DISCLOSURE OF THE INVENTION

An object of the present invention is to provide new compounds having α4 integrin antagonistic effect.

Another object of the present invention is to provide the compounds having α4 integrin antagonistic effect, which can be administered orally.

Still another object of the present invention is to provide α4 integrin antagonists.

A further object of the present invention is to provide a pharmaceutical composition containing such new compounds.

An additional object of the present invention is to provide therapeutic agents or preventive agents for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

For the purpose of solving the above-described problems, the inventors have synthesized various phenylalanine derivatives and examined α4 integrin antagonistic activities thereof, and the inventors have found that specified, new phenylalanine derivatives have an excellent α4 integrin antagonistic activity. The present invention has been completed on the basis of this finding.

Namely, the present invention provides phenylalanine derivatives of the following general formula (1) and pharmaceutically acceptable salts thereof:

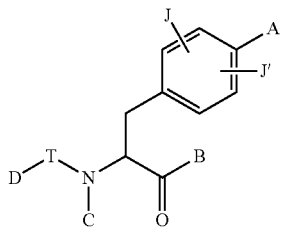
(1)

wherein A represents one of the following general formulae (2), (3), (3-1) or (3-2):

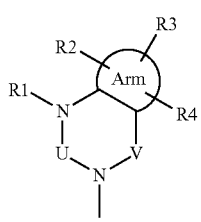
(2)

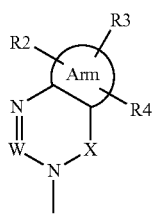
(3)

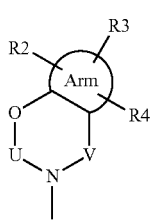
(3-1)

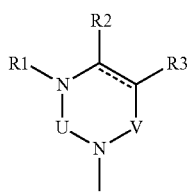
(3-2)

wherein Arm represents a cyclic alkyl group or an aromatic ring containing 0, 1, 2, 3 or 4 hetero atoms selected from the group consisting of oxygen, sulfur and nitrogen atoms, the composite line of solid line and dotted line in the formula (3-2) represents a single bond or a double bond, U, V and X represent C(=O), S(=O)$_2$, C(—R5)(—R6), C(=C(R5)(R6)), C(=S), S(=O), P(=O)(—OH) or P(—H)(=O), W represents C(—R7) or a nitrogen atom, R1, R2, R3, R4 R5, R6 and R7 may be the same or different from one another and each represent a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogeno alkoxyl group, a lower halogenoalkylthio group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or an ammonium group, R5 and R6 may be bonded together to form a ring which may contain one or two oxygen, nitrogen or sulfur atoms, B represents a hydroxyl group, a lower alkoxyl group or hydroxylamino group, C represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), D represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, C and D may be bonded together to form a ring which may contain one or two oxygen, nitrogen or sulfur atoms, T represents an interatomic bond, C(=O), C(=S), S(=O), S(=O)$_2$, N(H)—C(=O), or N(H)—C(=S), J and J' may be the same or different from each other and each represent a hydrogen atom, a halogen atom, a lower alkyl group, a lower alkyloxy group or nitro group, provided that the phenylalanine derivatives of the general formula (1) do not include compounds having the following formula (A-1) or (A-2) when A represents the formula (3-2).

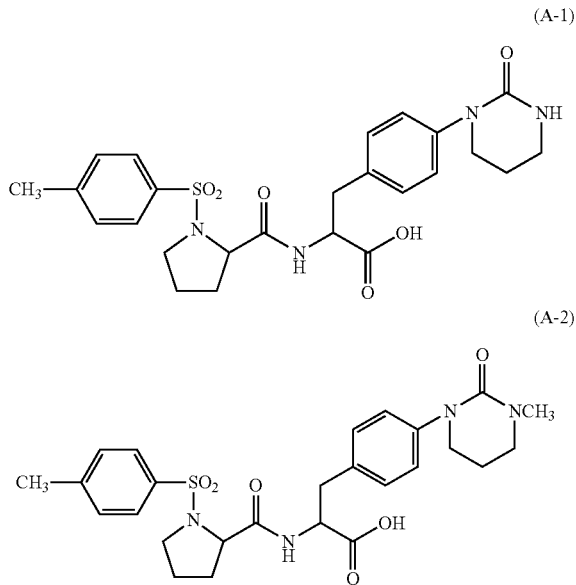

The present invention provides an α4 integrin antagonist containing the above-described phenylalanine derivative or a pharmaceutically acceptable salt thereof as the active ingredient.

The present invention also provides a pharmaceutical composition containing the above-described phenylalanine derivative or a pharmaceutically acceptable salt thereof.

The present invention further provides a therapeutic agent or preventive agent, containing the phenylalanine derivative or a pharmaceutically acceptable salt thereof as the active ingredient, for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

BEST MODE FOR CARRYING OUT THE INVENTION

The term "lower" in, for example, a lower alkyl group in the present specification indicates that the group has 1 to 6 carbon atoms and preferably 1 to 4 carbon atoms. Alkyl groups, alkenyl groups and alkynyl groups in alkyl groups, alkenyl groups, alkynyl groups, alkoxyl groups, alkylthio groups, alkanoyl groups, alkylamino groups and the like may be either linear or branched. Examples of these alkyl groups are methyl group, ethyl group, propyl group, isopropyl group, butyl group, secondary butyl group, tertiary butyl group, pentyl group and hexyl group. It is preferable that the alkyl groups have 1 to 6 carbon atoms and more preferable that the groups have 1 to 4 carbon atoms. The alkenyl groups are, for example, vinyl group, propenyl group, butenyl group and pentenyl group. It is preferable that the alkenyl groups have 2 to 6 carbon atoms and more preferable that the groups have 2 to 4 carbon atoms. The alkynyl groups include ethynyl group, propynyl group and butynyl group. It is preferable that the alkynyl groups have 2 to 8 carbon atoms and more preferable that the groups have 2 to 4 carbon atoms. The cycloalkyl groups indicate substituted or unsubstituted cycloalkyl groups such as cyclopropyl group, cyclobutyl group, cyclopentyl group, cyclohexyl group, norbornyl group, adamantyl group and cyclohexenyl group. It is preferable that the cycloalkyl groups have 3 to 8 carbon atoms and more preferable that the groups have 3 to 5 carbon atoms. The alkoxyl groups include methoxyl group, ethoxyl group, propyloxy group, isopropyloxy group, etc. It is preferable that the alkoxyl groups have 1 to 6 carbon atoms and more preferable that the groups have 1 to 4 carbon atoms. The hetero atoms include nitrogen, oxygen, sulfur, etc. The halogen atoms are fluorine, chlorine, bromine and iodine. The halogenoalkyl groups include chloromethyl group, trichloromethyl group, trifluoromethyl group, trifluoroethyl group, pentafluoroethyl group, etc. The halogenoalkoxyl groups include trichloromethoxyl group, trifluoromethoxyl group, etc. The hydroxyalkyl groups include hydroxymethyl group, hydroxyethyl group, etc. The cycloalkyl groups which may contain a hetero atom(s) in the ring thereof may be either substituted or unsubstituted. Examples of them include cyclopentyl group, cyclohexyl group, piperidyl group, piperazinyl group, morpholinyl group, pyrrolidinyl group, tetrahydrofuranyl group and uracil group, which are 4-to-8-membered cyclic group, preferably, 5-to-7-membered cyclic group.

In the present specification, the aryl groups are both substituted and unsubstituted aryl groups such as phenyl group, 1-naphthyl group and 2-naphthyl group. They are preferably phenyl group and substituted phenyl group, and the substituents are particularly preferably halogen atoms, alkoxyl groups, alkyl groups, hydroxyl group, halogenoalkyl groups and halogenoalkoxyl groups. The heteroaryl groups are both substituted and unsubstituted heteroaryl groups such as pyridyl group, pyrazyl group, pyrimidinyl group, pyrazolyl group, pyrrolyl group, triazyl group, furyl group, thienyl group, isoxazolyl group, isothiazolyl group, indolyl group, quinolyl group, isoquinolyl group and benzimidazolyl group. Preferred heteroaryl groups are pyridyl group, pyrazyl group, pyrimidinyl group, furyl group, thienyl group and substituted pyridyl, furyl and thienyl groups. Particularly preferred substituents are halogen atoms, alkoxyl groups, alkyl groups, hydroxyl group, halogenoalkyl groups and halogenoalkoxyl groups. The lower alkyl groups substituted with an aryl group(s) include, for example, substituted or unsubstituted benzyl groups and substituted or unsubstituted phenethyl groups. Particularly preferred substituents are halogen atoms, alkoxyl groups, alkyl groups, hydroxyl group, halogenoalkyl groups and halogenoalkoxyl groups. The lower alkyl groups substituted with a heteroaryl group(s) include, for example, pyridylmethyl group, and particularly preferred substituents thereof are halogen atoms, alkoxyl groups, alkyl groups, hydroxyl group, halogenoalkyl groups and halogenoalkoxyl groups. The alkanoyl groups include, for example, formyl groups, acetyl groups, propanoyl group, butanoyl group and pivaloyl group. The aroyl groups include, for example, substituted or unsubstituted benzoyl group and pyridylcarbonyl group, and the substituents thereof are particularly preferably halogen atoms, alkoxyl groups, alkyl groups, hydroxyl group, halogenoalkyl groups and halogenoalkoxyl groups. The halogenoalkanoyl groups include, for example, trichloroacetyl group and trifluoroacetyl group. The alkylsulfonyl groups include, for example, methanesulfonyl group, ethanesulfonyl group, etc. The arylsulfonyl groups include, for example, benzenesulfonyl group and p-toluenesulfonyl group. The heteroarylsulfonyl groups include, for example, pyridylsulfonyl group. The halogenoalkylsulfonyl groups include, for example, trifluoromethanesulfonyl group. The alkyloxycarbonyl groups include, for example, methoxycarbonyl group, ethoxycarbonyl group and tert-butoxycarbonyl group. The aryl-substituted alkoxycarbonyl groups include, for example, benzyloxycarbonyl group and 9-fluorenylmethoxycarbonyl group. The substituted carbamoyl groups include, for example, methylcarbamoyl group, phenylcarbamoyl group and substituted phenylcarbamoyl group, and the substituents thereof are particularly preferably halogen atoms, alkoxyl groups, alkyl groups, hydroxyl group, halogenoalkyl groups and halogenoalkoxyl groups. The substituted thiocarbamoyl groups include, for example, methylthiocarbamoyl group, phenylthiocarbamoyl group and substituted phenylthiocarbamoyl groups, and the substituents thereof are particularly preferably halogens, alkoxyl groups, alkyl groups, hydroxyl group, halogenoalkyl groups and halogenoalkoxyl groups. The substituted amino groups in this specification indicate mono-substituted or di-substituted amino groups and the substituents thereof include lower alkyl groups, lower alkyl groups substituted with an aryl group, lower alkyl groups substituted with a heteroaryl group, lower alkanoyl groups, aroyl groups, lower halogenoalkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups. The ammonium groups include such as trialkylammonium groups.

Because the phenylalanine derivatives of the general formula (1) of the present invention include asymmetric carbons, it can be considered that the phenylalanine derivatives of the general formula (1) of the present invention are optical isomers and the compound indicated in the present invention include the said optical isomers. However, L-form is preferable.

Regarding the compound in which a diastereomer exists, the diastereomer and the diastereomer mixture are included in the said phenylalanine derivatives. Because the phenylalanine derivatives of the general formula (1) of the present invention include a movable hydrogen atom, it can be considered that the phenylalanine derivatives of the general formula (1) of the present invention include a variety of tautomeric forms and the compounds indicated in the present invention include the said tautomeric forms. Further, the carboxyl groups of the compound of the present invention may be substituted with appropriate substituents which are converted into a carboxyl group in vivo. An example of such substituents is a lower alkoxycarbonyl group.

In the above-described general formula (1),
it is preferable that the groups indicated as A are both the general formulae (2) and (3), Arm in the general formulae (2) and (3) is preferably an aromatic ring and particularly a benzene ring and substituted benzene ring are preferable. R1 in the general formula (2) is preferably a hydrogen atom, a lower alkyl group and substituted lower alkyl group. Substituents thereof are preferably a phenyl group, cyano group and carboxyl group. It is preferable that R2 to R4 of the general formulae (2) and (3) are a hydrogen atom, a halogen, a hydroxyl group, a lower alkyl group, a lower alkoxy group, a halogen lower alkyl group, a substituted or unsubstituted amino group and an ammonium group.

The group represented by B is preferably a hydroxyl group. A lower alkoxy group is also preferable.

The group represented by C is preferably a lower alkyl group or a hydrogen atom and the hydrogen atom is more preferable.

As the groups represented by D, the cycloalkyl groups which may contain a hetero atom(s) in the ring thereof, aryl groups and heteroaryl groups are preferable. The cycloalkyl groups which may contain a hetero atom(s) in the ring thereof, aryl groups and heteroaryl groups are either unsubstituted or substituted, and the substituents are those described above with reference to R1, R2, R3, R4, R5, R6 and R7. Among these, the groups represented by D are particularly preferably substituted or unsubstituted cyclohexyl group or phenyl group. The substituents thereof are preferably 1 to 3 of, more preferably, 1 or 2 of lower alkyl groups or lower alkoxyl groups or halogen atoms.

The group represented by J and J' is preferably a hydrogen atom.

The group represented by T is preferably C(=O).

It is preferred that U, V and X are C(=O) and C(=S), and C(=O) is particularly preferred. W is preferably C(—R7) and —R7 is preferably a lower alkyl group, a lower alkoxyl group and a lower alkylthio group.

In the general formula (1) of the present invention, it is preferable that A represents one of the groups indicated as the general formula (2) or (3) and R1, R2, R3, R4, R5, R6 and R7 may be the same or different from one another, and each represents the groups shown below:
a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkylthio group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group or a substituted or unsubstituted sulfamoyl group, R5 and R6 may be bonded together to form a ring which may contain one or two oxygen, nitrogen or sulfur atoms.

It is preferable that, in the general formula (1) of the present invention, B represents a hydroxyl group or a lower alkoxyl group,
C represents a hydrogen atom or a lower alkyl group,
J and J' represent a hydrogen group, and
in the general formulae (2) and (3), V and X represent any of group of C=(O), S(=O)$_2$ or C(—R5)(—R6),
U represents any of group of C=(O), S(=O)$_2$, C(—R5)(—R6), C(=C(R5)(R6)), C(=S), S(=O), P(=O)(—OH) or P(—H)(=O).

Further, it is preferable that, in the general formula (1), B represents a hydroxyl group or a lower alkoxyl group, C represents a hydrogen atom or a lower alkyl group, J and J' represent a hydrogen group, and in the general formulae (2) and (3), Arm represents a benzene ring or an aromatic ring containing 1, 2, 3 or 4 hetero atoms selected from the group consisting of oxygen, sulfur and nitrogen atoms.

Further, it is preferable that, in the general formula (1), B represents a hydroxyl group or a lower alkoxyl group, C represents a hydrogen atom or a lower alkyl group, J and J' represent a hydrogen group, and in the general formulae (2) and (3), Arm represents a benzene ring or an aromatic ring containing 1, 2, 3 or 4 hetero atoms selected from the group consisting of oxygen, sulfur and nitrogen atoms, V and X represent any of group of C=(O), S(=O)$_2$ or C(—R5)(—R6), U represents any of group of C=(O), S(=O)$_2$, C(—R5)(—R6), C(=C(R5)(R6)), C(=S), S(=O), P(=O)(—OH) and P(—H)(=O).

It is also preferred that, in the general formula (1), C represents a hydrogen atom and T represents C(=O).

It is still preferred that, in the general formula (1), A represents the following formula (3-3):

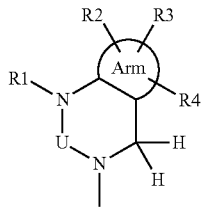

(3-3)

wherein Arm, U and R1 to R4 are the same as those described above.

In the general formula (3-3), Arm is preferably an aromatic ring, and particularly preferably a benzene ring or substituted benzene ring. R1 in the general formula (3-3) is preferably a hydrogen atom, lower alkyl group or a lower alkyl group substituted with phenyl group, cyano group or carboxyl group. R1 to R4 in the general formula (3-3) are preferably a hydrogen atom, halogen atom, hydroxyl group, lower alkyl group, lower alkoxyl group, cyano group, nitro group, an unsubstituted amino group or amino group substituted with a lower alkyl group(s).

In the general formula (1), A preferably represents the following formulae (3-4) or (3-5):

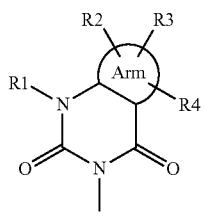

(3-4)

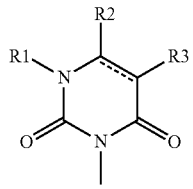

(3-5)

wherein Arm and R1 to R4 are the same as those described above, and the composite line of solid line and dotted line in the formula (3-5) represents a single bond or a double bond.

In the general formula (1), D preferably represents the following formulae (4-1), (4-2), (4-3) or (4-4):

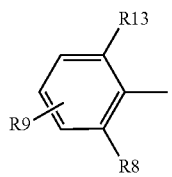

(4-1)

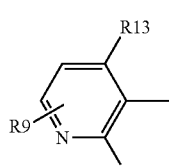

(4-2)

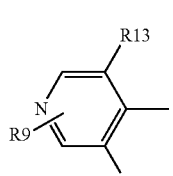

(4-3)

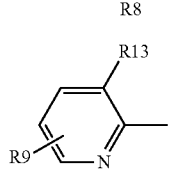

(4-4)

wherein R13 represents a halogen atom or methyl group, R8 represents a halogen atom, methyl group, trifluoromethyl group, methoxy group or a hydrogen atom, R9 represents a hydrogen atom, halogen atom, hydroxyl group, lower alkyl group, cycloalkyl group which may contain a hetero atom(s) in the ring thereof, lower alkyl group substituted with a cycloalkyl group(s) which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s), trialkylammonium group, methanesulfonyl amino group and tetrazolyl group.

In the above formulae, the formula (4-1) is preferable. Particularly, it is preferable that in the formula (4-1), R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogeno alkoxyl group, lower halogenoalkylthio group, nitro group, cyano group, amino group, amino group substituted with a lower alkyl group(s) or trialkylammonium group.

It is also preferable that in the general formula (1), A represents the formula (3-4), Arm is a benzene ring, pyridine ring, pyrazole ring or cyclohexane ring, R1 is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group.

Further, it is preferred that in the general formula (1), A represents the formula (3-4) or (3-5), D represents (4-1), (4-2), (4-3) or (4-4), B is a hydroxyl group or a lower alkoxyl group, C is a hydrogen atom, each of J and J' is a hydrogen atom and T is C(=O).

In the present invention, it is preferable that in the general formula (1), A represents the formula (3-4) wherein Arm is a benzene ring, pyridine ring, pyrazole ring or cyclohexane ring, R1 is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, D represents the formula (4-1) wherein R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogeno alkoxyl group, lower halogenoalkylthio group, nitro group, cyano group, amino group, amino group substituted with a lower alkyl group(s) or trialkylammonium group, B is a hydroxyl group or a lower alkoxyl group, C is a hydrogen atom, each of J and J' is a hydrogen atom and T is C(=O).

In the present invention, it is also preferred that in the general formula (1), A represents the formula (3-3), and in the formula (3-3), U represents C(=O) or C(=S), R1 represents a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, C represents a hydrogen atom, D represents the formula (4-1), (4-2), (4-3) or (4-4), T represents C(=O).

Further, in the present invention, it is preferred that A represents the formula (3-3), and in the formula (3-3), U represents C(=O) or C(=S), R1 represents a methyl group or ethyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, B represents a hydroxyl group or lower alkyl group, C represents a hydrogen atom, D represents the formula (4-1), wherein R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s) or trialkylammonium group, T is C(=O) and each of J and J' is a hydrogen atom.

In the present invention, phenylalanine derivatives of the following general formula and pharmaceutically acceptable salts thereof is preferable:

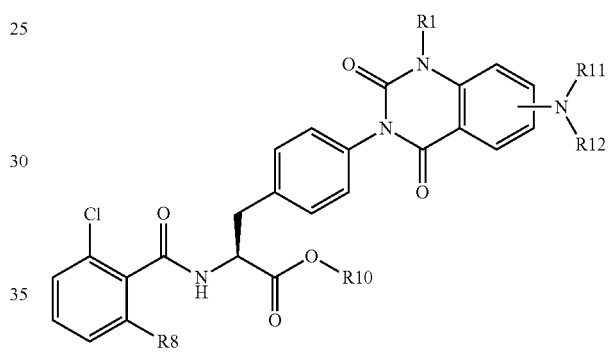

wherein R1 represents a methyl group or ethyl group, R8 represents a halogen atom or methyl group, R10 represents a hydrogen atom or a lower alkyl group, R11 and R12 may be the same or different from each other and each represents a hydrogen atom, methyl group, ethyl group or propyl group, R11 and R12 may be bonded together to form a ring, and in that case, R11-R12 represent trimethylene, tetramethylene or pentamethylene. It is particularly preferable that R10 represents a lower alkyl group.

More concretely, the compounds described in Examples are preferable though they are not particularly limited.

Especially, the compounds of the following formulae and pharmaceutically acceptable salts thereof are preferred:

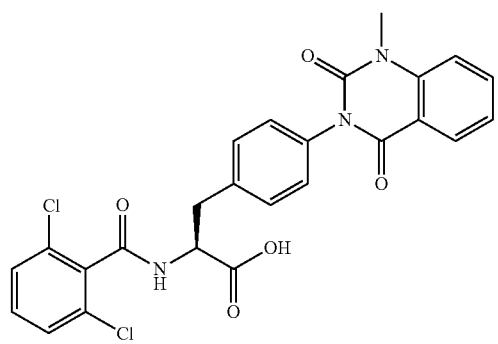

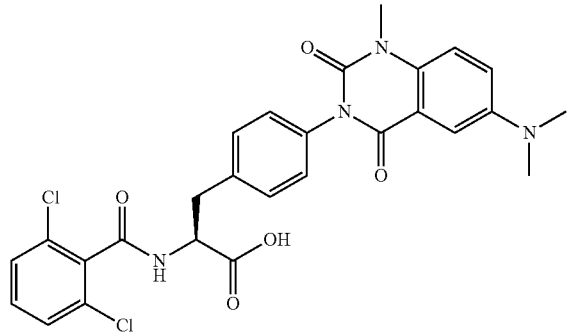
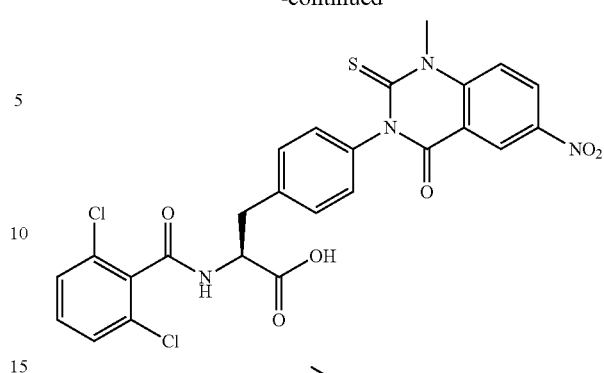
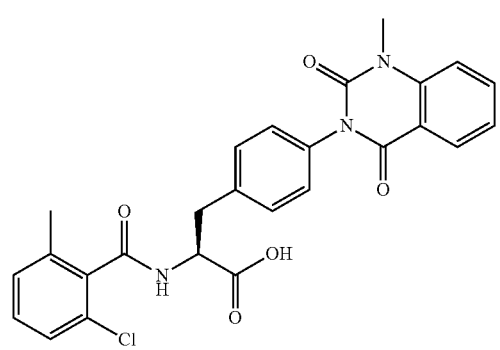
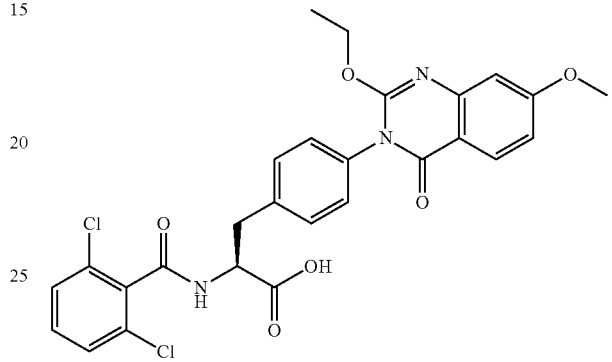
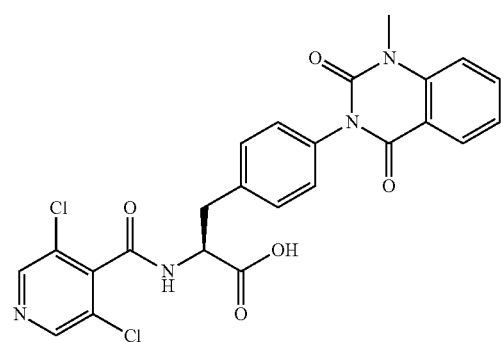
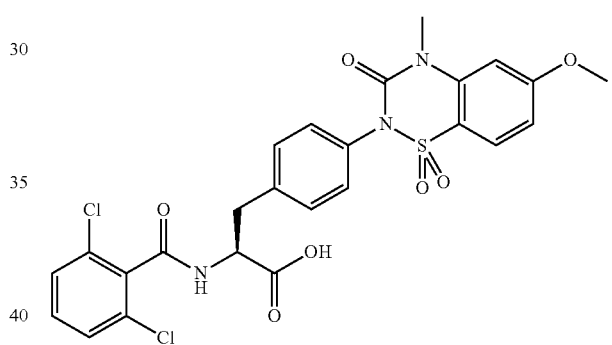
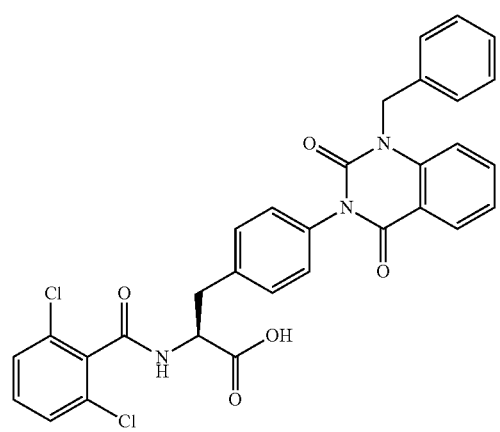
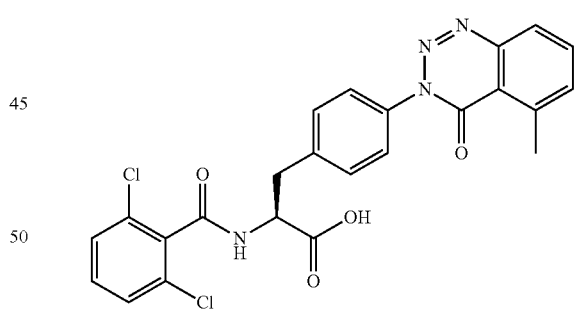
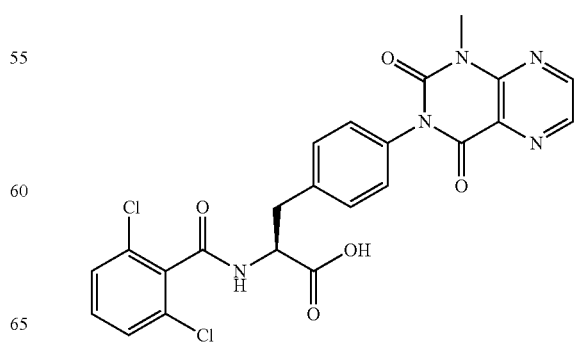

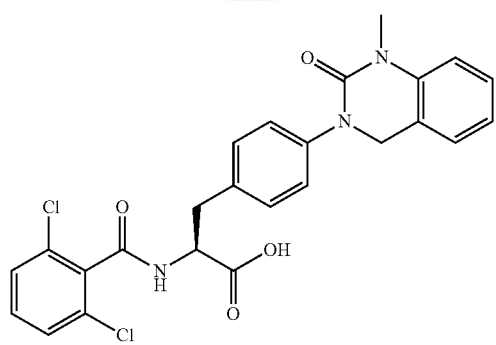
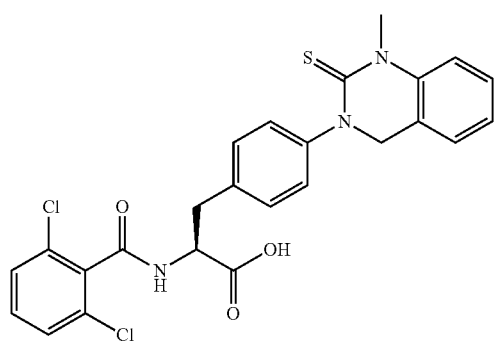
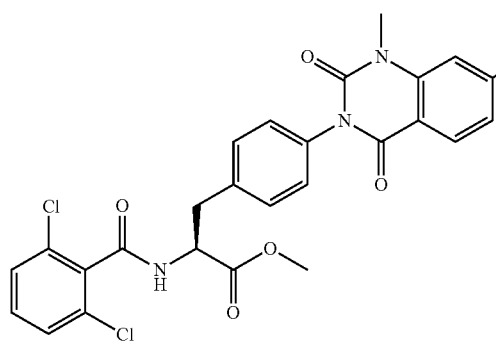
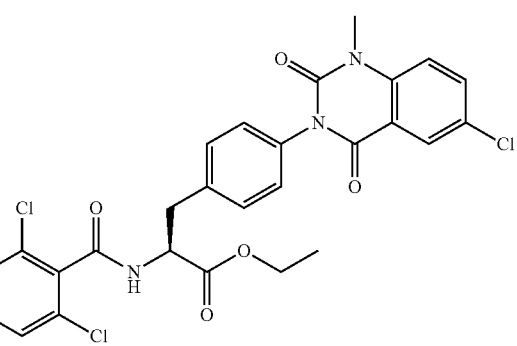
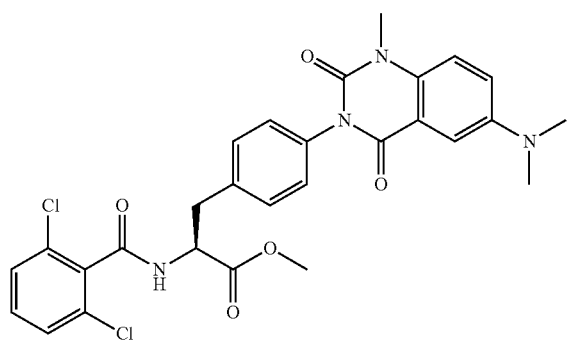
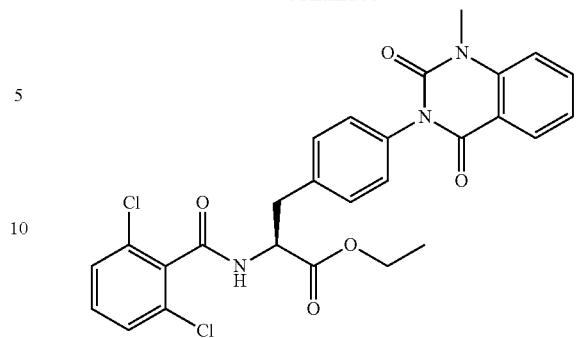
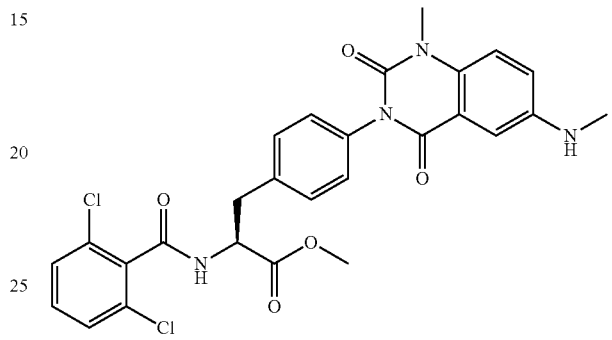
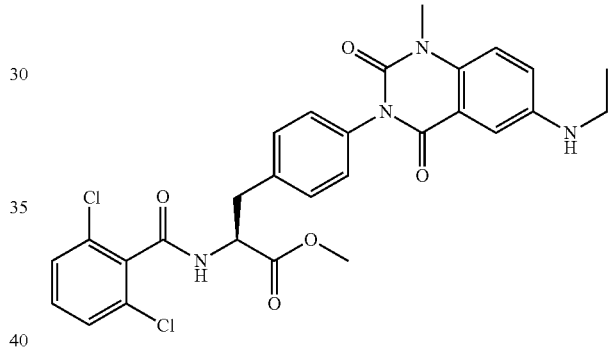
The phenylalanine derivatives (1) of the present invention can be synthesized, for example, by methods described below when B is a hydroxyl group.
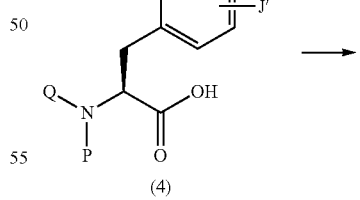
(4)
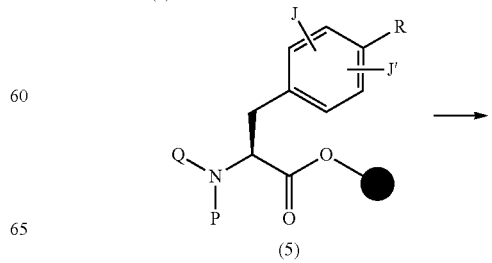
(5)

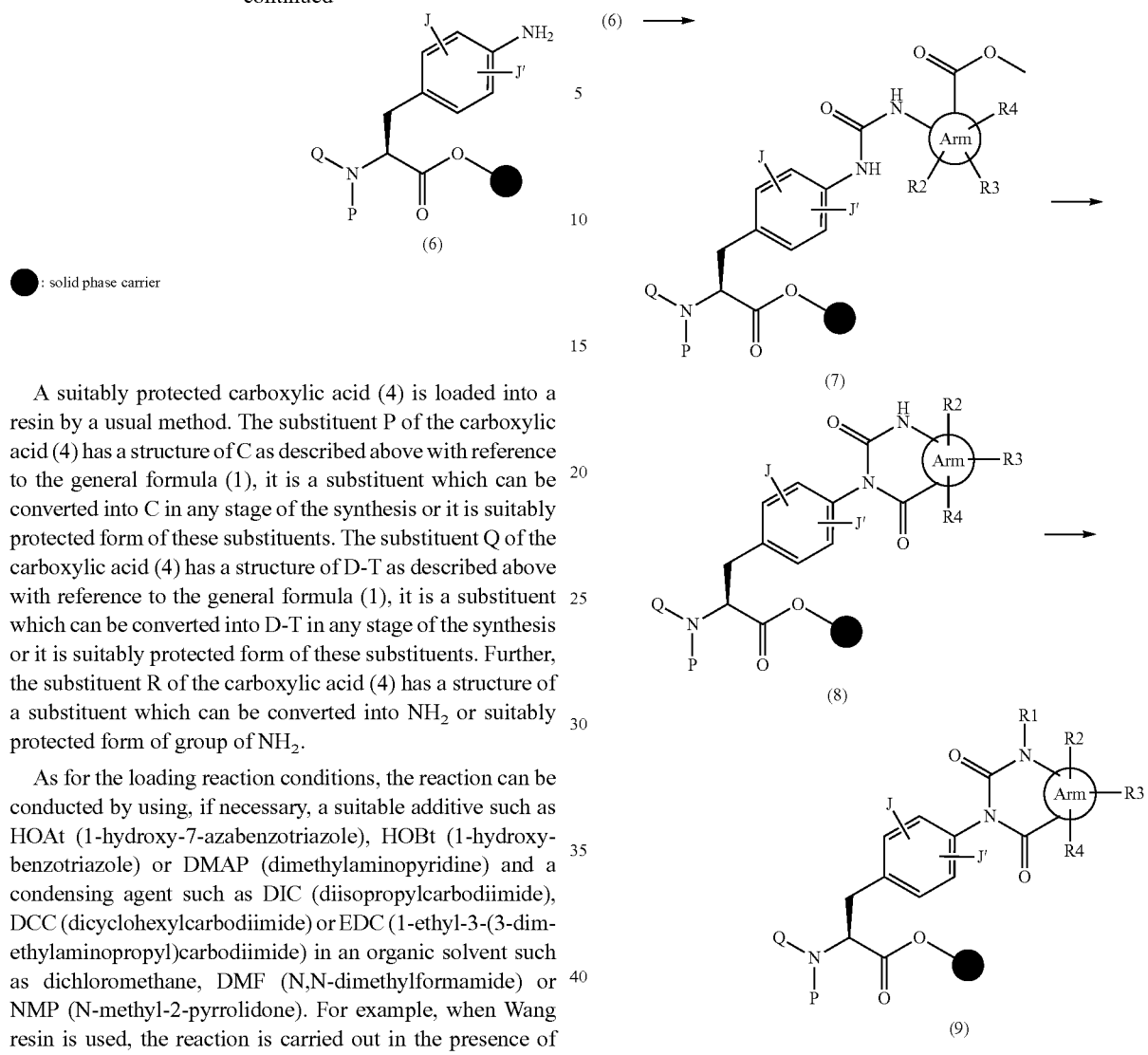

A suitably protected carboxylic acid (4) is loaded into a resin by a usual method. The substituent P of the carboxylic acid (4) has a structure of C as described above with reference to the general formula (1), it is a substituent which can be converted into C in any stage of the synthesis or it is suitably protected form of these substituents. The substituent Q of the carboxylic acid (4) has a structure of D-T as described above with reference to the general formula (1), it is a substituent which can be converted into D-T in any stage of the synthesis or it is suitably protected form of these substituents. Further, the substituent R of the carboxylic acid (4) has a structure of a substituent which can be converted into $NH_2$ or suitably protected form of group of $NH_2$.

As for the loading reaction conditions, the reaction can be conducted by using, if necessary, a suitable additive such as HOAt (1-hydroxy-7-azabenzotriazole), HOBt (1-hydroxybenzotriazole) or DMAP (dimethylaminopyridine) and a condensing agent such as DIC (diisopropylcarbodiimide), DCC (dicyclohexylcarbodiimide) or EDC (1-ethyl-3-(3-dimethylaminopropyl)carbodiimide) in an organic solvent such as dichloromethane, DMF (N,N-dimethylformamide) or NMP (N-methyl-2-pyrrolidone). For example, when Wang resin is used, the reaction is carried out in the presence of pyridine and 2,6-dichlorobenzoyl chloride in DMF to obtain an ester (5). The ester (5) can be changed to an amine (6) under suitable conditions depending on the substituent R. For example, when a nitro group is used as R, the ester (5) can be changed to the amine (6) in the presence of a reducing agent such as $SnCl_2$ or hydrates thereof in a solvent such as NMP, DMF or ethanol. In the case of an amine protected with Fmoc group (9-fluorenylmethoxycarbonyl group) (FmocNH), the protective group can be removed with a base such as piperidine in a solvent such as DMF to obtain the amine (6).

A quinazolinedione (9) wherein A represents the general formula (2) and U and V are both C(=O) in the general formula (1) can be obtained by the following method. First, an urea (7) is obtained by reacting the amine (6) with an isocyanate having a carboxylate ester group in the ortho position. Then, a quinazolinedione (8) can be obtained by a ring closure reaction with a base such as a piperidine in a solvent such as DMF or TMG (tetramethylguanidine). Further, reagents such as alkyl halide and aryl halide are reacted thereto to obtain the quinazolinedione (9), or the said compound can also be obtained by Mitsunobu reaction using alcohol.

A quinazolinedione (9) wherein A represents the general formula (2) and U and V are both C(=O) in the general formula (1) can also be synthesized by the following method. First, an amide (10) can be obtained by reacting the amine (6) with an acylchloride having a nitro group in the ortho position under the existence of 2,6-lutidine base in a solvent such as NMP, or by reacting it with a carboxylic acid having a nitro group in the ortho position activated by using a condensing agent such as DIC and, if necessary, a suitable additive such as HOAt or HOBt in an organic solvent such as DMF, NMP or dichloromethane. Then, an amine (11) is obtained by reducing the nitro group with $SnCl_2$ or hydrates thereof and cyclized by reagents such as CDI (carbonyldiimidazole), triphosgene or p-nitrophenylchloroformate to obtain the quinazolinedione (8).

As the other synthesizing methods, the quinazolinedione (8) can also be obtained by the following method. First, an amide (11) can be obtained by reacting the amine (6) with a carboxylic acid having a amino group in the ortho position activated by using a condensing agent such as DIC and, if necessary, a suitable additive such as HOAt or HOBt in an organic solvent such as DMF, NMP or dichloromethane. Then, an amide (11) is cyclized by reagents such as CDI, triphosgene or p-nitrophenylchloroformate to obtain the quinazolinedione (8). This method applies to one of the synthesizing methods in case that A represents the general formula (3-1) and U and V are both C(=O) in the general formula (1), when a variety of salicylic acids is used instead of the above carboxylic acid and the resulting amide (11) is cyclized by reagents such as CDI, triphosgene or p-nitrophenylchloroformate after adding a base such as ethanolamine.

(6) ⟶

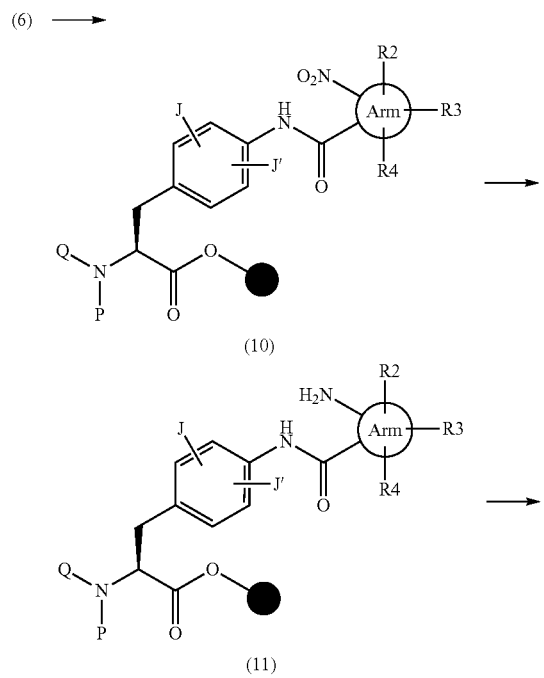

(10)

(11)

A quinazolinedione (9) wherein A represents the general formula (2), U and V are both C(=O) and R2, R3 or R4 is an electron withdrawing substituent such as a nitro group in the general formula (1) can also be synthesized by the following method. First, an amide (42) can be obtained by reacting the amine (6) with a carboxylic acid having a fluoro group in the ortho position activated by using a condensing agent such as DIC and, if necessary, a suitable additive such as HOAt or HOBt in an organic solvent such as DMF, NMP or dichloromethane. Then, after an amine (43) is obtained by substituting a fluoro group with an amine, the amine (43) is cyclized by reagents such as CDI, triphosgene or p-nitrophenylchloroformate to obtain the quinazolinedione (9).

(6) ⟶

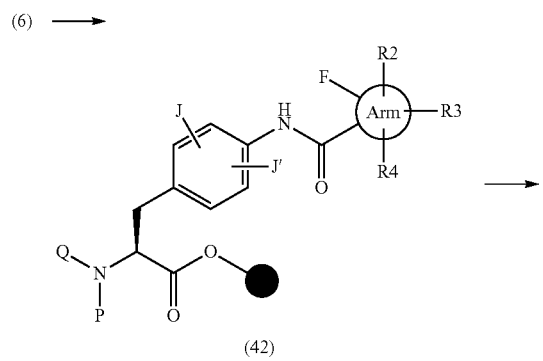

(42)

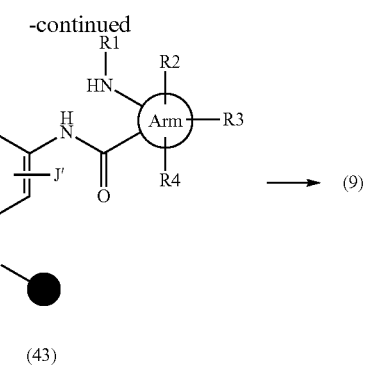

(43)

As the example of the methods for synthesizing an ester (12) wherein A represents the general formula (2), U is C(=S) and V is C(=O) in the general formula (1), the said ester can be obtained by reacting the amine (6) with an isothiocyanate having a carboxylate group in the ortho position.

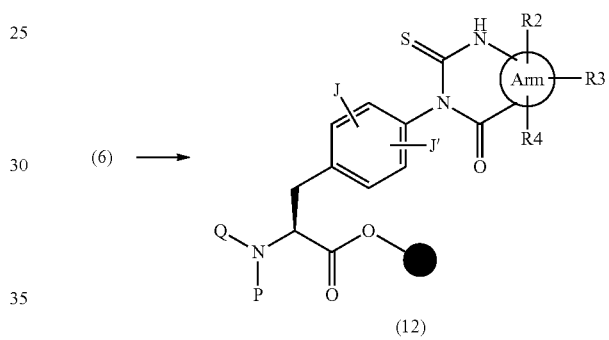

(12)

As the example of the methods for synthesizing an ester (44) wherein A represents the general formula (2), U is C(=S) and V is C(=O) in the general formula (1), the said ester can be obtained by reacting the amine (43) with a thiocarbonyldiimidazole in a solvent such as decahydro-naphthalene and toluene.

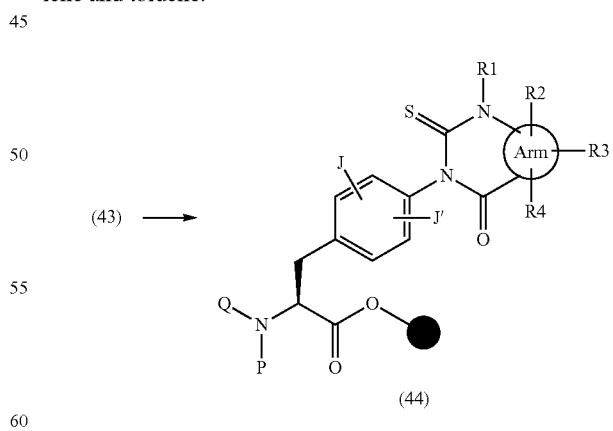

(44)

Among ester (13) wherein A represents the general formula (3) and W is C(—R7) in the general formula (1), particularly those that R7 is a lower alkylthio group, a lower alkylthio group substituted with a cycloalkyl group which may contain a hetero atom(s) in the ring thereof, a lower alkylthio group substituted with an aryl group or a lower alkylthio group substituted with a heteroaryl group can be obtained by reacting the ester (12) with reagents such as alkyl halide and aryl halide.

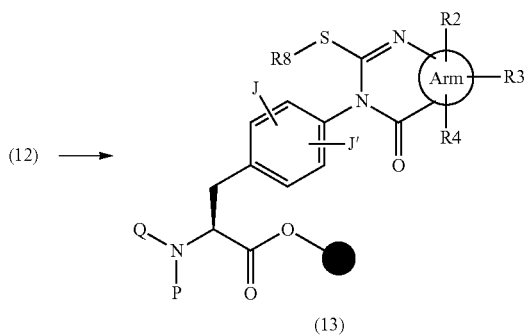

(12) →

(13)

Further, among ester (14) wherein A represents the general formula (3) and W is C(—R7) in the general formula (1), particularly those that R7 is a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group can be obtained by reacting the amine (11) with various orthoformates or equivalents thereof. The said ester can also be obtained by oxidation after reacting with aldehyde or acetal.

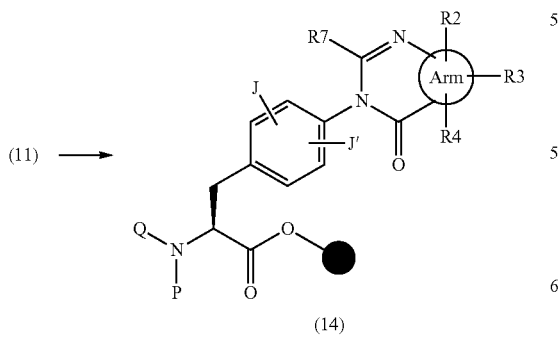

(11) →

(14)

Among ester (14) wherein A represents the general formula (3) and W is C(—R7) in the general formula (1), particularly those that R7 is a substituted amino group can be synthesized as follows. First, Y in an ester (15) is a group such as an azide group and amino group and each can be changed to an iminophosphine (16) by reacting with triphenylphosphine or triphenylphosphine under the existence of diisopropylazodicarboxylic acid respectively. Then, carbodiimide (17) (n is 0 to 4.) is obtained by Aza-Wittig reaction of the iminophosphine (16) with an isocyanate having a carboxylate group in the ortho position. After the nucleophilic attack to the carbodiimide of the amine and the ring closure thereafter, the ester (18) can be synthesized.

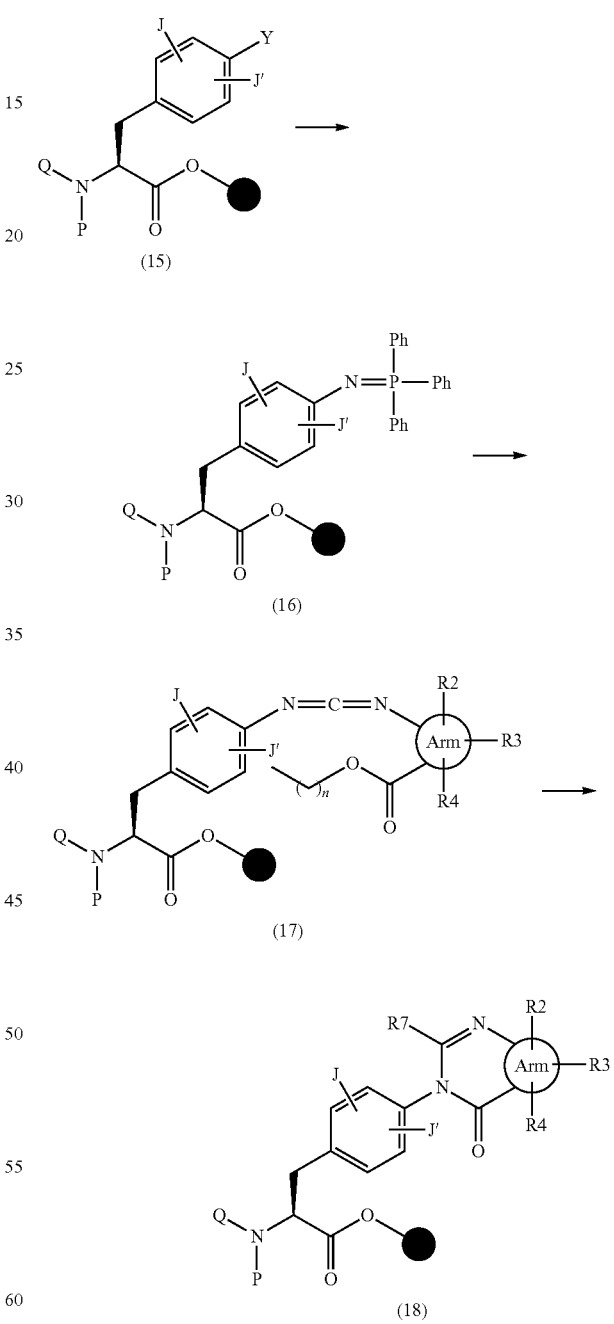

(15)

(16)

(17)

(18)

As the example of the methods for synthesizing an ester (45) wherein A represents the general formula (3), W is N and X is C(=O) in the general formula (1), the said ester can be obtained by reacting the amine (11) with a sodium nitrite in a solvent such as acetic acid.

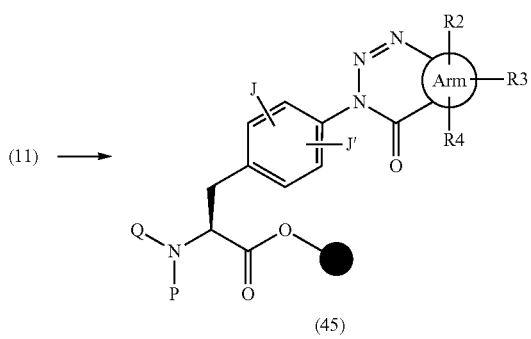

(45)

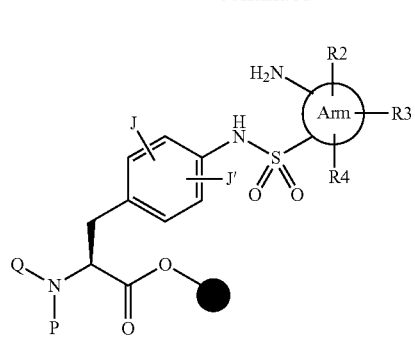

(48)

As the example of the methods for synthesizing an ester (46) wherein A represents the general formula (2), U is S(=O) and V is C(=O) in the general formula (1), the said ester can be obtained by reacting the amine (43) with, for example, a thionyl chloride in a solvent such as dichloromethane.

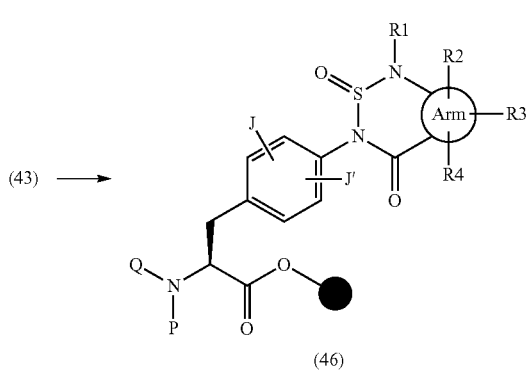

(43) → (46)

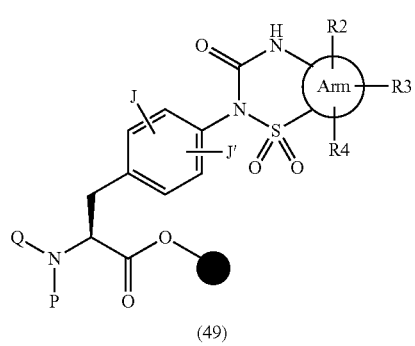

(49)

As the example of the methods for synthesizing an ester (50) wherein A represents the general formula (2), U is C(=O) and V is S(=O)$_2$ in the general formula (1), the said ester can be obtained by the following method. First, a sulfonamide (47) can be obtained by reacting the amine (6) with a sulfonyl chloride having a nitro group in the ortho position under the existence of a base such as 2,6-lutidine in a solvent such as NMP and dichloromethane. Then, an amine (48) is obtained by reducing a nitro group with SnCl$_2$ or hydrates thereof and cyclized by reagents such as CDI, triphosgene or p-nitrophenylchloroformate to obtain (49). Further, the alkyl halide is reacted thereto to obtain the said ester.

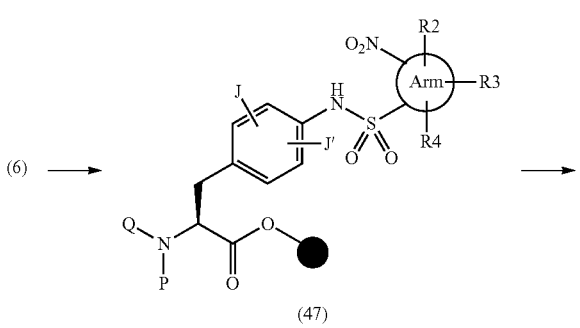

(6) → (47)

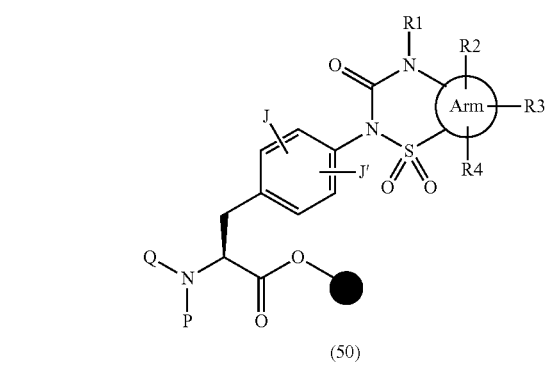

(50)

As the example of the methods for synthesizing an ester (54) wherein A represents the general formula (2), U and V are both C(=O) and R2, R3 or R4 is an amino group in the general formula (1), the said ester can be obtained by the following method. First, an amide (51) can be obtained by reacting the amine (6) with a carboxylic acid having a nitro group as a substituent(s) and an amino group in the ortho position, activated by using a condensing agent such as DIC and, if necessary, a suitable additive such as HOAt or HOBt in an organic solvent such as DMF, NMP or dichloromethane. Then, (52) is obtained by being cyclized by reagents such as CDI, triphosgene or p-nitrophenylchloroformate. After the reaction with alkyl halide, the amine (54) can be obtained by reducing a nitro group with SnCl$_2$, hydrates thereof or the like.

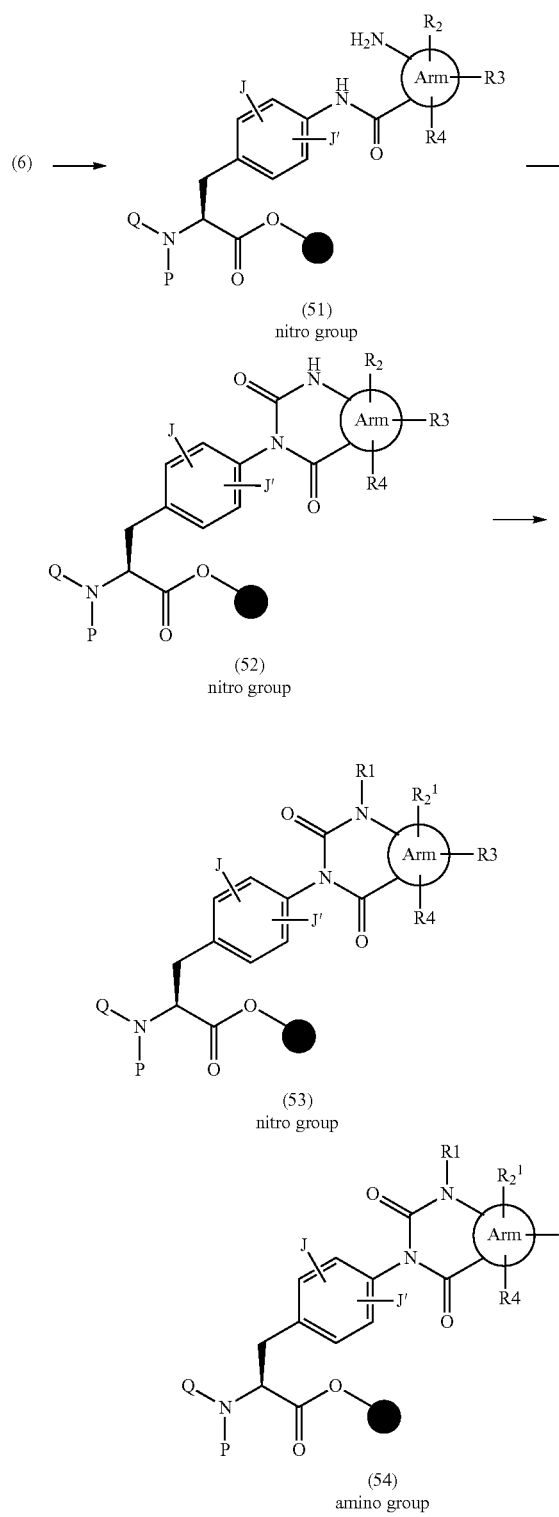

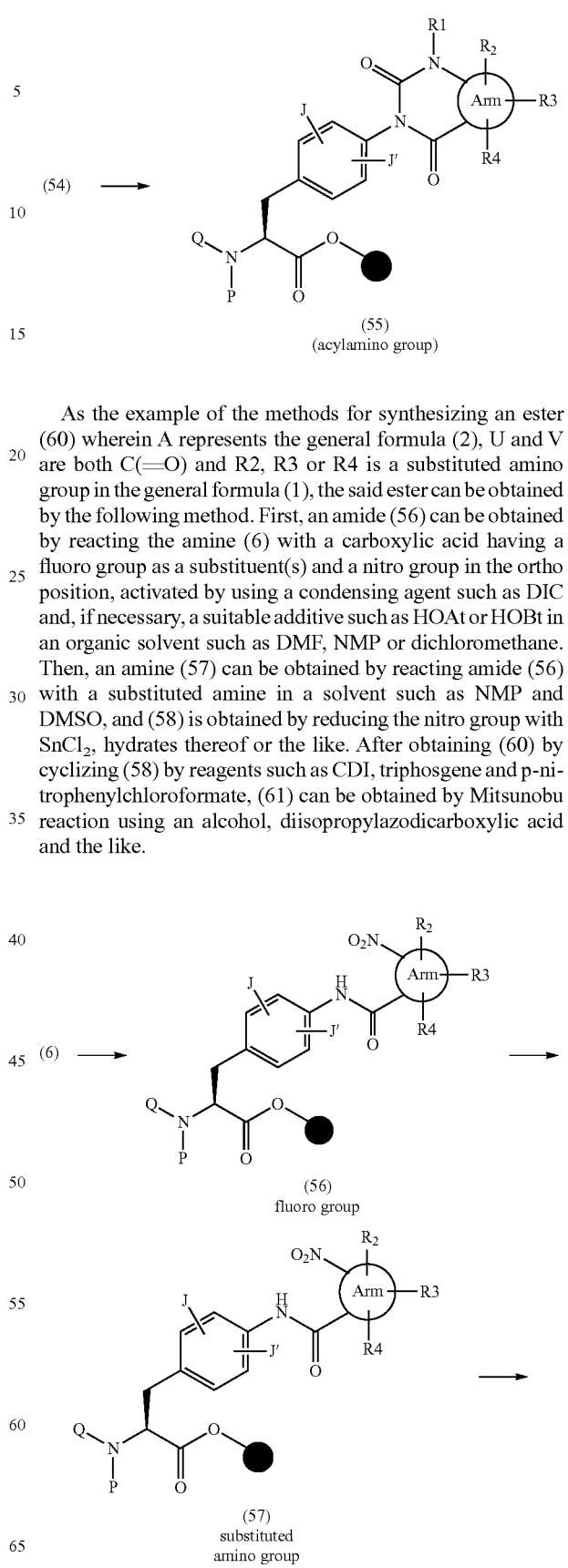

As the example of the methods for synthesizing an ester (54) wherein A represents the general formula (2), U and V are both C(=O) and R2, R3 or R4 is an acylamino group in the general formula (1), the said ester can be obtained by reacting (54) with acyl halide under the existence of a base such as pyridine in an organic solvent such as DMF, NMP and dichloromethane.

As the example of the methods for synthesizing an ester (60) wherein A represents the general formula (2), U and V are both C(=O) and R2, R3 or R4 is a substituted amino group in the general formula (1), the said ester can be obtained by the following method. First, an amide (56) can be obtained by reacting the amine (6) with a carboxylic acid having a fluoro group as a substituent(s) and a nitro group in the ortho position, activated by using a condensing agent such as DIC and, if necessary, a suitable additive such as HOAt or HOBt in an organic solvent such as DMF, NMP or dichloromethane. Then, an amine (57) can be obtained by reacting amide (56) with a substituted amine in a solvent such as NMP and DMSO, and (58) is obtained by reducing the nitro group with SnCl$_2$, hydrates thereof or the like. After obtaining (60) by cyclizing (58) by reagents such as CDI, triphosgene and p-nitrophenylchloroformate, (61) can be obtained by Mitsunobu reaction using an alcohol, diisopropylazodicarboxylic acid and the like.

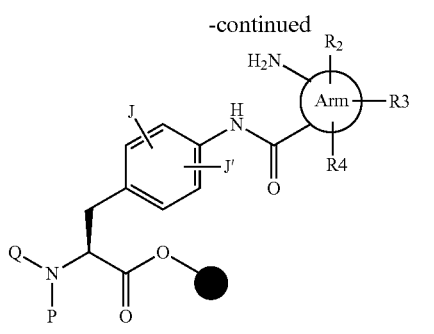

(58)
substituted
amino group

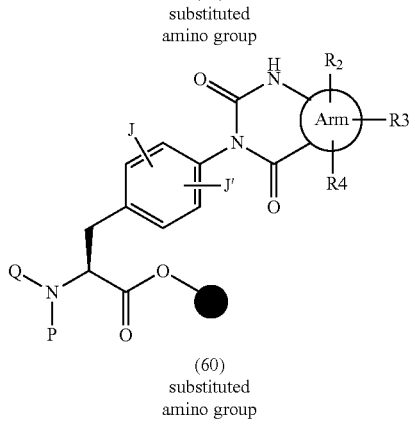

(60)
substituted
amino group

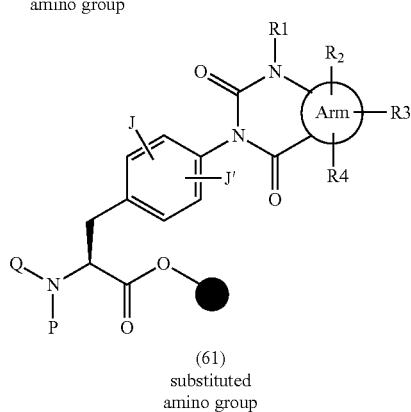

(61)
substituted
amino group

As the example of the methods for synthesizing an ester (62) wherein A represents the general formula (2), U and V are both C(=O) and R2, R3 or R4 is an ammonium group in the general formula (1), the said ester can be obtained by reacting (61) with alkyl halide under the existence of a base such as diisopropylethylamine in an organic solvent such as DMF and NMP.

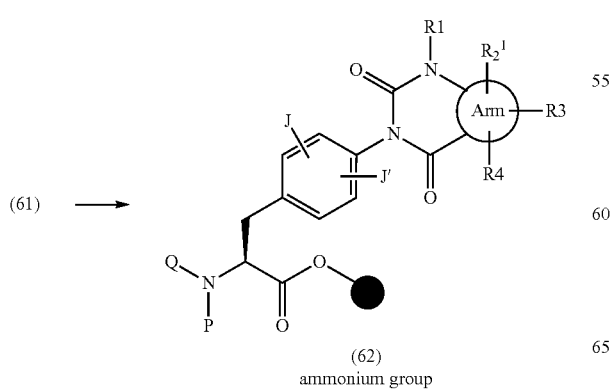

(62)
ammonium group

As the example of the methods for synthesizing an ester (68) wherein A represents the general formula (3-2) in the general formula (1), the said ester can be obtained by the following method. First, an amide (63) can be obtained by reacting the amine (6) with a carboxylic acid having an amino group protected with Fmoc in β-position activated by using a condensing agent such as DIC and, if necessary, a suitable additive such as HOAt or HOBt in an organic solvent such as DMF, NMP or dichloromethane. Then, an amine (64) can be obtained by removing Fmoc and then a sulfonamide (65) can be obtained by reacting (64) with a sulfonyl chloride having a nitro group as a substituent(s) under the existence of a base such as 2,6-lutidine in a solvent such as NMP and dichloromethane. Further, (66) can be obtained by reacting (65) with alkyl halide under the existence of a base such as diisopropylethylamine, and then an amine (67) can be obtained by reacting (66) with mercaptoethanol, diazabicycloundecene and so on. The compound is cyclized by reagents such as CDI, triphosgene and p-nitrophenylchloroformate to obtain the ester (68).

(6) ⟶

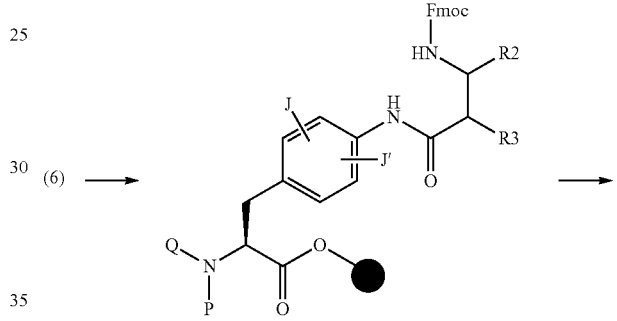

(63)

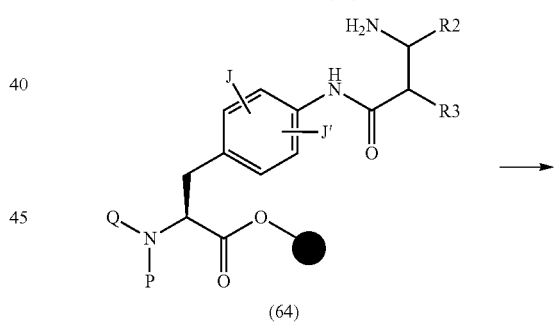

(64)

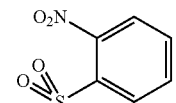

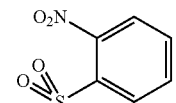

(65)

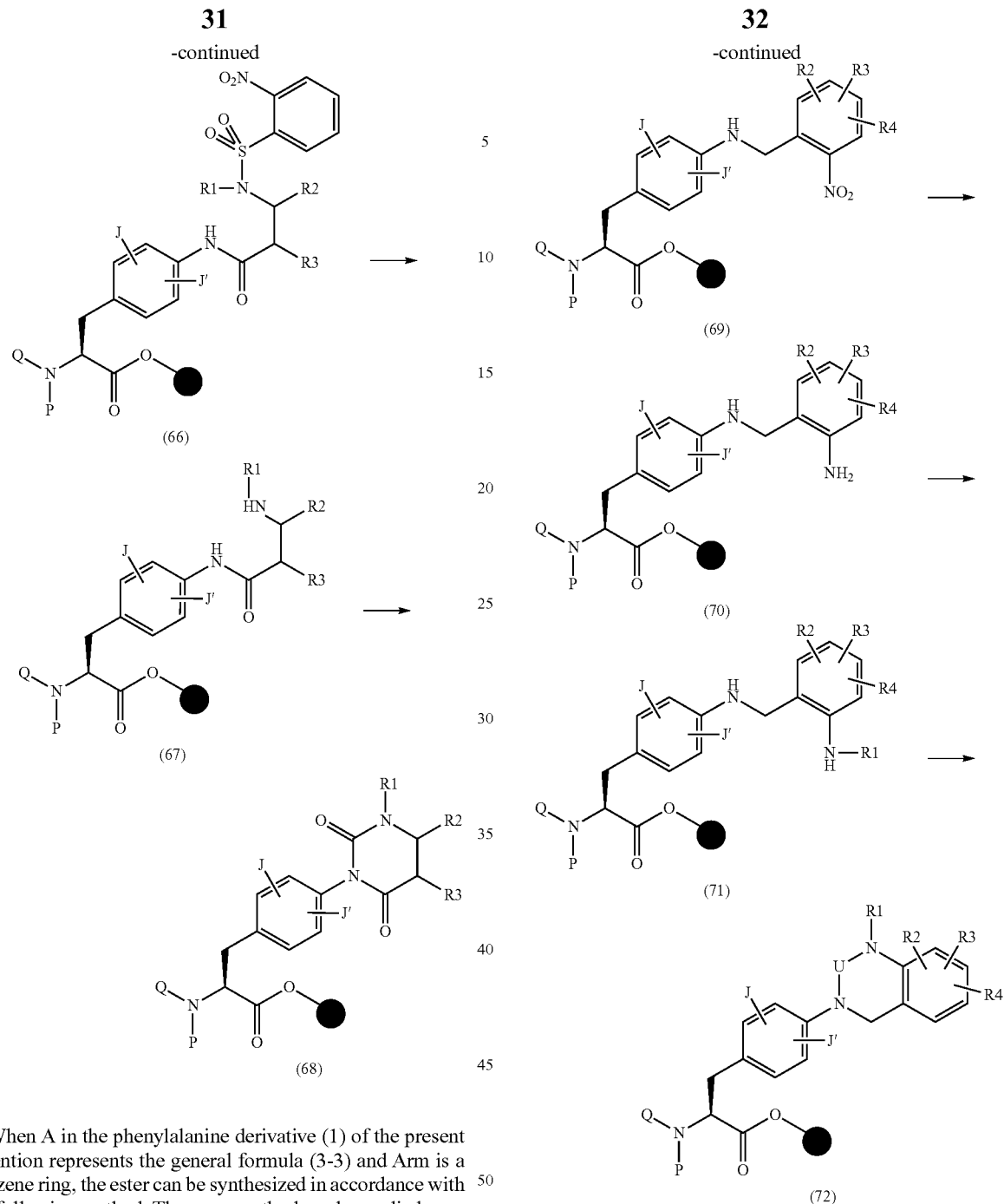
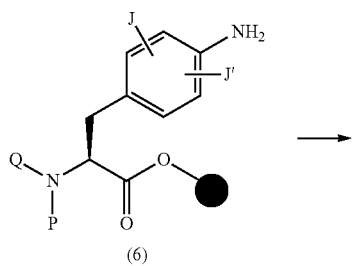

When A in the phenylalanine derivative (1) of the present invention represents the general formula (3-3) and Arm is a benzene ring, the ester can be synthesized in accordance with the following method. The same method can be applied even when Arm is other than a benzene ring.

First, the amine (6) is reacted with a halogenated methylbenzene having a nitro group in the ortho position to obtain a benzylamine (69). After the said benzylamine is reduced by tin chloride and the like to obtain an amine (70), an amine (71) can be obtained by converting the amine on the benzene ring of the introduced benzyl part into mono R1 substituted group by various methods. An ester (72) can be obtained by being finally cyclized by reagents such as CDI, triphosgene and p-nitrophenylchloroformate.

D-T part in the general formula (1) can be constructed as follows. For example, when T is C(═O) and B is a hydroxyl group in the formula (1), if, in the ester (19), the substituent G has C structure, the substituent(s) which can be converted into C in a certain point of the synthesizing process or the substituent(s) which have suitably protected structure, then the substituent Z has the structure of (2), (3), (3-1), (3-2) or the substituent(s) which can be converted into A in a certain point of the synthesizing process or the substituent(s) has suitably protected structure, the ester (19) can be converted in the amine (20) by removing a protective group(s) under suitable conditions depending on the protective group E. For instance, when Fmoc group (9-fluorenylmethoxycarbonyl group) is used as E, the protective groups can be removed with a base such as piperidine in a solvent such as DMF. The amine (20) can be converted into the amide (21) by condensing carboxylic acid by using a condensing agent such as DIC and, if necessary, a suitable additive such as HOAt or HOBt in an organic solvent such as DMF, NMP and dichloromethane.

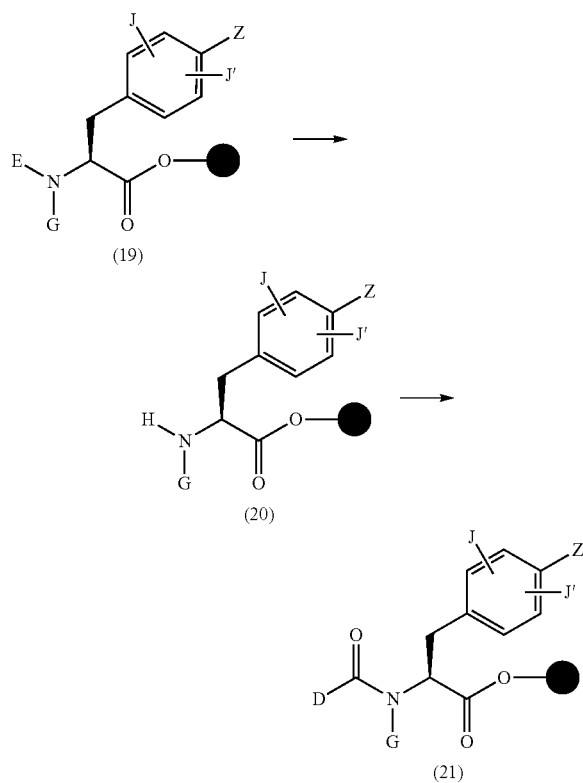

Further, the amine (20) is reacted with acyl halide, carboxylic anhydride, sulfonyl halide and sulfonyl anhydride under the existence of an organic base such as triethylamine, diisopropylethylamine, pyridine and N,N-dimethylaminopyridine or an inorganic base such as potassium carbonate and sodium carbonate in an organic solvent such as DMF, NMP and dichloromethane and then can form the corresponding amide structure and sulfonamide acid structure.

Further, the amine (20) is reacted with various isocyanate and isothiocyanate under the existence of an organic base, if necessary, such as triethylamine, diisopropylethylamine, pyridine and N,N-dimethylaminopyridine in an organic solvent such as DMF, toluene and dichloromethane and then can form the corresponding urea structure and thiourea structure.

The esters synthesized by the above-described methods such as (9), (12), (13), (14), (18), (21), (44), (45), (46), (50), (54), (55), (61), (62), (68) and (72) are cleaved from a resin under suitable conditions to obtain a carboxylic acid (87). For example, when Wang resin is used, if, in the ester (22), each of A1, C1 and D1 is A, C, and D respectively or a group which is converted in A, C, and D respectively under the cleavage condition, the ester (22) is treated with an acidic solution including such as TFA (trifluoroacetic acid) thereto to obtain a solution of the carboxylic acid (87). Further, the pure carboxylic acid (87) can be obtained by applying well-known isolating and purification methods such as concentration, extraction, crystallization, column chromatography, HPLC and recrystallization to the thus-obtained carboxylic acid (87).

The compound wherein B represents a lower alkoxyl group in the general formula (1) can be obtained by condensing the carboxylic acid (87) with a suitable lower alcohol under the existence of a suitable condensing agent or acid catalyst.

The compound wherein B represents a hydroxylamino group in the general formula (1) can be obtained by condensing the carboxylic acid (87) with a hydroxylamine under the existence of a suitable condensing agent.

The phenylalanine derivative (1) can be synthesized by applying solid phase methods shown above to solution phase methods, by selecting a suitable protective group and using well-known isolating and purification methods.

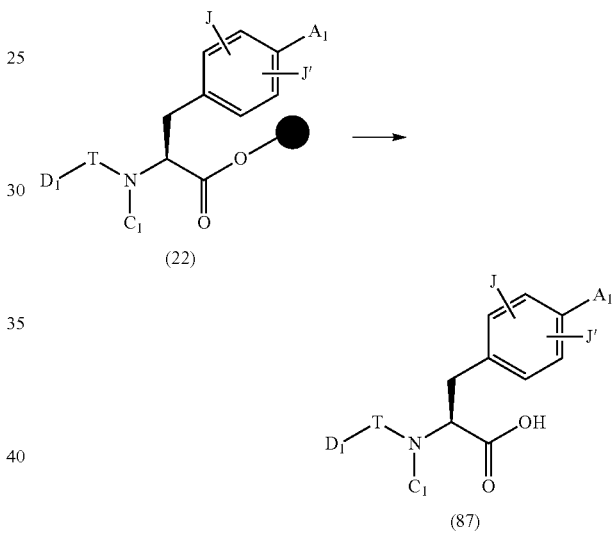

When the compounds of general formula (1) can form salts thereof, it is sufficient for the salts to be pharmaceutically acceptable ones. When the compound has an acidic group such as carboxyl group, the salts can be ammonium salts, or salts thereof with alkali metals, e.g. sodium and potassium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compound has a basic group, the salts can be those with inorganic acids, e.g. hydrochloric acid, sulfuric acid and phosphoric acid; those with organic acids, e.g. acetic acid, citric acid, benzoic acid, maleic acid, fumaric acid, tartaric acid and succinic acid; and those with organosulfonic acids, e.g. methanesulfonic acid and p-toluenesulfonic acid. The salts can be formed by mixing a compound of the general formula (1) with a necessitated acid or base in a proper ratio in a solvent or dispersant or by the cation exchange or anion exchange reaction with another salt.

The compounds of the general formula (1) of the present invention include also solvates thereof such as hydrates and alcohol adducts thereof.

The compounds of general formula (1) and salts thereof are administered as they are or in the form of various pharmaceutical compositions to patients. The dosage forms of the pharmaceutical compositions are, for example, tablets, powders, pills, granules, capsules, suppositories, solutions, sugar-coated tablets, depots and syrups. They can be prepared with ordinary preparation assistants by an ordinary method.

For example, the tablets are prepared by mixing the phenylalanine derivative, the active ingredient of the present invention, with any of known adjuncts such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; flavour, e.g. peppermint, Akamono (Gaultheria aderothrix) Oil and cherry; lubricants, e.g. magnesium stearate, talc and carboxymethyl cellulose; excipients for soft gelatin capsules and suppositories, e.g. fats, waxes, semi-solid or liquid polyols, natural oils and hardened oils; and excipients for solutions, e.g. water, alcohols, glycerols, polyols, sucrose, invert sugars, glucose and vegetable oils.

The antagonist containing a compound(s) of above general formula (1) or a salt(s) thereof as active ingredient is usable as a therapeutic agent or preventing agent for diseases in which α4 integrin-depending adhesion process participates in the pathology, such as inflammatory diseases, rheumatoid arthritis, inflammatory bowel diseases, systemic lupus erythematosus, multiple sclerosis, Sjö gren's syndrome, asthma, psoriasis, allergy, diabetes, cardiovascular diseases, arterial sclerosis, restenosis, tumor proliferation, tumor metastasis, transplantation rejection, etc.

The dose of the compound of general formula (1) or salt thereof used for the above-described purpose varies depending on the intended therapeutic effect, administration method, period of the treatment, and age and body weight of the patient. The dose is usually 1 µg to 5 g a day for adults in the oral administration, and 0.01 µg to 1 g a day for adults in the parenteral administration.

EXAMPLES

The following Examples will further illustrate the present invention, which are only preferred embodiments of the invention and which by no means limit the invention.

Example 1

Synthesis of the Compound of the Following General Formula (23) which has a Substituent(s) of Example 1 of Table 1

Process 1 Preparation of Resin

Fmoc-Phe(4-nitro)-OH (2.5 g), 2,6-dichlorobenzoyl chloride (0.745 mL) and pyridine (1.5 mL) in a solution of NMP (25 mL) were added to Wang resin (0.76 mmol/g, 2.3 g) and stirred at room temperature for 16 hours. After removing the excess solvent, the resin was washed with DMF three times, dichloromethane three times and NMP twice. In order to conduct capping of an unreacted hydroxyl group on the resin, the resin was treated with acetic anhydride (20 mL), pyridine (20 mL) and NMP (20 mL) for 2 hours. After removing the excess solvent, the resin was washed with DMF three times and dichloromethane three times, and dried under reduced pressure.

Process 2 Removal of Fmoc Group

A DMF solution of 20% piperidine (25 mL) was added to the resin obtained in Process 1 and reacted for 15 minutes. After removing the solvent, the resin was washed with DMF and dichloromethane three times each, and dried under reduced pressure.

Process 3 Acylation Reaction 2,6-dichlorobenzoyl chloride (1.1 mL), 2,6-lutidine (1.6 mL) and NMP (26 mL) were added to 2.0 g of the resin obtained in Process 2 and reacted for 6 hours. After removing the excess solvent, the resin was washed with DMF and dichloromethane three times each, and dried under reduced pressure.

Process 4 Reduction of Nitro Group

NMP (30 mL).EtOH (1.5 mL) solution of $SnCl_2.2H_2O$ (15.0 g) was added to 1.5 g of the resin obtained in Process 3 and reacted for 16 hours. After removing the reaction solvent, the resin was washed with DMF and dichloromethane three times each.

Process 5 Construction of quinazoline-2,4-dione Ring 2 g of the resin obtained in Process 4 was reacted in NMP solution (32 mL) of methyl 2-isocyanatebenzoate (1.92 g) for 16 hours. After removing the reaction solvent, the resin was washed with DMF and dichloromethane three times each. DMF solution of 20% piperidine was added to the resin for 1 hour. After removing the reaction solvent, the resin was washed with DMF and dichloromethane three times each and dried under reduced pressure.

Process 6 Alkylation

Methyl iodide (0.75 mmol), 18-crown-6 (30 mg), NMP (1 mL) and K2CO3 (35 mg) were added to 20 mg of the resin obtained in Process 5 and reacted for 3 days. After removing the reaction solvent, the resin was washed with DMF, water, DMF and dichloromethane three times each and dried under reduced pressure.

Process 7 Cleavage from Resin

The resin obtained in Process 6 was treated with trifluoroacetic acid containing 5% of water for 1 hour. After filtration, the filtrate was concentrated under reduced pressure. The residue was purified with high-pressure liquid chromatography (water/acetonitrile) to obtain 8 mg of the intended compound.

MS (ESI MH+): 512

CHNO: C25H19Cl2N3O5

Examples 2 to 7

The compounds described below were synthesized by the same procedure as that of Example 1 except that corresponding alkylation reagents were used in Process 6 of Example 1. Meanwhile, R in Table 1 is a substituent(s) in the following general formula (23) and the same procedure as that of Example 1 was repeated in Example 2 except that Process 6 of Example 1 was not carried out.

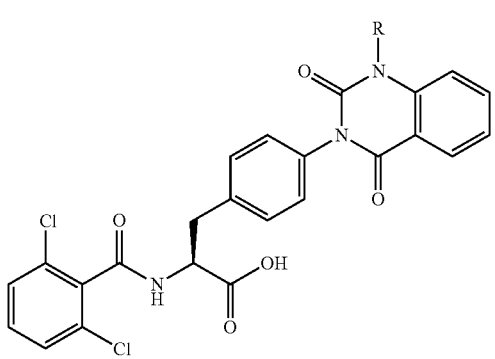

(23)

(24)

TABLE 1

| Example | R— | MS Found (MH+) |
|---|---|---|
| 1 | Me— | 512 |
| 2 | H— | 498 |
| 3 | Et— | 526 |
| 4 | 2,6-difluorobenzyl | 624 |
| 5 | 4-(1-pyrrolidino)benzenecarbonylmethyl | 685 |
| 6 | NCCH2— | 537 |
| 7 | HOC(=O)CH2— | 556 |

TABLE 2

| Example | R— | MS Found (MH+) |
|---|---|---|
| 8 | 2,6-dimethylbenzoyl | 472 |
| 9 | 2,6-dimethoxybenzoyl | 504 |
| 10 | 2-ethoxybenzoyl | 488 |
| 11 | 3,4-dimethoxycinnamyl | 530 |
| 12 | cyclohexylcarbonyl | 450 |
| 13 | trans-4-carboxycyclohexanecarbonyl | 494 |

Example 8

Synthesis of the Compound of the Following General Formula (24) which has a Substituent(s) of Example 8 of Table 2

Process 1 Construction of quinazoline-2,4-dione Ring and Removal of Fmoc Group

A nitro group of the resin (1 g) obtained in Process 1 of Example 1 was reduced in accordance with Process 4 of Example 1, and quinazoline-2,4-dione ring was constructed and Fmoc group was removed in accordance with Process 5 of Example 1.

Process 2 Acylation, Alkylation, and Cleavage from Resin

Acylation was conducted by using the resin obtained in Process 1 of Example 8 (25 mg), 2,6-dimethyl benzoic acid (0.4 mmol), DIC (0.4 mmol), HOAt (0.4 mmol) and NMP (2 mL). Then, alkylation was conducted in accordance with Process 6 of Example 1 and cleavage from resin and purification was performed by the same process as Process 7 of Example 1 to obtain the intended compound (9 mg).
MS (ESI MH+): 472
CHNO: C27H25N3O5

Examples 9 to 13

The compounds described below were synthesized by the same procedure as that of Example 8 except that corresponding carboxylic acid was used in Process 2 of Example 8. R in Table 2 is a substituent(s) in the following general formula (24). Further, twice as much as DIC and HOAt used in Process 2 of Example 8 were used in Example 13, to obtain the intended compound (7 mg).

Example 14

Synthesis of the Compound of the Following General Formula (25) which has a Substituent(s) of Example 14 of Table 3

Process 1 Construction of quinazoline-2-thioxo-4-one Ring

The resin obtained in Process 4 of Example 1 (2.00 g) was reacted in NMP solution (25 mL) of methyl 2-isothiocyanatebenzoate (1.40 g) for 16 hours. After removing the reaction solvent, the resin was washed with DMF and dichloromethane three times each and dried under reduced pressure.

Process 2 Cleavage from Resin

The resin obtained in Process 1 (25 mg) was treated in accordance with Process 7 of Example 1 to obtain the intended compound (10 mg).
MS (ESI MH+): 513
CHNO: C24H17Cl2N3O4S

Example 15

Synthesis of the Compound of the Following General Formula (25) which has a Substituent(s) of Example 15 of Table 3

Process 1 Acylation

Acylation was conducted by using the resin obtained in Process 2 of Example 1 (25 mg), 2,6-dimethylbenzoic acid (0.4 mmol), DIC (0.4 mmol), HOAt (0.4 mmol) and NMP (2 mL).

Process 2 Construction of quinazoline-2-thioxo-4-one Ring

The resin obtained in Process 1 (2.00 g) was reacted in NMP solution (25 mL) of methyl 2-isothiocyanatebenzoate (1.40 g) for 16 hours. After removing the reaction solvent, the resin was washed with DMF and dichloromethane three times each and dried under reduced pressure.

Process 3 Cleavage from Resin

The resin obtained in Process 1 (25 mg) was treated in accordance with Process 7 of Example 1 to obtain the intended compound (8 mg).
MS (ESI MH+): 474
CHNO: C26H23N3O4S

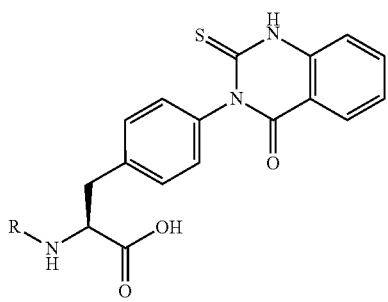

(25)

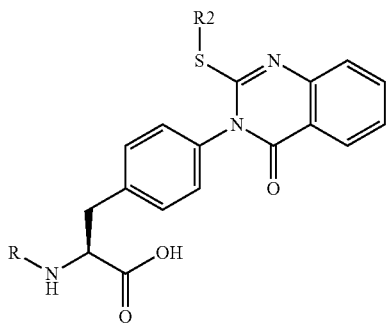

(26)

TABLE 4

| Example | R1— | R2— | MS Found (MH+) |
|---|---|---|---|
| 16 | 2,6-dichlorobenzoyl | allyl | 554 |
| 17 | 2,6-dichlorobenzoyl | ethyl | 542 |
| 18 | 2,6-dichlorobenzoyl | methyl | 528 |
| 19 | 2,6-dichlorobenzoyl | isoamyl | 584 |
| 20 | 2,6-dichlorobenzoyl | 2,6-difluorobenzyl | 640 |
| 21 | 2,6-dichlorobenzoyl | 2-methylbenzyl | 618 |
| 22 | 2,6-dichlorobenzoyl | 1-phenylethyl | 618 |
| 23 | 2,6-dichlorobenzoyl | 4-methoxyphenacyl | 662 |
| 24 | 2,6-dimethylbenzoyl | methyl | 488 |
| 25 | 2,6-dimethylbenzoyl | ethyl | 502 |
| 26 | 2,6-dimethylbenzoyl | allyl | 514 |
| 27 | 2,6-dimethylbenzoyl | isoamyl | 544 |
| 28 | 2,6-dimethylbenzoyl | 2,6-difluorobenzyl | 600 |
| 29 | 2,6-dimethylbenzoyl | 2-methylbenzyl | 578 |
| 30 | 2,6-dimethylbenzoyl | 1-phenylethyl | 578 |

TABLE 3

| Example | R— | MS Found (MH+) |
|---|---|---|
| 14 | 2,6-dichlorobenzoyl | 513 |
| 15 | 2,6-dimethylbenzoyl | 474 |

Example 16

Synthesis of the Compound of the Following General Formula (26) which has a Substituent(s) of Example 16 of Table 4

Process 1 Alkylation

Allylbromide (0.5 mmol), diisopropylethylamine (1.0 mmol) and NMP (2 mL) were added to the resin obtained in Process 1 of Example 14 (25 mg) and reacted for 16 hours. After removing the reaction solvent, the resin was washed with DMF and dichloromethane three times each and dried under reduced pressure.

Process 2 Cleavage from Resin

The resin obtained in Process 1 was treated in accordance with Process 7 of Example 1 to obtain the intended compound (6 mg).
MS (ESI MH+): 554
CHNO: C27H21Cl2N3O4S Examples 17 to 30

The compounds shown in Table 4 were synthesized by the same procedure as that of Example 16 except that the resin obtained in Process 1 of Example 14 or Process 2 of Example 15 was used and the corresponding halide was used in Process 1 of Example 16. Meanwhile, R1 and R2 in Table 4 are a substituent(s) in the following general formula (26).

NMR data of the compound of Example 18: $^1$H-NMR (CDCl$_3$) δ=2.53 (3H, s), 3.40 (2H, t, J=5.3 Hz), 5.20 (1H, t, J=5.3 Hz), 7.21-7.35 (6H, m), 7.41 (1H, t, J=7.5 Hz), 7.50 (2H, d, J=8.7 Hz), 7.65 (1H, d, J=8.4 Hz), 7.76 (1H, t, Hz), 8.19 (1H, d, J=7.5 Hz)

Example 31

Synthesis of the Compound of the Following General Formula (27) which has a Substituent(s) of Example 31 of Table 5

Process 1 Acylation 2-nitrobenzoylchloride (4 mmol), 2,6-lutidine (8 mmol) and NMP were added to the resin obtained in Process 4 of Example 1 (1.00 g) and stirred for 16 hours. After that, the resin was washed with DMF and dichloromethane three times each and dried under reduced pressure.

Process 2 Reduction of Nitro Group

The resin obtained in Process 1 (25 mg) was treated in accordance with Process 4 of Example 1 to obtain the intended resin.

Process 3 Cyclization by Ortho Ester and Cleavage from Resin

Trimethylorthoacetate (1 mL), AcOH (50 μL) and NMP (1 mL) were added to the resin obtained in Process 2 (25 mg) and stirred at 50° C. for 16 hours. After washing it with DMF and dichloromethane three times each and drying under reduced pressure, the resin was treated in accordance with Process 7 of Example 1 to obtain the intended compound (8 mg).

MS (ESI MH+): 496
CHNO: C25H19Cl2N3O

Examples 32 to 44

The compounds shown in Table 5 were synthesized by the same procedure as that of Example 31 except that the resin obtained in Process 4 of Example 1 or Process 1 of Example 15 was used in Process 1 of Example 31 and the corresponding ortho ester was used in Process 3 of Example 31. Meanwhile, R1 and R2 in Table 5 are a substituent(s) in the following general formula (27).

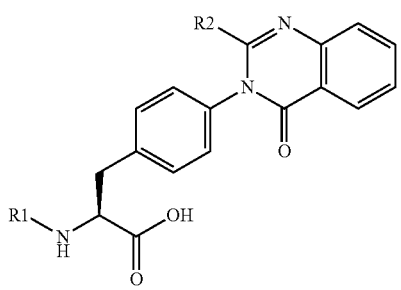

(27)

TABLE 5

| Example | R1— | R2— | MS Found (MH+) |
|---|---|---|---|
| 31 | 2,6-dichlorobenzoyl | methyl | 496 |
| 32 | 2,6-dichlorobenzoyl | ethyl | 510 |
| 33 | 2,6-dichlorobenzoyl | n-propyl | 524 |
| 34 | 2,6-dichlorobenzoyl | n-butyl | 538 |
| 35 | 2,6-dichlorobenzoyl | phenyl | 558 |
| 36 | 2,6-dichlorobenzoyl | methoxy | 512 |
| 37 | 2,6-dichlorobenzoyl | ethoxy | 526 |
| 38 | 2,6-dichlorobenzoyl | chloromethyl | 530 |
| 39 | 2,6-dimethylbenzoyl | methyl | 456 |
| 40 | 2,6-dimethylbenzoyl | n-propyl | 484 |
| 41 | 2,6-dimethylbenzoyl | n-butyl | 498 |
| 42 | 2,6-dimethylbenzoyl | phenyl | 518 |
| 43 | 2,6-dimethylbenzoyl | ethoxy | 486 |
| 44 | 2,6-dimethylbenzoyl | chloromethyl | 490 |

NMR data of the compound of Example 32: $^1$H-NMR (CDCl$_3$) δ=1.21 (3H, t, J=7.4 Hz), 2.47 (2H, q, J=7.4 Hz), 3.32-3.42 (2H, m), 5.19 (1H, t, J=5.4 Hz), 7.10-7.20 (2H, m), 7.22-7.35 (4H, m), 7.43-7.54 (3H, m), 7.70-7.83 (2H, m), 8.21 (1H, d, J=7.8 Hz)

Example 45

Synthesis of the Compound of the Following General Formula (28) which has a Substituent(s) of Example 45 of Table 6

Process 1 Acylation 3-chloro-2-nitrobenzoic acid (210 mg, 1.04 mmol), HOAt (141 mg, 1.04 mmol), DIC (161 uL, 1.04 mmol) and NMP (2 mL) were added to the resin obtained in Process 4 of Example 1 (200 mg) and stirred for 64 hours. After that, the resin was washed with DMF and dichloromethane three times each and dried under reduced pressure.

Process 2 Reduction of Nitro Group

The resin obtained in Process 1 was treated in accordance with Process 4 of Example 1.

Process 3 Construction of quinazoline-2,4-dione Ring

Carbonyldiimidazole (844 mg, 5.21 mmol) and NMP (2 mL) were added to the resin obtained in Process 2 and stirred at 80° C. for 16 hours. After washing it with DMF and dichloromethane three times each and drying under reduced pressure, the resin was treated in accordance with Process 7 of Example 1 to obtain the intended compound.

MS (ESI MH+): 532
CHNO: C24H16Cl3N3O5

Examples 46 to 54

The compounds shown in Table 6 were synthesized by the same procedure as that of Example 45 except that respective corresponding substituted 2-nitrobenzoic acid was used in Process 1 of Example 45. Meanwhile, R1, R2, R3 and R4 in Table 6 are a substituent(s) in the following general formula (28).

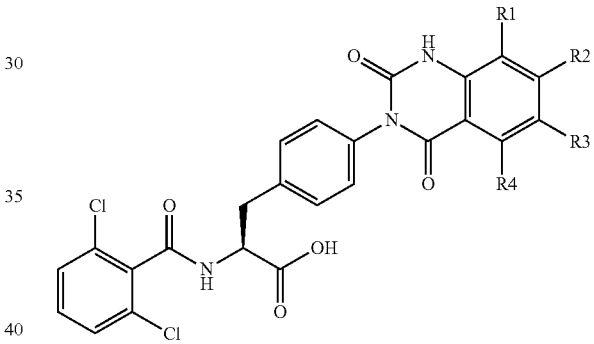

(28)

TABLE 6

| Example | R1— | R2— | R3 | R4 | MS Found (MH+) |
|---|---|---|---|---|---|
| 45 | chloro | H— | H— | H— | 532 |
| 46 | methoxy | H— | H— | H— | 528 |
| 47 | H— | H— | chloro | H— | 532 |
| 48 | H— | H— | methoxy | H— | 528 |
| 49 | H— | trifluoromethyl | H | H— | 566 |
| 50 | methyl | H— | H— | H— | 512 |
| 51 | H— | methoxy | methoxy | H— | 558 |
| 52 | H— | H— | fluoro | H— | 516 |
| 53 | H— | H— | H— | methyl | 512 |
| 54 | H— | H— | H— | chloro | 532 |

Example 57

Synthesis of the Compound of the Following General Formula (29) which has a Substituent(s) of Example 57 of Table 7

Process 1 Acylation 2-fluoro-5-nitrobenzoic acid (1.63 g, 8.81 mmol), HOAt (1.2 g, 8.81 mmol), DIC (675 uL, 4.36 mmol) and NMP (25 mL) were added to the resin obtained in Process 4 of Example 1 (1 g) and stirred for 14 hours. After that, the resin was washed with DMF and dichloromethane three times each and dried under reduced pressure.

Process 2 Substitution of Fluoro Group with Amine

Isopropylamine (400 uL) and NMP (2 mL) were added to the resin obtained in Process 1 (200 mg) and stirred for 21 hours. After that, the resin was washed with DMF and dichloromethane three times each and dried under reduced pressure.

Process 3 Construction of quinazoline-2,4-dione Ring

Carbonyldiimidazole (200 mg) and trans-decahydronaphthalene (2 mL) were added to the resin obtained in Process 2 and stirred at 95° C. for 15 hours. After washing it with DMF, methanol and dichloromethane three times each and drying under reduced pressure, the resin was treated in accordance with Process 7 of Example 1 to obtain the intended compound.

MS (ESI MH+): 585
CHNO: C27H22Cl2N4O7

Examples 58 to 65

The compounds shown in Table 7 were synthesized by the same procedure as that of Example 57 except that respective corresponding amine was used in Process 2 of Example 57. Meanwhile, R in Table 7 is a substituent in the following general formula (29).

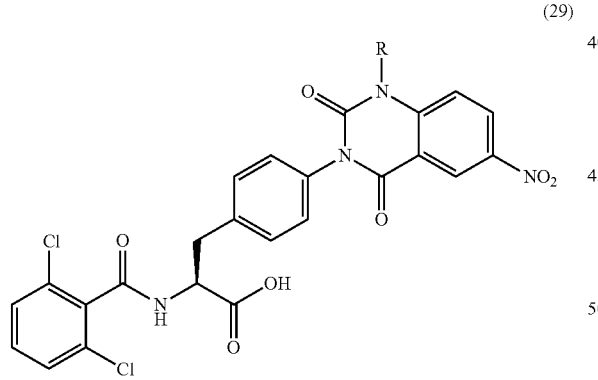

(29)

TABLE 7

| Example | R— | MS Found (MH+) |
|---|---|---|
| 57 | isopropyl | 585 |
| 58 | sec-butyl | 599 |
| 59 | cyclobutyl | 597 |
| 60 | cyclopentyl | 611 |
| 61 | isobutyl | 599 |
| 62 | cyclohexylmethyl | 639 |
| 63 | methyl | 557 |
| 69 | cyclopropyl | 583 |
| 65 | benzyl | 633 |

Example 66

Synthesis of the Compound of the Following General Formula (30) which has a Substituent of Example 66 of Table 8

Process 1 Substitution of Fluoro Group with Amine

THF solution of 2.0M methylamine (3 mL) and NMP (2 mL) were added to the resin obtained in Process 1 of Example 57 (150 mg) and stirred for 14 hours. After that, the resin was washed with DMF and dichloromethane three times each and dried under reduced pressure.

Process 2 Construction of quinazoline-2-thioxo-4-one

Thiocarbonyldiimidazole (200 mg) and trans-decahydronaphthalene (2 mL) were added to the resin obtained in Process 1 and stirred at 95° C. for 15 hours. After washing it with DMF, methanol and dichloromethane three times each and drying under reduced pressure, the resin was treated in accordance with Process 7 of Example 1 to obtain the intended compound.

MS (ESI MH+): 573
CHNO: C25H18Cl2N4O6S

Examples 67 to 69

The compounds shown in Table B were synthesized by the same procedure as that of Example 66 except that respective corresponding amine was used in Process 1 of Example 66. Meanwhile, R1 in Table B is a substituent in the following general formula (30).

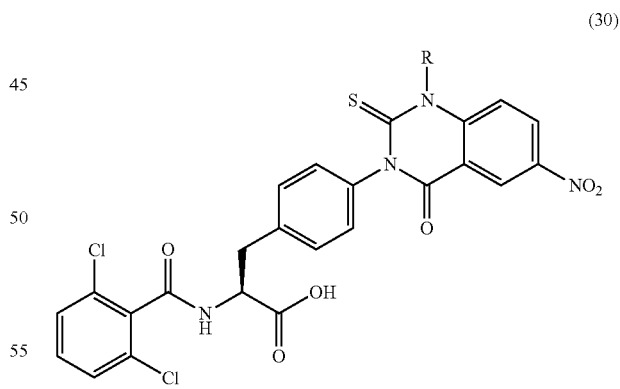

(30)

TABLE 8

| Example | R— | MS Found (MH+) |
|---|---|---|
| 66 | methyl | 573 |
| 67 | ethyl | 587 |
| 68 | cyclopropyl | 599 |
| 69 | benzyl | 649 |

Example 70

Synthesis of the Compound of the Following General Formula (31) which has Substituents of Example 70 of Table 9

Process 1 Acylation 2-amino-3,6-dichlorobenzoic acid (845 mg, 4.10 mmol), HOAt (558 g, 4.10 mmol), DIC (317 uL, 2.05 mmol) and NMP (11.5 mL) were added to the resin obtained in Process 4 of Example 1 (500 mg) and stirred for 24 hours. After that, the resin was washed with DMF, methanol and dichloromethane three times each and dried under reduced pressure.

Process 2 Construction of quinazoline-2,4-dione Ring

Carbonyldiimidazole (200 mg) and trans-decahydronaphthalene (2 mL) were added to the resin obtained in Process 1 (200 mg) and stirred at 95° C. for 15 hours. After that the resin was washed with DMF, methanol and dichloromethane three times each and dried under reduced pressure.

Process 3 Alkylation

The resin obtained in Process 2 was alkylated in accordance with Process 6 of Example 1.

Process 4 Cleavage from Resin

The intended compound was obtained by being treated in accordance with Process 7 of Example 1.

MS (ESI MH+): 580
CHNO: C25H17Cl4N3O5

Examples 71 to 80

The compounds of Examples 71 to 75 were synthesized by the same procedure as that of Example 70 except that respective corresponding benzoic acid derivatives were used in Process 1 of Example 70. The same procedure as that of Example 70 was repeated in Examples 76 to 80 except that alkylation in Process 3 of Example 70 was not conducted. Meanwhile, R in Table 9 is substituents in the following general formula (31).

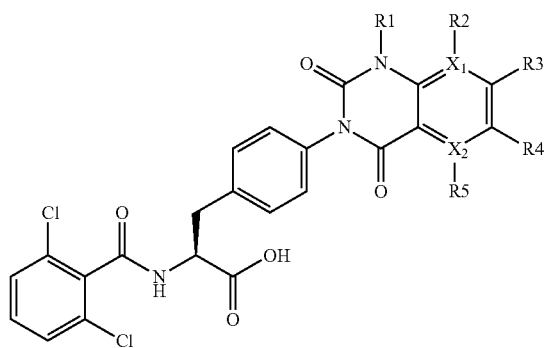

(31)

TABLE 9

| Example | R1— | R2— | R3— | R4— | R5— | X1 | X2 | MS Found (MH+) |
|---|---|---|---|---|---|---|---|---|
| 70 | methyl | chloro | H | H | chloro | C | C | 580 |
| 71 | methyl | chloro | H | chloro | H | C | C | 580 |
| 72 | methyl | H | fluoro | H | H | C | C | 530 |
| 73 | methyl | H | H | Br | H | C | C | 591 |
| 74 | methyl | — | H | H | H | N | C | 513 |
| 75 | methyl | — | H | H | — | N | N | 514 |
| 76 | H | chloro | H | H | chloro | C | C | 566 |
| 77 | H | chloro | H | chloro | H | C | C | 566 |
| 78 | H | H | fluoro | H | H | C | C | 516 |
| 79 | H | — | H | H | H | N | C | 499 |
| 80 | H | — | H | H | — | N | N | 500 |

Example 81

Synthesis of the Compound of the Following General Formula (32) which has Substituents of Example 81 of Table 10

Process 1 Acylation

The resin obtained in Process 4 of Example 1 was acylated in accordance with Process 1 of Example 70.

Process 2 Construction of Triazene Ring

Sodium nitrite (150 mg) and acetic acid (4.5 ml) were added to the resin obtained in Process 1 (90 mg) and stirred for 24 hours. After washing it with DMF, methanol and dichloromethane three times each and drying under reduced pressure, the intended compound was obtained by being treated in accordance with Process 7 of Example 1.

MS (ESI MH+): 551
CHNO: C23H14Cl4N4O4

Examples 82 and 83

The compounds of Examples 82 and 83 shown in Table 10 were synthesized by the same procedure as that of Example 81 except that respective corresponding 2-aminobenzoic acid was used in Process 1 of Example 81. Meanwhile, R1, R2, R3 and R4 in Table 10 are substituents in the following general formula (32).

Example 84

Synthesis of the Compound of the Following General Formula (32) which has Substituents of Example 84 of Table 10

Process 1 Acylation, Reduction of Nitro Group

Acylation was conducted by using the resin obtained in Process 4 of Example 1 (1 g), 5-methoxy-2-nitrogenzoic acid (1.62 g, 8.21 mmol), DIC (635 uL, 4.11 mmol), HOAt (1.12 g, 8.21 mmol) and NMP (23 mL). Then, the nitro group was reduced in accordance with Process 2 of Example 31.

Process 2 Construction of Triazene Ring, Cleavage from Resin

The resin obtained in Process 1 was treated in accordance with Process 2 of Example 81 and then treated in accordance with Process 7 of Example 1 to obtain the intended compound.
MS (ESI MH+): 513
CHNO: C24H18Cl2N4O5

Examples 85 to 89

The compounds of Examples 85 to 89 shown in Table 10 were synthesized by the same procedure as that of Example 84 except that respective corresponding 2-nitrobenzoic acid was used in Process 1 of Example 84. Meanwhile, R1, R2, R3 and R4 in Table 10 are substituents in the following general formula (32).

Example 90

Synthesis of the Compound of the Following General Formula (32) which has Substituents of Example 90 of Table 10

Process 1 Construction of Triazene Ring, Cleavage from Resin

The resin obtained in Process 2 of Example 31 was treated in accordance with Process 2 of Example 81 and then treated in accordance with Process 7 of Example 1 to obtain the intended compound.
MS (ESI MH+): 483
CHNO: C23H16Cl2N4O4

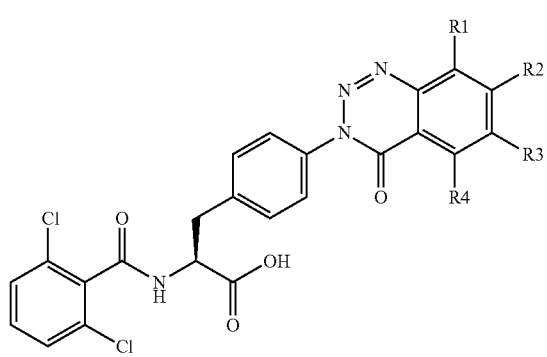

(32)

TABLE 10

| Example | R1— | R2— | R3 | R4 | MS Found (MH+) |
|---|---|---|---|---|---|
| 81 | chloro | H— | H— | chloro | 551 |
| 82 | chloro | H— | chloro | H— | 551 |
| 83 | H— | fluoro | H— | H— | 501 |
| 84 | H— | H— | methoxy | H— | 513 |
| 85 | H— | H— | fluoro | H— | 501 |
| 86 | methyl | H— | H— | H— | 497 |
| 87 | H— | H— | chloro | H— | 517 |
| 88 | chloro | H— | H— | H— | 517 |

TABLE 10-continued

| Example | R1— | R2— | R3 | R4 | MS Found (MH+) |
|---|---|---|---|---|---|
| 89 | H— | H— | H— | methyl | 497 |
| 90 | H— | H— | H— | H— | 483 |

Example 91

Synthesis of the Compound of the Following General Formula (33) which has Substituents of Example 91 of Table 11

Process 1 Acylation, Reduction of Nitro Group

Acylation and reduction of a nitro group were conducted in accordance with Process 1 of Example 84 by using the resin obtained in Process 4 of Example 1.

Process 2 Cyclization by Ortho Ester and Cleavage from Resin

Tetraethoxymethane (800 ul), acetic acid (200 ul), and NMP (2 ml) were added to the resin obtained in Process 1 (150 mg) and stirred at 55° C. for 15 hours. After washing it with DMF, methanol and dichloromethane three times each and drying under reduced pressure, the resin was treated in accordance with Process 7 of Example 1 to obtain the intended compound.
MS (ESI MH+): 556
CHNO: C27H23Cl2N3O6

Examples 92 to 94

The compounds of Examples 92 to 94 shown in Table 11 were synthesized by the same procedure as that of Example 91 except that respective corresponding 2-nitrobenzoic acid was used in Process 1 of Example 91. Meanwhile, R1, R2, R3 and R4 in Table 11 are substituents in the following general formula (33).

Example 95

Synthesis of the Compound of the Following General Formula (33) which has Substituents of Example 95 of Table 11

Process 1 Acylation 2-amino-4-fluorobenzoic acid (636 mg, 4.10 mmol), HOAt (558 g, 4.10 mmol), DIC (317 uL, 2.05 mmol) and NMP (11.5 mL) were added to the resin obtained in Process 4 of Example 1 (500 mg) and stirred for 24 hours. After that, the resin was washed with DMF, methanol and dichloromethane three times each and dried under reduced pressure.

Process 2 Cyclization with Ortho Ester and Cleavage from Resin

The resin obtained in Process 1 was cyclized in accordance with Process 2 of Example 91 and then the intended compound was obtained by being treated in accordance with Process 7 of Example 1.
MS (ESI MH+): 544
CHNO: C26H20Cl2FN3O5

(33)

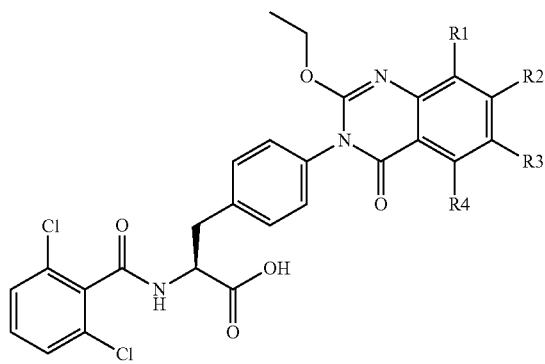

TABLE 11

| Example | R1— | R2— | R3 | R4 | MS Found (MH+) |
|---|---|---|---|---|---|
| 91 | H— | H— | methoxy | H— | 556 |
| 92 | H— | H— | fluoro | H— | 544 |
| 93 | H— | H— | chloro | H— | 560 |
| 94 | H— | H— | H— | methyl | 540 |
| 95 | H— | fluoro | H— | H— | 544 |

Example 96

Synthesis of the Compound of the Following General Formula (34) which has a Substituent of Example 96 of Table 12

Process 1 Acylation, Reduction of Nitro Group

Acylation was conducted by reacting the resin obtained in Process 4 of Example 1 (1 g) with 6-methyl-2-nitrobenzoic acid (1.49 g, 8.21 mmol), DIC (635 uL, 4.11 mmol), HOAt (1.12 g, 8.21 mmol) and NMP (23 mL) for 18 hours. Then, the nitro group was reduced in accordance with Process 2 of Example 31.

Process 2 Cyclization

Carbonyldiimidazole (400 mg) and NMP (2 mL) were added to the resin obtained in Process 1 (200 mg) and stirred at 95° C. for 15 hours. After that, the resin was washed with DMF, methanol and dichloromethane three times each and dried under reduced pressure.

Process 3 Alkylation

Ethyl iodide (200 ul) and tetramethyl guanidine (200 ul) were added to the resin obtained in Process 2 (200 mg) and stirred for 24 hours. After washing it with water, DMF, methanol and dichloromethane three times each and drying under reduced pressure, the resin was treated in accordance with Process 7 of Example 1 to obtain the intended compound.
MS (ESI MH+): 540
CHNO: C27H23Cl2N3O5

Example 97

The compounds of Examples 97 shown in Table 12 was synthesized by the same procedure as that of Example 96 except that the corresponding halide was used in Process 3 of Example 96. Meanwhile, R in Table 12 is a substituent in the following general formula (34).

(34)

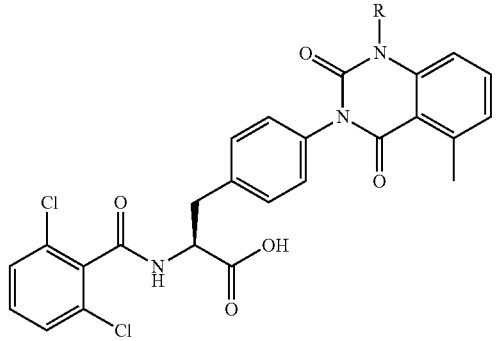

TABLE 12

| Example | R— | MS Found (MH+) |
|---|---|---|
| 96 | ethyl | 540 |
| 97 | benzyl | 602 |

Example 98

Synthesis of the Compound of the Following General Formula (35) which has Substituents of Example 98 of Table 13

Process 1 Sulfonamidation, Reduction of Nitro Group 2-nitrobenzenesulfonyl chloride (450 mg), 2,6-lutidine (450 ul) and dichloromethane (10 ml) were added to the resin obtained in Process 4 of Example 1 (400 mg) and stirred for 14 hours. After washing it with DMF, methanol and dichloromethane three times each and drying under reduced pressure, the nitro group was reduced in accordance with Process 2 of Example 31.

Process 2 Cyclization

Carbonyldiimidazole (400 mg) and NMP (2 mL) were added to the resin obtained in Process 1 (200 mg) and stirred at 95° C. for 15 hours. After that the resin was washed with DMF, methanol and dichloromethane three times each and dried under reduced pressure.

Process 3 Alkylation, Cleavage from Resin

Methyl iodide (400 ul), diisopropylethylamine (400 ul) and NMP (2 ml) were added to the resin obtained in Process 2 (200 mg) and stirred for 17 hours. After washing it with water, DMF, methanol and dichloromethane three times each and drying under reduced pressure, the resin was treated in accordance with Process 7 of Example 1 to obtain the intended compound.
MS (ESI MH+): 548
CHNO: C24H19Cl2N3O6S

Examples 99 to 103

The compounds shown in Table 13 were synthesized by the same procedure as that of Example 98 except that respective corresponding sulfonyl chlorides were used in Process 1 of Example 98. Meanwhile, R1, R2, R3, R4 and R5 in Table 13 are substituents in the following general formula (35) and the same procedure as that of Example 98 was repeated in Examples 101 to 103 except that alkylation in Process 3 of Example 98 was not conducted.

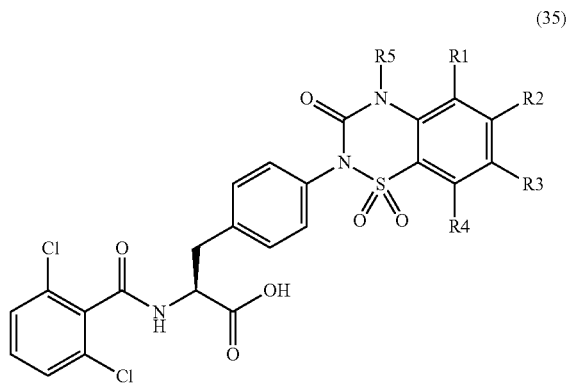

(35)

TABLE 13

| Example | R1— | R2— | R3— | R4— | R5— | MS Found (MH+) |
|---|---|---|---|---|---|---|
| 98 | H— | H— | H— | H— | methyl | 548 |
| 99 | H— | methoxy | H— | H— | methyl | 578 |
| 100 | H— | trifluoromethyl | H— | H— | methyl | 616 |
| 101 | H— | H— | H— | H— | H— | 534 |
| 102 | H— | methoxy | H— | H— | H— | 564 |
| 103 | H— | trifluoromethyl | H— | H— | H— | 602 |

Example 104

Synthesis of the Compound of the Following General Formula (36) which has a Substituent of Example 104 of Table 14

Process 1 Acylation, Construction of quinazoline-2,4-dione Ring, Alkylation and Reduction of Nitro Group Acylation was conducted by using the resin obtained in Process 4 of Example 1 (500 mg), 2-amino-5-nitrobenzoic acid (746 mg, 4.10 mmol), DIC (317 ul, 2.05 mmol), HOAt (558 mg, 4.10 mmol) and NMP (11.5 ml). Then quinazoline-2,4-dione ring was constructed in accordance with Process 2 of Example 96 and alkylation was conducted in accordance with Process 6 of Example 1. Further, the nitro group was reduced in the same way of Process 4 of Example 1.

Process 2 Acylation

Acetic anhydride (600 ul), pyridine (600 ul) and NMP (3 ml) were added to the resin obtained in Process 1 and stirred for 19 hours. After washing it with water, DMF, methanol and dichloromethane three times each and drying under reduced pressure, the resin was treated in accordance with Process 7 of Example 1 to obtain the intended compound.
MS (ESI MH+): 569
CHNO: C27H22Cl2N4O6

Examples 105 to 107

The compounds shown in Table 14 were synthesized by the same procedure as that of Example 104 except that the corresponding acid chloride was used in Process 2 of Example 104. Meanwhile, R in Table 14 is a substituent in the following general formula (36) and the same procedure as that of Example 104 was repeated in Example 107 except that acylation in Process 2 of Example 104 was not conducted.

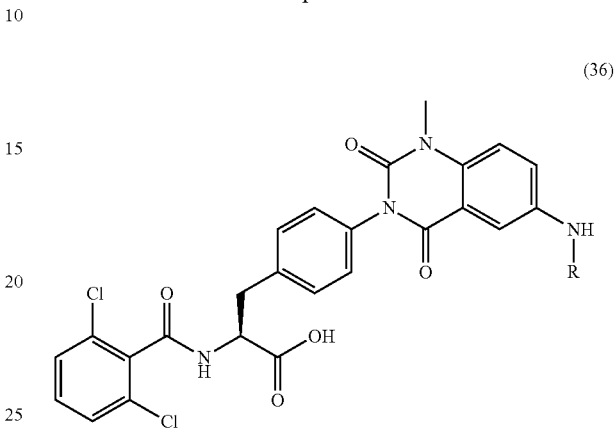

(36)

TABLE 14

| Example | R— | MS Found (MH+) |
|---|---|---|
| 104 | acetyl | 569 |
| 105 | methoxyacetyl | 599 |
| 106 | pivaloyl | 611 |
| 107 | H | 527 |

Example 108

Synthesis of the Compound of the Following General Formula (37) which has a Substituent of Example 108 of Table 15

Process 1 Acylation

The resin obtained in Process 4 of Example 1 (1 g) was acylated by using 5-fluoro-2-nitrobenzoic acid (1.63 g, 8.81 mmol), DIC (675 ul, 4.3 mmol), HOAt (1.2 g, 8.81 mmol) and NMP (25 ml).

Process 2 Substitution of Fluoro Group with Amine, Reduction of Nitro Group THF solution of 2.0M dimethylamine (3 mL) and NMP (2 mL) were added to the resin obtained in Process 1 (200 mg) and stirred for 14 hours. After washing it with water, DMF and dichloromethane three times each and drying under reduced pressure, the nitro group was reduced in accordance with Process 2 of Example 31.

Process 3 Construction of quinazoline-2,4-dione Ring

The resin obtained in Process 2 was treated in accordance with Process 2 of Example 96 to construct quinazoline-2,4-dione ring.

Process 4 Alkylation

Triphenylphosphine (520 mg), methanol (80 ul), 40% toluene solution of diisopropylazodicarboxylic acid (1 ml) and dichloromethane (2 ml) were added to the resin obtained in Process 3 and stirred for 7 hours. After washing it with water, DMF, methanol and dichloromethane three times each and drying under reduced pressure, the resin was treated in accordance with Process 7 of Example 1 to obtain the intended compound.

MS (ESI MH+): 555
CHNO: C27H24Cl2N4O5

Examples 109 to 111

The compounds of Examples 109 to 111 shown in Table 15 were synthesized by the same procedure as that of Example 108 except that the corresponding amine was used in Process 2 of Example 108. Meanwhile, R in Table 15 is a substituent in the following general formula (37).

Example 112

Synthesis of the Compound of the Following General Formula (37) which has a Substituent of Example 112 of Table 15

Process 1 Substitution of Fluoro Group by Amine, Reduction of Nitro Group

THF solution of 2.0M dimethylamine (3 mL) and NMP (2 mL) were added to the resin (200 mg) obtained in Process 1 of Example 108 and stirred for 14 hours. After washing it with water, DMF and dichloromethane three times each and drying under reduced pressure the nitro group was reduced in accordance with Process 2 of Example 31.

Process 3 Construction of quinazoline-2,4-dione Ring

The resin obtained in Process 2 was treated in accordance with Process 2 of Example 96 to construct quinazoline-2,4-dione ring

Process 4 Alkylation

Methyl iodide (400 ul), diisopropylethylamine (400 ul) and NMP (2 ml) were added to the resin obtained in Process 3 (200 mg) and stirred for 17 hours. After washing it with water, DMF, methanol and dichloromethane three times each and drying under reduced pressure, the resin was treated in accordance with Process 7 of Example 1 to obtain the intended compound.

MS (ESI MH+): 569
CHNO: C28H27Cl2N4O5

Example 113

The compound of Example 113 shown in Table 15 was synthesized by the same procedure as that of Example 112 except that the corresponding amine was used in Process 1 of Example 112. Meanwhile, R in Table 15 is a substituent in the following general formula (37).

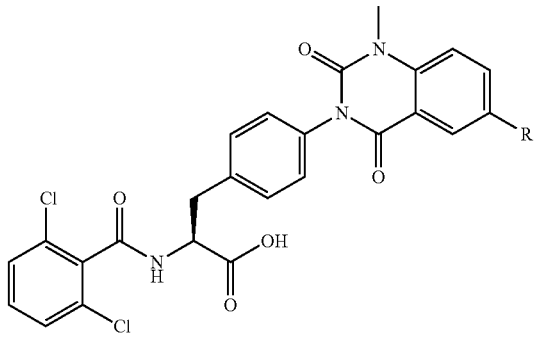

(37)

TABLE 15

| Example | R— | MS Found (MH+) |
|---|---|---|
| 108 | dimethylamino | 555 |
| 109 | ethylmethylamino | 569 |
| 110 | pyrrolidyl | 581 |
| 111 | diethylamino | 583 |
| 112 | formula X 1 | 569 |
| 113 | formula X 2 | 595 |

Formulae X1 and X2 are described below.

NMR data of the compound of Example 108: $^1$H-NMR (400 MHz, DMSO-$d_6$) δ 2.94 (3H, m), 3.02 (1H, dd, J=10.2, 14.1 Hz), 3.22 (1H, m, J=4.4, 14.1 Hz), 3.49 (3H, s), 4.82 (1H, m), 7.17 (2H, d), 7.24 (1H, d), 7.30 (1H, m), 7.36-7.45 (5H, m), 9.15 (1H, d).

$^{13}$C-NMR (100 MHz, DMSO-$d_6$) δ 30.90, 36.64, 40.77, 53.68, 109.21, 116.00, 116.22, 121.37, 128.26, 128.93, 129.90, 131.23, 131.82, 132.10, 135.23, 136.56, 137.57, 146.72, 150.38, 161.88, 163.91, 172.72.

Formula X1

Formula X2

Example 114

Synthesis of the Compound of the Following General Formula (38) which has Substituents of Example 114 of Table 16

Process 1 Alkylation 2,6-dichlorobenzyl alcohol (531 mg), triphenylphosphine (786 mg), dichloromethane (3 ml) and 40% toluene solution of diisopropylazodicarboxylic acid (1.5 ml) were added to the resin obtained in Process 5 of Example 1 (150 mg) and stirred for 14 hours. After washing it with water, DMF, methanol and dichloromethane three times each and drying under reduced pressure, the resin was treated in accordance with Process 7 of Example 1 to obtain the intended compound.

MS (ESI MH+): 656
CHNO: C31H21Cl4N3O5

Examples 115 to 123

The compounds of Examples 115 to 123 shown in Table 16 were synthesized by the same procedure as that of Example 114 except that respective corresponding alcohol was used in Process 1 of Example 114. Meanwhile, R1, R2, R3, R4, R5 and n in Table 16 are substituents in the following general formula (38).

Example 124

Synthesis of the Compound of the Following General Formula (38) which has Substituents of Example 124 of Table 16

Process 1 Acylation

The resin obtained in Process 4 of Example 1 (150 mg) was acylated by using N-phenylanthranilic acid (437 mg, 2.05 mmol), HOAt (279 mg, 2.05 mmol), DIC (106 ul, 1.03 mmol) and NMP (6 ml).

Process 2 Construction of quinazoline-2,4-dione Ring

The resin obtained in Process 1 was treated in accordance with Process 2 of Example 96. After quinazoline-2,4-dione ring was constructed, the resin was treated in accordance with Process 7 of Example 1 to obtain the intended compound.

MS (ESI MH+): 574
CHNO: C30H21Cl2N3O5

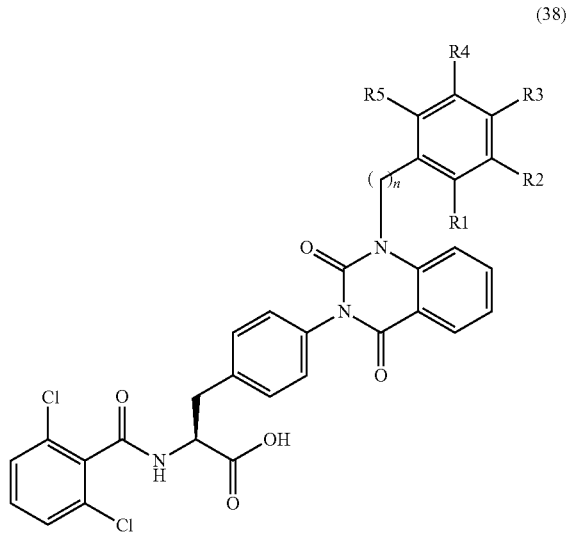

(38)

TABLE 16

| Example | R1— | R2— | R3— | R4— | R5— | n= | MS Found (MH+) |
|---|---|---|---|---|---|---|---|
| 114 | chloro | H | H | H | chloro | 1 | 656 |
| 115 | H | chloro | chloro | H | H | 1 | 656 |

TABLE 16-continued

| Example | R1— | R2— | R3— | R4— | R5— | n= | MS Found (MH+) |
|---|---|---|---|---|---|---|---|
| 116 | chloro | H | chloro | H | H | 1 | 656 |
| 117 | H | H | chloro | H | H | 1 | 622 |
| 118 | H | H | methyl | H | H | 1 | 602 |
| 119 | chloro | H | H | H | H | 1 | 622 |
| 120 | methyl | H | H | H | H | 1 | 602 |
| 121 | chloro | H | H | H | fluoro | 1 | 640 |
| 122 | H | H | H | H | H | 1 | 588 |
| 123 | H | H | H | H | H | 2 | 602 |
| 124 | H | H | H | H | H | 0 | 574 |

Example 125

Synthesis of the Compound of the Following General Formula (39) which has a Substituent of Example 125 of Table 17

Process 1 Synthesis of Iminophosphine

Triphenylphosphine (7.86 g), 40% toluene solution of diisopropylazodicarboxylic acid (30 ml) and toluene (30 ml) were added to the resin obtained in Process 4 of Example 1 (1 g) and stirred for 16 hours. After that, the resin was washed with dichloromethane ten times and dried under reduced pressure.

Process 2 Synthesis of Carbodiimide, Nucleophilic Addition of Amine and Ring Closure Methyl 2-isocyanatebenzoate (200 mg) and dichloromethane (1 ml) were added to the resin obtained in Process 1 (100 mg), stirred for 1 hour and washed with DMF and dichloromethane three times each. Cyclobutylamine (600 ul) and NMP (3 ml) were added to the obtained resin and stirred for 13 hours. After washing it with DMF, methanol and dichloromethane and drying under reduced pressure, the resin was treated in accordance with Process 7 of Example 1 to obtain the intended compound.

MS (ESI MH+): 551
CHNO: C28H24Cl2N4O4

Examples 126 to 130

The compounds shown in Table 17 were synthesized by the same procedure as that of Example 125 except that respective corresponding amine was used in Process 2 of Example 125. Meanwhile, R in Table 17 is a substituent in the following general formula (39).

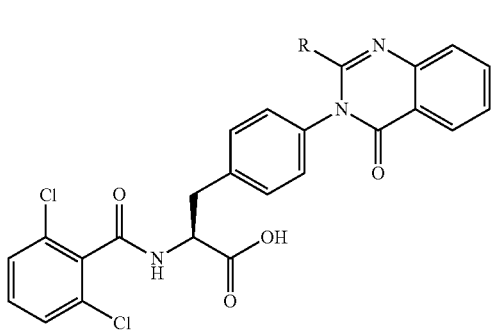

(39)

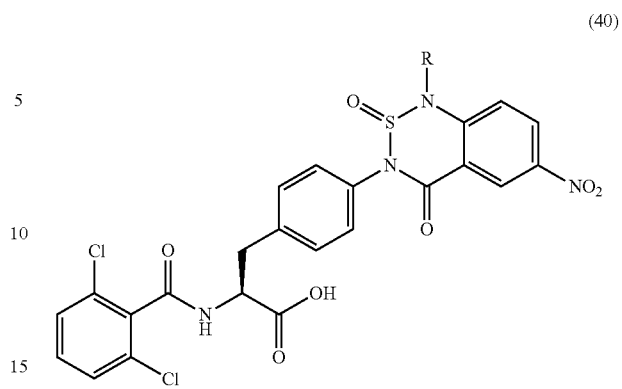

(40)

TABLE 17

| Example | R— | MS Found (MH+) |
| --- | --- | --- |
| 125 | cyclobutylamino | 551 |
| 126 | isobutylamino | 553 |
| 127 | isopropylamino | 539 |
| 128 | dimethylamino | 525 |
| 129 | ethylmethyamino | 539 |
| 130 | azetidino | 537 |

TABLE 18

| Example | R— | MS Found (MH+) |
| --- | --- | --- |
| 131 | methyl | 576 |
| 132 | ethyl | 590 |
| 133 | benzyl | 652 |

Example 131

Synthesis of the Compound of the Following General Formula (40) which has a Substituent of Example 131 of Table 18

Process 1 Substitution of Fluoro Group with Amine

THF solution of 2.0M methylamine (3 mL) and NMP (2 mL) were added to the resin obtained in Process 1 of Example 57 (150 mg) and stirred for 14 hours. Then the resin was washed with DMF and dichloromethane three times each and dried under reduced pressure.

Process 2 Ring Closure with Thionyl Chloride

Triazole (250 mg), thionyl chloride (80 ul), dichloromethane (1 ml) and diisopropylethylamine (400 ul) were added to the resin obtained in Process 1 and stirred for 15 hours. After washing it with DMF, methanol and dichloromethane three times each and drying under reduced pressure, the resin was treated in accordance with Process 7 of Example 1 to obtain the intended compound.

MS (ESI MH+): 576
CHNO: C24H18Cl2N9O7S

Examples 132 and 133

The compounds shown in Table 18 were synthesized by the same procedure as that of Example 131 except that respective corresponding amine was used in Process 1 of Example 131. Meanwhile, R in Table 18 is a substituent in the following general formula (40).

Example 134

Synthesis of the Compound of the Following General Formula (41) which has a Substituent of Example 134 of Table 19

Process 1 Acylation, Removal of Fmoc Group

Acylation was conducted by reacting the resin obtained in Process 4 of Example 1 (500 mg) with Fmoc-β-alanine (810 mg, 2.60 mmol), DIC (200 ul, 1.30 mmol), HOAt (351 mg, 2.60 mmol) and NMP (10 ml) for 18 hours and then Fmoc group was removed in accordance with Process 2 of Example 1.

Process 2 Ring Closure with Carbonyldiimidazole

Carbonyldiimidazole (400 mg) and NMP (2 ml) were added to the resin obtained in Process 1 and stirred for 3 hours. Then, the resin was washed with DMF, methanol and dichloromethane three times each and dried under reduced pressure. Further, NMP (2 ml) was added to the obtained resin and stirred at 95° C. for 15 hours. After washing it with DMF, methanol and dichloromethane three times each and drying under reduced pressure, the resin was treated in accordance with Process 7 of Example 1 to obtain the intended compound.

MS (ESI MH+): 450
CHNO: C20H17Cl2N3O5

Example 135

Synthesis of the Compound of the Following General Formula (41) which has a Substituent of Example 135 of Table 19

Process 1 2-nitrosulfonylation, Alkylation 2-nitrosulfonyl chloride (176 mg), 2,6-lutidine (184 ul) and dichloromethane (4 ml) were added to the resin obtained in Process 1 of Example 134 (250 mg) and stirred at 4° C. for 16 hours. After washing it with DMF, methanol and dichloromethane three times each and drying under reduced pressure, the obtained resin was alkylated in accordance with Process 4 of Example 108.

Process 2 Removal of 2-nitrosulfonyl Group 2-mercaptoethanol (600 ul), diazabicycloundecene (300 ul) and NMP (3 ml) were added to the resin obtained in Process 1 and stirred for 1 hour.
Then, the resin was washed with DMF, methanol and dichloromethane three times each and dried under reduced pressure.

Process 3 Ring Closure with Carbonyldiimidazole

Carbonyldiimidazole (500 mg) and dichloromethane (2.5 ml) were added to the resin obtained in Process 2 and stirred for 10 hours. Then, the resin was washed with DMF, methanol and dichloromethane three times each and dried under reduced pressure. Further, potassium carbonate (200 mg) and NMP (1 ml) were added to the obtained resin and stirred at 95° C. for 17 hours. After washing it with water, DMF, methanol and dichloromethane three times each and drying under reduced pressure, the resin was treated in accordance with Process 7 of Example 1 to obtain the intended compound.
MS (ESI MH+): 464
CHNO: C21H19Cl2N3O5

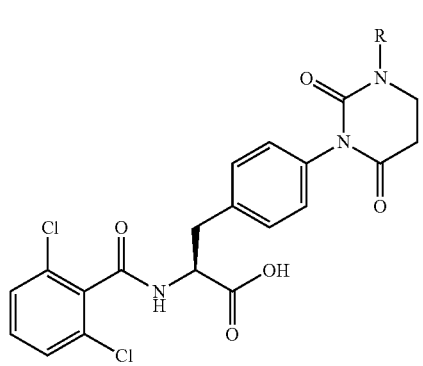

(41)

TABLE 19

| Example | R— | MS Found (MH+) |
|---|---|---|
| 134 | H | 450 |
| 135 | methyl | 464 |

Example 136

Synthesis of the Compound of the Following General Formula (73) which has Substituents of Example 136 of Table 20

Process 1 Acylation, Removal of O-acyl Group

Salicylic acid (74 mg, 0.535 mmol), PyBOP (278 mg, 0.535 mmol), HOBt (120 mg, 0.89 mmol), DIEA (0.186 ml, 1.068 mmol) and DMF (3.6 ml) were added to the resin obtained in Process 4 of Example 1 and stirred for 19 hours. Then, the resin was washed with DMF, methanol and dichloromethane eight times each and 30% ethanolamine/DMF (5 ml) was added to the obtained resin and stirred for 4 hours. The resin was again washed with DMF, methanol and dichloromethane eight times each.

Process 2 Ring Closure with Carbonyldiimidazole, Cleavage from Resin

Carbonyldiimidazole (98 mg) and DCM (6 ml) were added to the resin obtained in Process 1 (50 mg), stirred for 1 hour and washed with dichloromethane five times. Further, dichloromethane (4 ml) was added to the obtained resin, stirred at room temperature for 3 hours and washed with dichloromethane five times. Then, the intended compound was obtained by cleavage from the resin and HPLC purification in the same way of Process 7 of Example 1 (3 mg).
MS (ESI MH+): 499
CHNO: C24H16CL2N2O6

Examples 137 to 144

The compounds shown in Table 20 were synthesized by the same procedure as that of Example 136 except that the corresponding salicylic acid was used in Process 1 of Example 136. Meanwhile, R1, R2 and R3 in Table 20 are substituents in the following general formula (73).

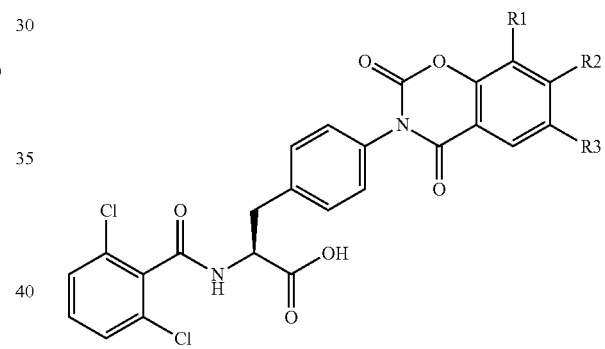

(73)

TABLE 20

| Example | R1 | R2 | R3 | MS Found (MH+) |
|---|---|---|---|---|
| 136 | H | H | H | 499 |
| 137 | —CH=CH—CH=CH— | | H | 549 |
| 138 | H | H | CHO | 527 |
| 139 | H | OMe | H | 529 |
| 140 | OH | H | H | 515 |
| 141 | H | OH | H | 515 |
| 142 | H | NH2 | H | 514 |
| 143 | H | H | Cl | 533 |
| 144 | H | H | F | 517 |

Example 145

Synthesis of the Compound of the Following General Formula (74)

Process 1 Ring Closure with Thiocarbonyldiimidazole

Thiocarbonyldiimidazole (500 mg) and dichloromethane (2.5 ml) were added to the resin obtained in Process 1 of Example 98 and stirred at room temperature for 16 hours. Then the resin was washed with methanol, DMF and dichloromethane three times each and dried under reduced pressure.

Process 2 Cleavage from Resin

The resin obtained in Process 1 (100 mg) was treated in accordance with Process 7 of Example 1 to obtain 1.2 mg of the intended compound.

MS (ESI MH+): 550
CHNO: C23H17Cl2N3O5S2

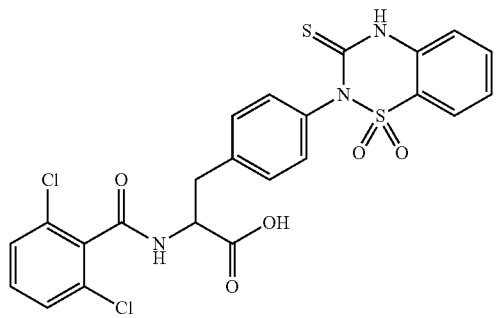

(74)

Example 146

Synthesis of the Compound of the Following General Formula (75)

Methylation and Cleavage from Resin

Diisopropylethylamine (200 ul), methyl iodide (100 ul) and NMP (3 ml) were added to 100 mg of the resin obtained in Process 1 of Example 145 and stirred at room temperature for 16 hours. After washing it with methanol, DMF and dichloromethane three times each and drying under reduced pressure, the resin was treated in according with Process 7 of Example 1 to obtain 13 mg of the intended compound.

MS (ESI MH+): 564
CHNO: C24H19Cl2N3O5S2

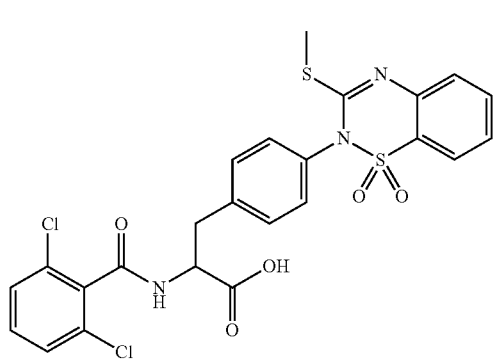

(75)

Example 147

Synthesis of the Compound of the Following General Formula (76) which has Substituents of Example 147 of Table 21

The resin obtained in Process 4 of Example 1 was prepared to be a starting material. 500 mg of 2-nitrobenzylbromide, 5000 of diisopropylethylamine and 5 ml of NMP were added to 100 mg of the said resin and stirred at room temperature for 12 hours. After removing the reaction solvent, the resin was washed with dichloromethane, NMP and dichloromethane three times each. NMP (0.5 mL).EtOH (3 mL) solution of $SnCl_2 \cdot 2H_2O$ (1.5 g) was added to the obtained resin and reacted for 16 hours. The reaction solvent was removed and the resin was washed with NMP and dichloromethane three times each. Further, 200 mg of 2-nitrobenzenesulfonyl chloride, 400 ul of 2,6-lutidine and 2 ml of dichloromethane were added to the obtained resin and reacted at 0° C. for 24 hours. After removing the reaction solvent, the resin was washed with dichloromethane, NMP and dichloromethane three times each. 200 ul of methyl iodide, 0.5 g of potassium carbonate and 7.5 ml of NMP were added to the sulfonamide resin and shaken at 45° C. for 24 hours. After removing the reaction solvent, the resin was washed with dichloromethane, NMP and dichloromethane three times each. 200 µl of Diazabicycloundecene, 400 µul of 2-mercaptoethanol and 500 µl of NMP were added to the obtained resin and stirred at room temperature for 24 hour. Then, the reaction solvent was removed and the resin was washed with dichloromethane, NMP and dichloromethane three times each. Further, 500 mg of carbonyldiimidazole and 4 ml of dichloromethane were added to the obtained resin and shaken at 50° C. form 24 hours. Then, the reaction solvent was removed and the resin was washed with dichloromethane, NMP and dichloromethane three times each and dried under reduced pressure. The obtained resin was treated with 100% trifluoroacetic acid for 1 hour and the resin was filtrated. The obtained filtrate was concentrated and purified by reverse phase HPLC (SYMMETRY 19*50 mm mobile phase water:acetonitrile both of which contained 0.1% TFA) to obtain 0.9 mg of the intended compound.

MS (ESI MH+): 498, 500
CHNO: C25H21Cl2N3O4

Example 148

Synthesis of the Compound of the Following General Formula (76) which has Substituents of Example 148 of Table 21

The resin as a starting material was prepared in the same way as that of Example 147. Thiocarbonyldiimidazole instead of carbonyldiimidazole used in Example 147 was used to obtain 0.8 mg of the intended compound.

MS (ESI MH+): 514, 516
CHNO: C25H21Cl2N3O3S

Example 149

Synthesis of the Compound of the Following General Formula (76) which has Substituents of Example 149 of Table 21

The resin obtained in Process 4 in Example 1 was prepared to be a starting material. 500 mg of 2-nitrobenzylbromide, 500 µl of diisopropylamine and 5 ml of NMP were added to 100 mg of the resin and stirred at room temperature for 12 hours. After removing the reaction solvent, the resin was washed with dichloromethane, NMP and dichloromethane three times each. NMP (0.5 mL) EtOH (3 mL) solution of $SnCl_2 \cdot 2H_2O$ (1.5 g) was added to the obtained resin and reacted for 16 hours. After removing the reaction solvent, the resin was washed with DMF and dichloromethane three times each. Further, 500 mg of carbonyldiimidazole and 4 ml of dichloromethane were added to the resin and shaken at 50° C. for 24 hours. After removing the reaction solvent, the resin was washed with dichloromethane, NMP and dichloromethane three times each and dried under reduced pressure. The obtained resin was treated with 100% solution of trifluoroacetic acid for 1 hour and the resin was filtrated. The obtained filtrate was concentrated and purified by reverse phase HPLC (SYMMETRY 19*50 mm mobile phase water: acetonitrile both of which contained 0.1% TFA) to obtain 0.9 mg of the intended compound.

MS (ESI MH+): 484, 486
CHNO: C24H19Cl2N3O4

Example 150

Synthesis of the Compound of the Following General Formula (76) which has Substituents of Example 150 of Table 21

1.6 mg of the intended compound was synthesized in the same way as that of Example 149 by using 2-fluoro-6-nitrobenzyl bromide.

MS (ESI MH+): 502, 504
CHNO: C24H18Cl2FN3O4

Examples 151 to 159

The compounds shown in Table 21 were synthesized by the same procedure as that of Example 147 except that respective corresponding alkylation reagent was used instead of methyl iodide used in the synthesizing process of Example 147. Meanwhile, R1, RA1, RA2, RA3 and RA4 in Table 21 are substituents in the following general formula (76).

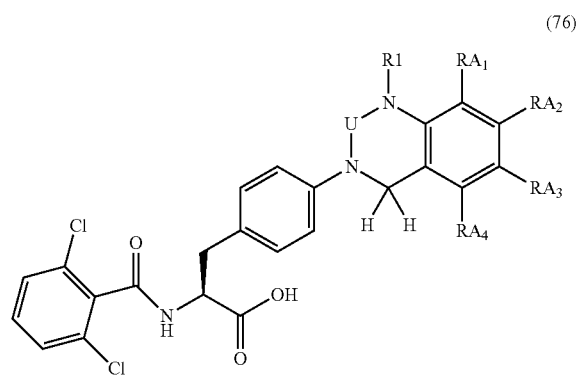

(76)

TABLE 21

| Example | U | R1 | RA1 | RA2 | RA3 | RA4 | MS Found (MH+) |
|---|---|---|---|---|---|---|---|
| 147 | CO | Me | H | H | H | H | 498, 500 |
| 148 | CS | Me | H | H | H | H | 514, 516 |

TABLE 21-continued

| Example | U | R1 | RA1 | RA2 | RA3 | RA4 | MS Found (MH+) |
|---|---|---|---|---|---|---|---|
| 149 | CO | H | H | H | H | H | 484, 486 |
| 150 | CO | H | H | H | H | F | 502, 504 |
| 151 | CO | Et | H | H | H | H | 512, 514 |
| 152 | CO | n-Pr | H | H | H | H | 526, 528 |
| 153 | CO | n-Bu | H | H | H | H | 540, 542 |
| 154 | CO | iso-Pr | H | H | H | H | 526, 528 |
| 155 | CO | iso-Bu | H | H | H | H | 540, 542 |
| 156 | CO | sec-Butyl | H | H | H | H | 540, 542 |
| 157 | CO | 2-Phenylethyl | H | H | H | H | 588, 590 |
| 158 | CO | Benzyl | H | H | H | H | 574, 576 |
| 159 | CO | 2,6-Difluoro-Benzyl | H | H | H | H | 610, 612 |

Example 160

Synthesis of (2S)-2-amino-3-[4-(1-methyl-2,4-dioxo-1,3-dihydroquinazoline-3-yl)phenyl]propionic acid methylester hydrochloride Process 1 Synthesis of 4-nitrophenylalanine methylester hydrochloride 1.49 ml of thionylchloride and 25 ml of methanol were mixed, cooled by dry-ice-acetonitrile bath and 2 g of Boc-Phe(4-NO2)-OH was added thereto. After stirring it for 1 hour and removing the bath, the solution was warmed up till room temperature and further stirred for 2.5 hours. The reaction solvent was concentrated under reduced pressure to obtain 1.83 g of the intended compound as white powder.

MS (ESI MH+): 225
CHNO: C10H12N2O4HCl

Process 2 Synthesis of N-tertiary butyloxycarbonyl-4-nitrophenylalanine methylester 521 mg of 4-nitrophenylalanine methylester hydrochloride obtained in Process 1 was dissolved in the solution of 554 µl of triethylamine in 10 ml of tetrahydrofuran and 480 mg of $(Boc)_2O$ was added thereto under being cooled with ice. The ice bath was removed 5 minutes later and the solution was stirred for 4.5 hours. The ethyl acetate (15 ml) was added to the reaction solvent and washed with 10% aqueous solution of citric acid, water and saturated NaCl aqueous solution respectively. After drying the ethyl acetate layer, the solution was concentrated under reduced pressure to obtain 735 mg of the intended compound.

MS (ESI MH+): 325
CHNO: C15H20N2O6

Process 3 Synthesis of (2S)-2-tertiary butyloxycarbonylamino-3-(4-aminophenyl) propionic acid methylester 648 mg of N-tertiary butyloxycarbonyl-4-nitrophenylalanine methylester obtained in Process 2 was dissolved in 20 ml of ethanol and 150 mg of 5% Pd/C was added and the solution was stirred at room temperature for 18 hours under hydrogen atmosphere (1 atm). After the Celite filtration, the obtained product was purified by silica gel column (hexane:ethyl acetate; 4:1→2:1) to obtain 441 mg of the intended compound.

MS (ESI MH+): 295
CHNO: C15H22N2O4

Process 4 Synthesis of (2S)-2-tertiary butyloxycarbonylamino-3-[4-(2,4-dioxo-1,3-dihydroquinazoline-3-yl)phenyl]propionic acid methylester 683 mg of (2S)-2-tertiary butyloxycarbonylamino-3-(4-aminophenyl) propionic acid methylester obtained in Process 3 was dissolved in 20 ml of acetonitrile and 412 mg of methyl 2-isocyanobenzoate was added and stirred at 70° C. for 16.5 hours. After cooling down to room temperature, the produced powder was picked up by filtration and dried to obtain 588 mg of the intended compound as white powder.

MS (ESI MH+): 440
CHNO: C23H25N3O6

Process 5 Synthesis of (2S)-2-tertiary butyloxycarbonylamino-3-[4-(1-methyl-2,4-dioxo-1,3-dihydroquinazoline-3-yl)phenyl]propionic acid methylester 1.0 g of (2S)-2-tertiary butyloxycarbonylamino-3-[4-(2,4-dioxo-1,3-dihydroquinazoline-3-yl)phenyl]propionic acid methylester obtained in Process 4 was dissolved in 20 ml of N,N-dimethylformamide and 378 mg of potassium carbonate and 0.284 ml of iodomethane were added and stirred for 1 hour. 70 ml of ethyl acetate was further added to the reaction solvent and washed with water and saturated NaCl solution. After drying the ethyl acetate layer the solvent was concentrated under reduced pressure to obtain 1.04 g of the intended compound as yellow powder.

MS (ESI MH+): 454
CHNO: C24H27N3O6

Process 6 Synthesis of (2S)-2-amino-3-[4-(1-methyl-2,4-dioxo-1,3-dihydroquinazoline-3-yl)phenyl]propionic acid methylester hydrochloride 500 mg of (2S)-2-tertiary butyloxycarbonylamino-3-[4-(1-methyl-2,4-dioxo-1,3-dihydroquinazoline-3-yl)phenyl]propionic acid methylester obtained in Process 5 was dissolved in 11 ml of 4N hydrochloric acid-dioxan solution and stirred at room temperature for 1 hour. The reaction solvent was concentrated under reduced pressure to obtain 426 mg of the intended compound as white powder.

MS (ESI MH+): 354
CHNO: C19H19N3O4HCl

Example 161

Synthesis of the Compound of the Following General Formula (77) which has Substituents of Example 161 of Table 22

The mixture of 88.2 mg of 2-chloro-6-methyl benzoic acid, 99.1 mg of 1-(3-dimethylaminopropyl)-3-ethylcarbodiimide hydrochloride, 79.1 mg of 1-hydroxybenzotriazole.monohydrate, 107 µl of triethylamine, 100 mg of (2S)-2-amino-3-[4-(1-methyl-2,4-dioxo-1,3-dihidroquinazoline-3-yl)phenyl] propionic acid methylester hydrochloride and 1 ml of dichloromethane was stirred at 45° C. overnight. The mixture was purified respectively by silica gel chromatography (hexane-ethyl acetate) and reverse phase HPLC to obtain the intended compound.

MS (ESI MH+): 506
CHNO: C27H24N3O5Cl

Example 162

Synthesis of the Compound of the Following General Formula (77) which has Substituents of Example 162 of Table 22

The mixture of 20 mg of methylester compound obtained in Example 161, 2 mg of lithium hydroxide.monohydrate, 1 ml of tetrahydrofuran and 0.2 ml of water was stirred at room temperature for 1 hour. After 1M hydrochloric acid was added and the solution was neutralized, the solvent was evaporated. The intended compound (6.0 mg) was obtained by purifying with reverse phase HPLC.

MS (ESI MH+): 492
CHNO: C26H22N3O5Cl

Examples 163, 166, 168, 170, 172, 174 and 176

Synthesis of the Compound of the General Formula (77) which has Substituents of the Corresponding Example of Table 22

The intended compound was obtained in the same manner as that of Example 161 except that 2-chloro-6-methyl benzoic acid was replaced with a corresponding carboxylic acid in the synthesizing process of Example 161. See Table 22.

Examples 164, 165, 167, 169, 171, 173 and 175

Synthesis of the Compound of the General Formula (77) which has Substituents of the Corresponding Example of Table 22

The intended compound was obtained in the same manner as that of Example 162 except that a corresponding methylester compound was used. See Table 22.

Example 177

Synthesis of the Compound of the General Formula (77) which has Substituents of the Corresponding Example of Table 22

A methylester compound was obtained in the same manner as that of Example 161 except that 2-chloro-6-methyl benzoic acid was replaced with a 2,6-dichlorocinnamic acid in the synthesizing process of Example 161. Then the intended compound was obtained in the same manner as that of Example 162 except that the above resulting methylester was used. See Table 22.

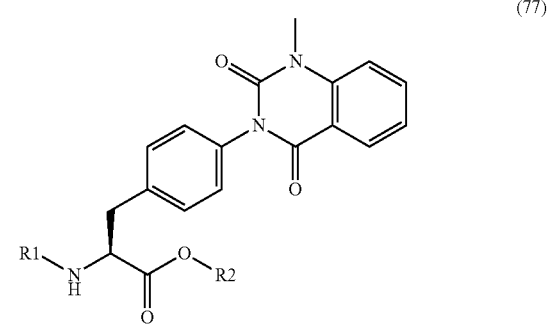

(77)

TABLE 22

| Example | R1— | R2— | MS Found |
|---|---|---|---|
| 161 | 2-chloro-6-methylbenzoyl | Me | 506 (MH+) |
| 162 | 2-chloro-6-methylbenzoyl | H | 492 (MH+) |
| 163 | 2-chloro-6-trifluoromethylbenzoyl | Me | 560 (MH+) |
| 164 | 2-chloro-6-trifluoromethylbenzoyl | H | 544 (MH−) |
| 165 | 2-chloro-6-bromobenzoyl | H | 556 (MH+) |
| 166 | 2-chloro-6-bromobenzoyl | Me | 570 (MH+) |
| 167 | 2-chloro-6-fluorobenzoyl | H | 496 (MH+) |
| 168 | 2-chloro-6-fluorobenzoyl | Me | 510 (MH+) |
| 169 | 3,5-dichloroisonicotinoyl | H | 513 (MH+) |
| 170 | 3,5-dichloroisonicotinoyl | Me | 527 (MH+) |
| 171 | 2,6-dichloro-3-methylbenzoyl | H | 526 (MH+) |
| 172 | 2,6-dichloro-3-methylbenzoyl | Me | 540 (MH+) |
| 173 | 2,4,6-trichlorobenzoyl | H | 546 (MH+) |
| 174 | 2,4,6-trichlorobenzoyl | Me | 560 (MH+) |
| 175 | 2,6-dichloro-3-nitrobenzoyl | H | 557 (MH+) |
| 176 | 2,6-dichloro-3-nitrobenzoyl | Me | 588 (M + NH4+) |
| 177 | 2,6-dichlorocinnamoyl | H | 538 (MH+) |

Example 178

Synthesis of the Compound of the Following General Formula (78) which has a Substituent of Example 178 of Table 23

Process 1 2-nitrosulfonylation, Methylation

The resin obtained in Process 1 of Example 109 was 2-nitrosulfonylated and methylated in accordance with Process 4 of Example 112.

Process 2 Removal of 2-nitrosulfonyl Group

The resin obtained in Process 1 was treated in accordance with Process 2 of Example 135 and 2-nitrosulfonyl group was removed. The intended compound was obtained in accordance with Process 7 of Example 1.

MS (ESI MH+): 541
CHNO: C26H22Cl2N4O5

Example 179

Synthesis of the Compound of the Following General Formula (78) which has a Substituent of Example 179 of Table 23

The intended compound was obtained in the same manner as that of Example 178 except that ethyl bromide was used in Process 1 of Example 178.

MS (ESI MH+): 555
CHNO: C27H24Cl2N4O5

Meanwhile, R in Table 23 is a substituent of the following general formula (78).

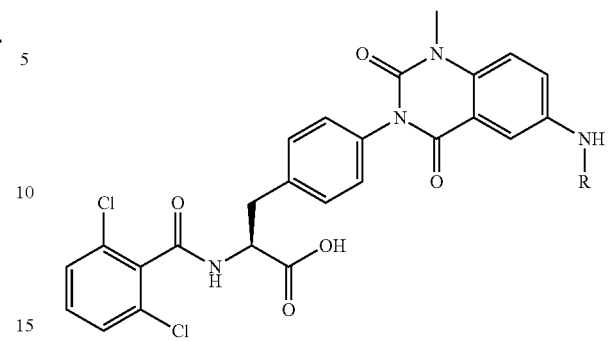

(78)

TABLE 23

| Example | R— | MS Found (MH+) |
|---|---|---|
| 178 | methyl | 541 |
| 179 | ethyl | 555 |

Examples 180 to 189

The compounds in Table 24 below were synthesized in the same manners as those of Example 45 except that respective corresponding substituted 2-nitrobenzoic acid was used in Process 1 of Example 45, and Process 6 and 7 of Example 1. Meanwhile, R1, R2, R3 and R4 in Table 24 are substituents of the following general formula (79).

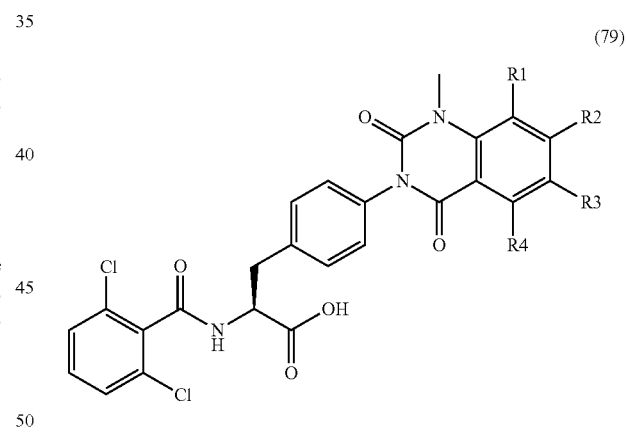

(79)

TABLE 24

| Example | R1— | R2— | R3— | R4— | MS Found (MH+) |
|---|---|---|---|---|---|
| 180 | methoxy | H | H | H | 542 |
| 181 | H | H | H | methyl | 526 |
| 182 | chloro | H | H | H | 546 |
| 183 | H | H | chloro | H | 546 |
| 184 | H | H | methoxy | H | 542 |
| 185 | H | trifluoromethyl | H | H | 580 |
| 186 | methyl | H | H | H | 526 |
| 187 | H | H | H | chloro | 546 |
| 188 | H | methoxy | methoxy | H | 572 |
| 189 | H | H | fluoro | H | 530 |

NMR data of the compound of Example 180: $^1$H-NMR (CDCl$_3$) δ=3.22-3.48 (2H, m), 3.83 (3H, s), 3.93 (3H, s), 5.16-5.23 (1H, m), 7.16 (2H, d, J=7.8 Hz), 7.19-7.34 (6H, m), 7.44 (2H, d, J=8.7 Hz), 7.84 (1H, dd, J=2.4, 6.6 Hz)

Example 190

Synthesis of the Compound of the Following General Formula (80) which has Substituents of Example 190 of Table 25

The compound (3.2 mg) of the general formula (23) that has a substituent of Example 1 in Table 1 was suspended in a mixed solution of methanol (73 µl) and toluene (224 µl) and a hexane solution of 2M trimethylsilyldiazomethane (73 µl) was added thereto. After 30 minutes, the reaction solvent was concentrated under reduced pressure to obtain 3 mg of the intended compound.
MS (ESI MH+): 526
CHNO: C26H21Cl2N3O5

Example 191

Synthesis of the Compound of the Following General Formula (80) which has Substituents of Example 191 of Table 25

The compound (72.7 mg) of the general formula (79) that has a substituent of Example 183 in Table 24 was dissolved in a mixed solution of dichloromethane (10 ml) and isopropanol (0.2 ml). 1-(3-dimethylaminopropyl)-3-ethylcarbodiimide hydrochloride (26 mg) and 4-dimethylaminopyridine (26.2 mg) were added and stirred. After stirring it for 18 hours, 1N hydrochloric acid was added and the solution was extracted with ethyl acetate. The water layer was further extracted with ethyl acetate and mixed with the previously extracted layer, and washed with saturated solution of sodium hydrogencarbonate and saturated NaCl aqueous solution. Then, the organic layer was dried with anhydrous sodium sulphate and concentrated under reduced pressure. The obtained product was purified by high pressure liquid chromatography (water-.acetonitrile) to obtain 10 mg of the intended compound.
MS (ESI MH+): 588
CHNO: C28H24Cl3N3O5

Example 192

Synthesis of the Compound of the Following General Formula (80) which has Substituents of Example 192 of Table 25

The compound (12 mg) of the general formula (37) that has a substituent of Example 111 in Table 16 was dissolved in methanol (0.5 ml), cooled down to −78° C. and thionyl chloride (0.04 ml) was added. After stirring it at room temperature for 7.5 hours, the reaction solvent was concentrated under reduced pressure to obtain 12 mg of the intended compound.
MS (ESI MH+): 597
CHNO: C30H30Cl2N4O5

Examples 193 to 202

The compounds shown below were synthesized by using a carboxylic acid described in respective corresponding Example as a starting material. In this connection, Examples 193 to 195 and 201 were synthesized in the same manner as that of Example 191 except that a suitable alcohol was used. Example 196 to 200 and 202 were synthesized in the same manner as that of Example 192. Meanwhile, R1, R2 and R3 in Table 25 are substituents of the following general formula (80).

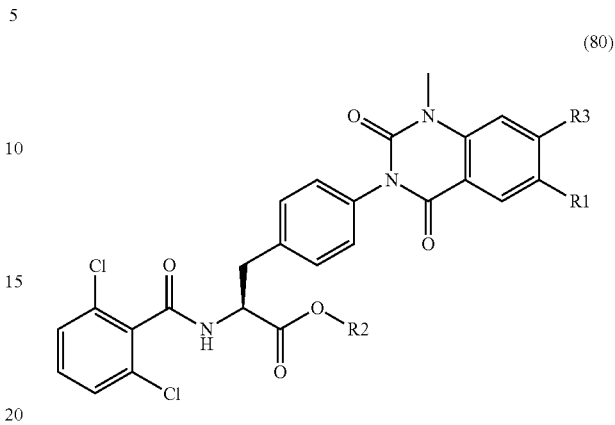

(80)

TABLE 25

| Example | R1— | R2— | R3— | MS Found (MH+) |
|---|---|---|---|---|
| 190 | H | methyl | H | 526 |
| 191 | chloro | isopropyl | H | 588 |
| 192 | diethylamino | methyl | H | 597 |
| 193 | H | ethyl | H | 540 |
| 194 | H | isopropyl | H | 554 |
| 195 | methoxy | ethyl | H | 570 |
| 196 | dimethylamino | methyl | H | 569 |
| 197 | ethylamino | methyl | H | 569 |
| 198 | methylamino | methyl | H | 555 |
| 199 | ethylmethylamino | methyl | H | 583 |
| 200 | amino | methyl | H | 541 |
| 201 | chloro | ethyl | H | 574 |
| 202 | H | methyl | fluoro | 544 |

NMR data of the compound of Example 196: $^1$H-NMR (400 MHz, DMSO-d$_6$) δ 2.94 (3H, m), 3.02 (1H, m), 3.22 (1H, m), 3.58 (3H, s), 3.70 (3H, s), 4.82 (1H, m), 7.18-7.47 (10H, m), 9.28 (1H, d). $^1$C-NMR (100 MHz, DMSO-d$_6$) δ 30.88, 36.37, 40.75, 52.28, 53.66, 109.17, 116.00, 116.22, 121.35, 128.32, 128.99, 129.88, 131.36, 131.79, 132.07, 135.35, 136.35, 137.21, 146.74, 150.37, 161.89, 163.99, 171.72.

Example 203

Synthesis of the Compound of the Following General Formula (81)

Process 1 Acylation

The resin obtained in Process 4 of Example 1 was acylated by using cis-2-[(9-fluorenylmethyloxycarbonyl)amino]-1-cyclohexan carboxylic acid (274 mg), DIC (0.058 ml), HOAt (101 mg) and NMP (2.5 ml).

Process 2 Removal of 9-fluorenylmethyloxycarbonyl Group

The resin obtained in Process 1 was stirred in 20% piperidine-NMP solution for ten minutes twice and washed with NMP, methanol and dichloromethane four times each.

Process 3 Cyclization, Cleavage from Resin

The resin obtained in Process 2 was treated in the same way as that of Process 2 of Example 96 and then treated in accordance with Process 7 of Example 1 to obtain the intended compound.
MS (ESI MH+): 504
CHNO: C24H23Cl2N3O5

(81)

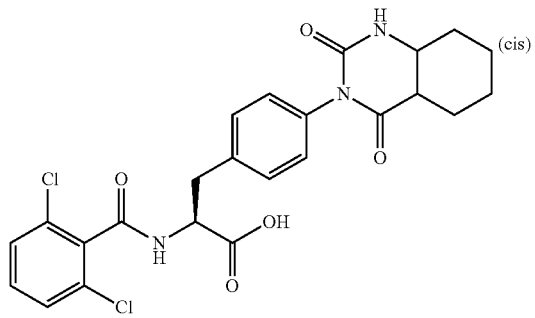

Examples 205 and 206

The compounds of the following general formula (82) that has a substituent in Table 26 were synthesized by using a carboxylic acid obtained in Example 108 as a starting material and in the same manner as that of Example 191 except that a suitable alcohol was used. Meanwhile, R in Table 26 is a substituent of the following general formula (82).

(82)

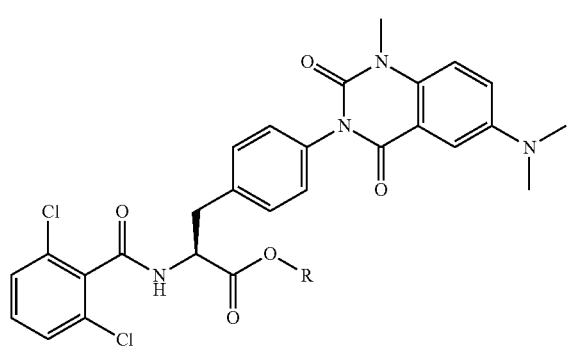

TABLE 26

| Example | R— | MS Found (MH+) |
|---|---|---|
| 205 | ethyl | 583 |
| 206 | isopropyl | 597 |

Examples 207 and 208

The compounds of the following general formula (83) that has substituents in Table 27 were synthesized in the same manner as that of Example 149 except that respective corresponding substituted 2-nitrobenzylbromide was used. Meanwhile, R1 and R2 in Table 27 are substituents of the following general formula (83).

(83)

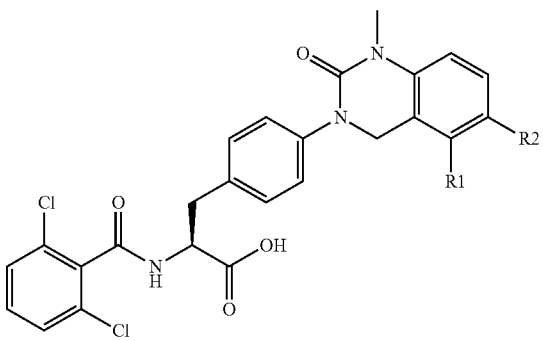

TABLE 27

| Example | R1— | R2— | MS Found (MH+) |
|---|---|---|---|
| 207 | —H | methyl | 512 |
| 208 | fluoro | —H | 516 |

Example 209

The compound of the following general formula (84) that has a substituent of Example 209 in Table 28 was synthesized in the same manners as those of Example 45 except that 3-chloro-2-nitrobenzoic acid was replaced with 1-ethyl-4-nitro-1H-pyrazole-3-carboxylic acid in Process 1 of Example 45, and Process 6 and 7 of Example 1. Meanwhile, R in Table 28 is a substituent of the following general formula (84).

Example 210

The compound of the following general formula (89) that has a substituent of Example 210 in Table 28 was synthesized by using the compound obtained in Example 209 as a starting material and in the same manner as that of Example 192. Meanwhile, R in Table 28 is a substituent of the following general formula (84).

(84)

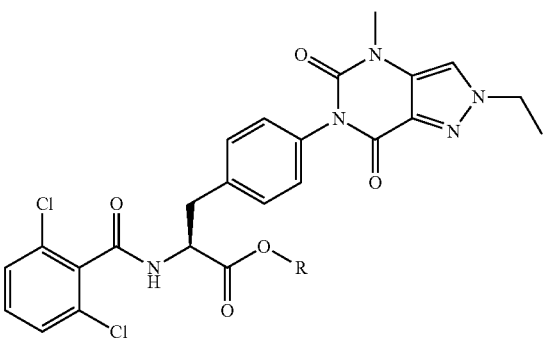

TABLE 28

| Example | R— | MS Found (MH+) |
|---|---|---|
| 209 | H | 530 |
| 210 | methyl | 544 |

Example 211

The compound of the following general formula (85) was synthesized as follows. The compound of the general formula (23) that has a substituent(s) of Example 1 in Table 1 (28.9 mg) was dissolved in DMF (1 ml) and 1-(3-dimethylamino-propyl)-3-ethylcarbodiimide hydrochloride (12.9 mg), 1-hydroxy-7-azabenzotriazole (10.7 mg), hydroxylamine hydrochloride (11.5 mg) and N-methylmorpholine (9.1 mg) were added and stirred. Further, 1-(3-dimethylaminopropyl)-3-ethylcarbodiimide hydrochloride (11.7 mg), 1-hydroxy-7-azabenzotriazole (8.2 mg), hydroxylamine hydrochloride (9.5 mg), N-methylmorpholine (10.5 mg) and DMF (0.5 ml) were added and stirred. Two hours later, water was added to the reaction solvent and the separated crystal was dried to 14.8 mg of the intended compound.

MS (ESI MH−): 525
CHNO: C25H20Cl2N4O5

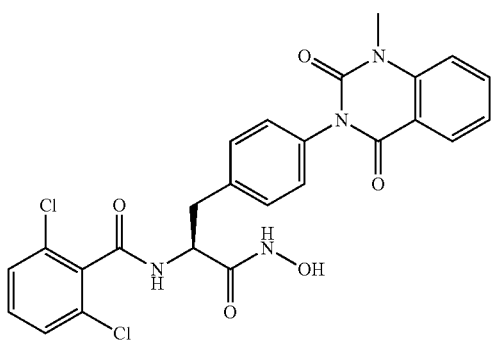

(85)

Example 212

Synthesis of the Compound of the Following General Formula (86) which has a Substituent of Example 212 of Table 29

Process 1 Synthesis of (2S)-2-(t-butoxycarbonylamino)-3-[4-(1 methyluracil-3-yl)phenyl]propionic acid methylester The mixture of 30 mg of (2S)-2-(t-butoxycarbonylamino)-3-[4-(dihydroxy boranyl)phenyl]propionic acid, 25 mg of 1-methyluracil, 27 mg of copper acetate(II), 40 mg of triethylamine and 4 ml of dichloromethane were stirred overnight. The reaction solvent was diluted by ethanol and filtered by Celite filtration. The residual material obtained by concentrating the filtrate was dilluted by 1N sodium hydroxide and washed with ethyl acetate. After making the water layer acidic by hydrochloric acid, the solution was extracted with ethyl acetate, washed with saturated NaCl aqueous solution, dried with magnesium sulfate and the solvent was removed to obtain a crude material of (2S)-2-(t-butoxycarbonylamino)-3-[4-(1-methyluracil-3-yl)phenyl]propionic acid. This crude material was diluted by 5 ml of ethanol and hexane solution including 2M trimethylsilyldiazomethane was added to give methyl ester. The reaction solvent was concentrated and purified by silica gel chromatography (ethyl acetate-ethanol) to obtain the title compound (7 mg).

MS (ESI MH+): 404
$^1$H-NMR (DMSO-$d_6$) δ 1.45 (9H, s), 3.15 (2H, d), 3.40 (3H, s), 3.70 (3H, s), 4.60 (1H, m), 5.00 (1H, m), 5.85 (1H, d), 7.15 (2H, d), 7.20 (1H, d), 7.30 (2H, d)

Process 2 Synthesis of (2S)-2-(2,6-dichlorobenzoylamino)-3-[4-(1-methyluracil-3-yl)phenyl]propionic acid methylester 6 ml of dioxan solution including 4N hydrogen chloride was added to 86 mg of (2S)-2-(t-butoxycarbonylamino)-3-[4-(1-methyluracil-3-yl)phenyl]propionic acid methylester and stirred for 1 hour. 10 ml of dimethylformamide, 62 µl of triethylamine and 34 µl of 2,6-dichloromenzoyl chloride were added to the residual material obtained by removing the solvent and stirred for 30 minutes. The reaction solvent was diluted by ethyl acetate, washed with 1N hydrochloric acid, an aqueous solution of saturated sodium hydrogen carbonate and saturated NaCl aqueous solution, and dried with magnesium sulfate and the solvent was removed to obtain a crude material of the title compound. The crude material was purified by reverse phase HPLC to obtain the title compound (26 mg).

MS (ESI MH+): 476
H-NMR (CDCl$_3$) δ 3.30 (2H, br), 3.40 (3H, s), 3.75 (3H, s), 5.25 (1H, q), 5.85 (1H, d), 6.90 (1H, d) 7.15 (2H, d), 7.20-7.40 (6H, m)

Example 213

Synthesis of the Compound of the Following General Formula (86) which has a Substituent of Example 213 of Table 29

The mixture of 10 mg of (2S)-2-(2,6-dichlorobenzoylamino)-3-[4-(1-methyluracil-3-yl)phenyl]propionic acid methylester, 3 ml of dioxan solution including 4N hydrogen chloride and 3 ml of water were stirred at 80° C. for 4 hours. After the solvent was removed, the crude material was purified by reverse phase HPLC to obtain the said compound (3 mg).

MS (ESI MH+): 462

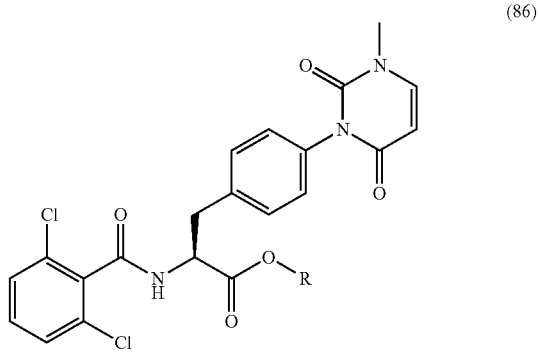

(86)

TABLE 29

| Example | R— | MS Found (MH+) |
|---|---|---|
| 212 | methyl | 476 |
| 213 | —H | 462 |

Referencial Example 1

2-chloro-6-trifuluoromethylbenzoic acid

The mixture of 500 mg of 3-chlorobenzotrifuluoride and 3 ml of tetrahydrofuran was cooled down to −50° C. and 2 ml of 1.6M n-butyllithium hexan solution was added and stirred for 1 hour. The mixture was put into dry ice and diluted by an aqueous solution of 1N sodium hydroxide. After washing it with toluene, the water layer was made acidic by hydrochloric acid and extracted with ethyl acetate. The crude material obtained by removing the solvent was purified by reverse phase HPLC to the said compound.

Yield 244 mg

H-NMR (DMSO-$d_6$) δ 7.68 (1H, t), 7.80 (1H, d), 7.88 (1H, d).

MS (ESI, m/z) 223 (M-H)−

Referencial Example 2

2-bromo-6-chlorobenzoic acid

The mixture of 500 mg of 3-bromochlorobenzen and 3 ml of tetrahydrofuran was cooled down to −78° C. and 1.3 ml of 2.0M lithium diisopropylamide heptane/tetrahydrofuran/ethylbenzene was added. After stirring it for 2 hours, the mixture was put into dry ice and washed and extracted as described in Referencial Example 1 to obtain a crude material. The crude material was washed with a mixed solvent of hexane-ethyl acetate to obtain the said compound.

Yield 317 mg

H-NMR (DMSO-$d_6$) δ 7.40 (1H, t), 7.60 (1H, d), 7.70 (1H, d).

MS (ESI, m/z) 233 (M-H)−

Example 219

VCAM Antagonist Activity (VCAM-1/α4β1 Binding Assay)

The capacity of a test substance antagonistic to the binding of cell strain Jurkat (ATCC TIB-152) of human T cells, known to express integrin α4β1, to VCAM-1 was determined.

100 μl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to ¼ concentration was added in an amount of 150 μl/well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 μg/ml of Calcein-AM (Wako Pure Chemical Industries, Ltd.) at 37° C. in dark place for 30 minutes to label with fluorescence. The cells were again suspended in a binding buffer (20 mM HEPES, DMEM containing 0.1% BSA).

50 μl of a test substance of various concentrations obtained by the dilution with the binding buffer was added to the plate. Immediately thereafter, 50 μl (final volume: 100 μl/well) of the fluorescent Jurkat cells (4×10$^6$ cells/ml) were added thereto, and they were incubated in dark place at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1920 ARVO multi-label counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 30

Example 215

VCAM Antagonistic Activity (VCAM-1/α4β7 Binding Assay)

The capacity of a test substance antagonistic to the binding of lymphoma cell strain RPMI-8866 of human B cells, known to express integrin α4β7, to VCAM-1 was determined.

100 μl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to ¼ concentration was added in an amount of 150 μl/well. After the incubation at room temperature for 1 hour, buffer B was removed and the plate was washed with PBS once.

RPMI-8866 cells were washed with DMEM twice and incubated in Dulbecco modified Eagle medium containing 10 μg/ml of Calcein-AM (Wako Pure Chemical Industries, Ltd.) (SIGMA, hereinafter referred to as "DMEM") in dark place at 37° C. for 30 minutes to label with fluorescence. The cells were again suspended in a binding buffer (20 mM HEPES, DMEM containing 0.1% BSA) containing 4 mM of MnCl$_2$.

50 μl of a test substance of various concentrations obtained by the dilution with the binding buffer was added to the plate. Immediately thereafter, 50 μl (final volume: 100 μl/well) of the fluorescent RPMI-8866 cells (4×10$^6$ cells/ml) were added thereto, and they were incubated in dark place at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 30.

TABLE 30

Results of the determination of VCAM antagonistic activity (IC50, nmol/L)

| Example | α4β7 | α4β1 |
|---|---|---|
| 1 | 1.0 | 18 |
| 2 | 9.2 | 240 |
| 3 | 3.5 | 66 |
| 4 | 2.8 | 26 |
| 5 | 14.0 | 46 |
| 6 | 3.3 | 80 |
| 7 | 22.0 | 110 |
| 8 | 3.9 | 94 |
| 9 | 94.0 | 440 |
| 11 | 74.0 | 6200 |
| 12 | 19.0 | 490 |
| 13 | 4.5 | 220 |
| 14 | 26.0 | 1260 |
| 16 | 14.0 | 1700 |
| 17 | 43.0 | 2100 |
| 18 | 23.0 | 1900 |
| 23 | 18.0 | 7240 |
| 31 | 50.0 | 630 |
| 32 | 64.0 | 2420 |
| 34 | 42.0 | 2210 |
| 35 | 68.0 | 1700 |
| 36 | 6.6 | 490 |
| 37 | 19.0 | 200 |
| 41 | 86.0 | 3410 |
| 42 | 92.0 | 6730 |
| 44 | 79.0 | 4230 |
| 45 | 10.2 | 340 |
| 46 | 6.8 | 195 |
| 47 | 76.0 | 1980 |
| 48 | 28.0 | 1800 |
| 49 | 62.1 | 1180 |
| 50 | 7.9 | 1770 |
| 51 | 30.0 | 1180 |
| 52 | 55.3 | 1310 |
| 53 | 66.1 | 2460 |
| 54 | 9.8 | 71 |
| 57 | 29.9 | 639 |
| 58 | 31.6 | 1070 |
| 59 | 35.8 | 540 |
| 60 | 36.1 | 780 |
| 61 | 42.0 | 1150 |
| 62 | 45.0 | 1450 |
| 63 | 1.3 | 28 |
| 65 | 7.0 | 330 |
| 66 | 1.3 | 170 |
| 67 | 2.2 | 370 |
| 68 | 1.5 | 350 |
| 69 | 2.5 | 5630 |
| 70 | 3.5 | 34 |
| 71 | 11.0 | 185 |
| 72 | 2.6 | 27 |
| 73 | 1.6 | 27 |
| 74 | 2.5 | 53 |
| 75 | 2.3 | 60 |
| 76 | 13.0 | 192 |
| 78 | 9.6 | 180 |
| 79 | 18.0 | 440 |
| 80 | 74.0 | 960 |
| 81 | 8.6 | 72 |
| 84 | 20.0 | 158 |
| 85 | 25.0 | 230 |
| 89 | 2.7 | 41 |
| 90 | 43.7 | 511 |
| 91 | 1.6 | 1200 |
| 92 | 5.7 | 1340 |
| 93 | 4.8 | 4030 |
| 94 | 6.0 | 1150 |
| 95 | 1.8 | 960 |
| 97 | 13.0 | 1500 |
| 99 | 2.0 | 12 |
| 100 | 2.4 | 11 |
| 104 | 1.4 | 16 |
| 105 | 0.8 | 14 |
| 106 | 2.8 | 44 |
| 107 | 1.1 | 17 |
| 108 | 3.3 | 57 |
| 109 | 4.3 | 56 |
| 110 | 4.1 | 55 |
| 111 | 11.0 | 88 |
| 112 | 1.1 | 37 |
| 113 | 1.6 | 52 |
| 114 | 27.0 | 190 |
| 115 | 36.0 | 760 |
| 116 | 35.0 | 450 |
| 117 | 19.0 | 480 |
| 118 | 16.0 | 385 |
| 119 | 21.0 | 440 |
| 120 | 24.0 | 500 |
| 121 | 14.0 | 109 |
| 122 | 0.6 | 310 |
| 123 | 12.0 | 180 |
| 124 | 20.0 | 840 |
| 126 | 70.0 | 1580 |
| 129 | 76.4 | 2023 |
| 131 | 24.0 | 183 |
| 135 | 12.0 | 570 |
| 136 | 3.0 | 565 |
| 137 | 11.2 | 2120 |
| 139 | 17.0 | 107 |
| 142 | 9.0 | 210 |
| 147 | 6.5 | 107 |
| 162 | 0.2 | 34 |
| 164 | 7.1 | 120 |
| 165 | 0.6 | 11 |
| 169 | 0.5 | 6 |
| 180 | 5.4 | 86 |
| 181 | 1.0 | 15 |
| 182 | 6.2 | 113 |
| 183 | 1.7 | 25 |
| 184 | 3.3 | 31 |
| 185 | 2.7 | 12 |
| 186 | 4.3 | 59 |
| 187 | 3.2 | 26 |
| 188 | 2.7 | 11 |
| 189 | 1.1 | 18 |
| 211 | 20 | 250 |

It is thus apparent that the new phenylalanine derivatives exhibited an excellent α4-integrin inhibiting activity.

Since the new phenylalanine derivatives of the present invention have excellent α4-integrin inhibiting activity, the present invention provides a therapeutic agent or preventive agent for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The above-described inflammatory bowel diseases include Crohn's disease and ulcerative colitis.

In this purpose, the compound of the present invention has high bioavailability and/or blood level when administered orally. Therefore, an oral administration of a drug is effective.

The compound of the present invention also has high stability in acidic or alkaline solution and is effective, for example, as it is possible to apply to various dosage forms.

What is claimed is:

1. A compound of formula (1):

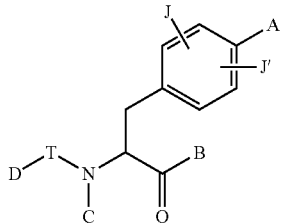

wherein:

A represents a group of formula (3):

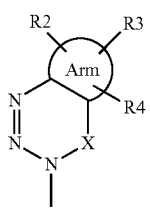

wherein Arm represents a cyclic alkyl group or an aromatic ring containing 0, 1, 2, 3, or 4 hetero atoms selected from the group consisting of an oxygen atom, a sulfur atom, and a nitrogen atom;

X represents C(=O), S(=O)$_2$, C(—R5)(—R6), C(=C(R5)(R6)), C(=S), S(=O), P(=O)(—OH), or P(—H)(=O);

R2, R3, R4, R5, and R6 may be the same or different from one another and each independently represents a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkythio group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or an ammonium group, R5 and R6 may be bonded together to form a ring which may contain one or two oxygen, nitrogen or sulfur atoms B represents hydroxyl group, a lower alkoxyl group or hydroxylamino group;

C represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s);

D represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group;

C and D may be bonded together to form a ring which may contain one or two oxygen, nitrogen, or sulfur atoms;

T represents an interatomic bond, C(=O), C(=S), S(=O), S(=O)$_2$, N(H)—C(=O), or N(H)—C(=S);

J and J' may be the same or different from each other and each independently represents a hydrogen atom, a halogen atom, a lower alkyl group, a lower alkyloxy group or a nitro group;

or a pharmaceutically acceptable salt thereof.

2. A compound or pharmaceutically acceptable salt according to claim 1, wherein Arm represents a benzene ring.

3. A compound or pharmaceutically acceptable salt according to claim 1, wherein R2, R3, and R4 are each independently a hydrogen atom, a halogen atom, a hydroxyl group, a lower alkyl group, a substituted lower alkyl group, a lower alkoxyl group, a halogen lower alkyl group, substituted or unsubstituted amino group, or an ammonium group.

4. A compound or pharmaceutically acceptable salt according to claim 1, wherein B represents hydroxyl group or a lower alkoxyl group.

5. A compound or pharmaceutically acceptable salt according to claim 1, wherein C represents a hydrogen atom or a lower alkyl group.

6. A compound or pharmaceutically acceptable salt according to claim 1, wherein D represents a cycloalkyl group(s) which may contain a hetero atom(s) in the ring thereof, an aryl group, or a heteroaryl group.

7. A compound or pharmaceutically acceptable salt according to claim 1, wherein J and J' each represent a hydrogen atom.

8. A compound or pharmaceutically acceptable salt according to claim 1, wherein T represents C(=O).

9. A compound or pharmaceutically acceptable salt according to claim 1, wherein X represents C(=O) or C(=S).

10. A compound or pharmaceutically acceptable salt according to claim 1, wherein X is C(=O).

11. A compound or pharmaceutically acceptable salt according to claim 1, wherein:

Arm represents a benzene ring;

R2, R3, and R4 are each independently a hydrogen atom, a halogen atom, a hydroxyl group, a lower alkyl group, a substituted lower alkyl group, a lower alkoxyl group, a halogen lower alkyl group, substituted or unsubstituted amino group, or an ammonium group;

B represents hydroxyl group or a lower alkoxyl group;

C represents a hydrogen atom or a lower alkyl group;

D represents a cycloalkyl group(s) which may contain a hetero atom(s) in the ring thereof, an aryl group, or a heteroaryl group;

J and J' each represent a hydrogen atom;

T represents C(=O); and

X represents C(=O) or C(=S).

12. A compound or pharmaceutically acceptable salt according to claim 11, wherein X is C(=O).

* * * * *